United States Patent
Guney

(10) Patent No.: US 9,724,488 B2
(45) Date of Patent: *Aug. 8, 2017

(54) CUSHION FOR A RESPIRATORY MASK ASSEMBLY

(71) Applicant: ResMed Limited, Bella Vista, New South Wales (AU)

(72) Inventor: Memduh Guney, Sydney (AU)

(73) Assignee: ResMed Limited, Bella Vista (AU)

( * ) Notice: Subject to any disclaimer, the term of this patent is extended or adjusted under 35 U.S.C. 154(b) by 505 days.

This patent is subject to a terminal disclaimer.

(21) Appl. No.: 14/251,000

(22) Filed: Apr. 11, 2014

(65) Prior Publication Data
US 2014/0202464 A1 Jul. 24, 2014

Related U.S. Application Data

(60) Continuation of application No. 13/067,211, filed on May 17, 2011, now Pat. No. 8,733,358, which is a
(Continued)

(51) Int. Cl.
*A61M 11/00* (2006.01)
*A61M 16/06* (2006.01)
*A61M 16/08* (2006.01)

(52) U.S. Cl.
CPC ........ *A61M 16/0611* (2014.02); *A61M 16/06* (2013.01); *A61M 16/0616* (2014.02);
(Continued)

(58) Field of Classification Search
CPC .......... A61M 16/0611; A61M 16/0616; A61M 16/0633; A61M 16/0622; A61M 16/0825;
(Continued)

(56) References Cited

U.S. PATENT DOCUMENTS 443,191 A 12/1890 Illing
781,516 A 1/1905 Guthrie, Jr.
(Continued)

FOREIGN PATENT DOCUMENTS

AU 199651130 10/1996
AU 2005100738 11/2005
(Continued)

OTHER PUBLICATIONS

Office Action issued in corresponding Japanese Application No. 2010-195597 mailed Jul. 27, 2015, with English translation thereof.
(Continued)

*Primary Examiner* — Steven Douglas
(74) *Attorney, Agent, or Firm* — Nixon & Vanderhye P.C.

(57) ABSTRACT

A respiratory mask assembly including a frame and a cushion provided to the frame. The cushion including a non-face contacting portion removably attached to the frame and a face-contacting portion adapted to engage a patient's face. The face-contacting portion includes a side wall, a rim extending from the side wall and curving inwardly into a cavity of the cushion, and a membrane substantially surrounding the rim and including an inside surface spaced from an outside surface of the rim. The cushion includes a gusset portion extending radially outwardly from the side wall of the face-contacting portion and a reinforcing ring between the gusset portion and the face-contacting portion. The reinforcing ring is constructed and arranged to act as a stiffening hoop to reduce the tendency of the cushion to expand when under pressure.

28 Claims, 45 Drawing Sheets

Related U.S. Application Data continuation of application No. 12/382,517, filed on Mar. 18, 2009, now Pat. No. 7,958,893, which is a division of application No. 10/655,622, filed on Sep. 5, 2003, now Pat. No. 7,523,754, and a continuation-in-part of application No. 10/235,846, filed on Sep. 6, 2002, now Pat. No. 6,823,869.

(60) Provisional application No. 60/424,686, filed on Nov. 8, 2002, provisional application No. 60/483,622, filed on Jul. 1, 2003, provisional application No. 60/317,486, filed on Sep. 7, 2001, provisional application No. 60/342,854, filed on Dec. 28, 2001.

(52) U.S. Cl.
CPC .... *A61M 16/0622* (2014.02); *A61M 16/0633* (2014.02); *A61M 16/0638* (2014.02); *A61M 16/0683* (2013.01); *A61M 16/08* (2013.01); *A61M 16/0825* (2014.02); *Y10T 29/4987* (2015.01)

(58) Field of Classification Search
CPC .. A61M 16/0638; A61M 16/08; A61M 16/06; Y10T 29/4987
USPC ............ 128/205.25, 201.22–201.24, 201.29, 128/206.21, 206.24, 206.26, 206.28, 128/207.11, 207.13
See application file for complete search history.

(56) References Cited

U.S. PATENT DOCUMENTS

| | | | |
|---|---|---|---|
| 1,081,745 A | 12/1913 | Johnston |
| 1,125,542 A | 1/1915 | Humphries |
| 1,192,186 A | 7/1916 | Greene |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,625,155 A | 1/1953 | Engelder |
| 2,706,983 A | 4/1955 | Matheson et al. |
| 2,931,356 A | 4/1960 | Schwarz |
| 3,013,556 A | 12/1961 | Galleher |
| 3,330,273 A | 7/1967 | Bennett V |
| 3,670,726 A | 6/1972 | Mahon et al. |
| 3,682,171 A | 8/1972 | Dali et al. |
| 3,739,774 A | 6/1973 | Gregory |
| 3,754,552 A | 8/1973 | King |
| 3,861,385 A | 1/1975 | Carden |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,006,744 A | 2/1977 | Steer |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,414,973 A | 11/1983 | Matheson et al. |
| 4,422,456 A | 12/1983 | Teip |
| 4,449,526 A | 5/1984 | Elam |
| 4,455,675 A | 6/1984 | Bose et al. |
| 4,493,614 A | 1/1985 | Chu et al. |
| 4,548,200 A | 10/1985 | Wapner |
| 4,549,542 A | 10/1985 | Chein |
| 4,572,323 A | 2/1986 | Randall |
| 4,587,967 A | 5/1986 | Chu et al. |
| 4,601,465 A | 7/1986 | Roy |
| 4,617,637 A | 10/1986 | Chu et al. |
| 4,630,604 A | 12/1986 | Montesi |
| 4,641,647 A | 2/1987 | Behan |
| 4,660,555 A | 4/1987 | Payton |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| D293,613 S | 1/1988 | Wingler |
| 4,753,233 A | 6/1988 | Grimes |
| 4,767,411 A | 8/1988 | Edmunds |
| 4,774,946 A | 10/1988 | Ackerman et al. |
| 4,782,832 A | 11/1988 | Trimble et al. |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | AmRhein |
| 5,000,173 A | 3/1991 | Zalkin et al. |
| 5,003,633 A | 4/1991 | Itoh |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| D333,015 S | 2/1993 | Farmer et al. |
| 5,188,101 A | 2/1993 | Tumolo |
| 5,207,665 A | 5/1993 | Davis et al. |
| 5,220,699 A | 6/1993 | Farris |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,299,599 A | 4/1994 | Farmer et al. |
| 5,304,146 A | 4/1994 | Johnson et al. |
| 5,335,656 A | 8/1994 | Bowe et al. |
| 5,349,949 A * | 9/1994 | Schegerin ............... A62B 18/08 |
| | | | 128/201.24 |

(56) References Cited

U.S. PATENT DOCUMENTS

| | | |
|---|---|---|
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stem et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,488,948 A | 2/1996 | Dubruille et al. |
| 5,509,409 A | 4/1996 | Weatherholt |
| 5,513,634 A | 5/1996 | Jackson |
| 5,513,635 A | 5/1996 | Bedi |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,560,354 A | 10/1996 | Berthon-Jones et al. |
| 5,570,684 A | 11/1996 | Behr |
| 5,592,938 A | 1/1997 | Scarberry et al. |
| 5,623,923 A | 4/1997 | Bertheau et al. |
| 5,647,357 A | 7/1997 | Barnett et al. |
| 5,653,228 A | 8/1997 | Byrd |
| 5,655,527 A | 8/1997 | Scarberry et al. |
| 5,662,101 A | 9/1997 | Ogden et al. |
| 5,682,881 A | 11/1997 | Winthrop et al. |
| 5,704,345 A | 1/1998 | Berthon-Jones et al. |
| 5,707,342 A | 1/1998 | Tanaka |
| 5,724,965 A | 3/1998 | Handke et al. |
| 5,735,272 A | 4/1998 | Dillon et al. |
| 5,740,799 A | 4/1998 | Nielsen |
| 5,752,511 A | 5/1998 | Simmons et al. |
| 5,794,619 A | 8/1998 | Edeiman et al. |
| 5,807,341 A | 9/1998 | Heim |
| 5,842,469 A | 12/1998 | Rapp et al. |
| 5,906,203 A | 5/1999 | Klockseth et al. |
| 5,918,598 A | 7/1999 | Belfer et al. |
| 5,921,239 A | 7/1999 | McCall et al. |
| 5,954,049 A | 9/1999 | Foley et al. |
| 5,975,079 A | 11/1999 | Hellings et al. |
| 6,019,101 A | 2/2000 | Cotner et al. |
| 6,026,811 A | 2/2000 | Settle |
| 6,044,844 A | 4/2000 | Kwok et al. |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,109,263 A | 8/2000 | Feuchtgruber |
| 6,112,746 A * | 9/2000 | Kwok .................. A61B 5/097 |
| | | 128/206.26 |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,193,914 B1 | 2/2001 | Harrison |
| 6,196,223 B1 | 3/2001 | Belfer et al. |
| 6,211,263 B1 | 4/2001 | Cinelli et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,038 B1 | 12/2001 | Kessler et al. |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,358,279 B1 | 3/2002 | Tahi et al. |
| 6,374,826 B1 | 4/2002 | Gunaratnam et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huizen |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Gunaratnam et al. |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,701,927 B2 | 3/2004 | Kwok et al. |
| 6,710,099 B2 | 3/2004 | Cinelli et al. |
| 6,766,800 B2 | 7/2004 | Chu et al. |
| 6,766,817 B2 | 7/2004 | da Silva |
| 6,776,162 B2 | 8/2004 | Wood |
| 6,776,163 B2 | 8/2004 | Dougill et al. |
| 6,789,543 B2 | 9/2004 | Cannon |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,860,270 B2 | 3/2005 | Sniadach |
| 6,895,965 B2 | 5/2005 | Scarberry et al. |
| 6,907,882 B2 | 6/2005 | Ging et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,052,127 B2 | 5/2006 | Harrison |
| 7,066,586 B2 | 6/2006 | da Silva |
| 7,076,282 B2 | 7/2006 | Munro et al. |
| 7,080,645 B2 | 7/2006 | Genger et al. |

(56) References Cited

U.S. PATENT DOCUMENTS

| | | |
|---|---|---|
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,191,781 B2 | 3/2007 | Wood |
| 7,207,328 B1 | 4/2007 | Altemus |
| 7,210,481 B1 | 5/2007 | Lovell et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,318,437 B2 | 1/2008 | Gunaratnam et al. |
| 7,523,754 B2 | 4/2009 | Lithgow et al. |
| 7,658,189 B2 | 2/2010 | Davidson |
| 7,958,893 B2 | 6/2011 | Lithgow |
| 2001/0020474 A1 | 9/2001 | Hecker et al. |
| 2002/0005198 A1 | 1/2002 | Kwok et al. |
| 2002/0029780 A1 | 3/2002 | Frater et al. |
| 2002/0046755 A1 | 4/2002 | DeVoss |
| 2002/0053347 A1 | 5/2002 | Ziaee |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0124849 A1 | 9/2002 | Billette De Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2002/0185134 A1 | 12/2002 | Bishop |
| 2003/0000526 A1 | 1/2003 | Goebel |
| 2003/0019495 A1 | 1/2003 | Palkon et al. |
| 2003/0075180 A1 | 4/2003 | Raje et al. |
| 2003/0079749 A1 | 5/2003 | Strickland et al. |
| 2003/0089373 A1 | 5/2003 | Gradon et al. |
| 2003/0111080 A1 | 6/2003 | Olsen et al. |
| 2003/0154980 A1 | 8/2003 | Berthon-Jones et al. |
| 2003/0168063 A1 | 9/2003 | Gambone et al. |
| 2003/0196656 A1 | 10/2003 | Moore et al. |
| 2003/0196658 A1 | 10/2003 | Ging et al. |
| 2004/0025882 A1 | 2/2004 | Madaus et al. |
| 2004/0025885 A1 | 2/2004 | Payne, Jr. |
| 2004/0045551 A1 | 3/2004 | Eaton et al. |
| 2004/0065328 A1 | 4/2004 | Amarasinghe et al. |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0118406 A1 | 6/2004 | Lithgow et al. |
| 2004/0127856 A1 | 7/2004 | Johnson |
| 2004/0211428 A1 | 10/2004 | Jones |
| 2004/0226564 A1 | 11/2004 | Persson |
| 2004/0226566 A1 | 11/2004 | Gunaratnam et al. |
| 2005/0011523 A1 | 1/2005 | Aylsworth et al. |
| 2005/0028822 A1 | 2/2005 | Sleeper et al. |
| 2005/0033247 A1 | 2/2005 | Thompson |
| 2005/0039757 A1 | 2/2005 | Wood |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0101933 A1 | 5/2005 | Marrs et al. |
| 2005/0150495 A1 | 7/2005 | Rittner et al. |
| 2005/0155604 A1 | 7/2005 | Ging et al. |
| 2005/0211252 A1 | 9/2005 | Lang et al. |
| 2005/0241644 A1 | 11/2005 | Gunaratnam et al. |
| 2005/0284481 A1 | 12/2005 | Meyer |
| 2006/0060200 A1 | 3/2006 | Ho et al. |
| 2006/0081250 A1 | 4/2006 | Bordewick et al. |
| 2006/0095008 A1 | 5/2006 | Lampropoulos et al. |
| 2006/0095009 A1 | 5/2006 | Lampropoulos et al. |
| 2006/0118117 A1 | 6/2006 | Berthon-Jones |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0237017 A1 | 10/2006 | Davidson et al. |
| 2006/0283461 A1 | 12/2006 | Lubke et al. |
| 2007/0023044 A1 | 2/2007 | Kwok et al. |
| 2007/0125387 A1 | 6/2007 | Zollinger et al. |
| 2007/0144525 A1 | 6/2007 | Davidson et al. |
| 2007/0186930 A1 | 8/2007 | Davidson et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110469 A1 | 5/2008 | Weinberg |
| 2008/0200880 A1 | 8/2008 | Kyvik et al. |
| 2008/0257354 A1 | 10/2008 | Davidson et al. |
| 2009/0044808 A1 | 2/2009 | Guney et al. |
| 2009/0178679 A1 | 7/2009 | Lithgow et al. |
| 2010/0000534 A1 | 1/2010 | Kooij et al. |
| 2010/0018534 A1 | 1/2010 | Veliss et al. |
| 2011/0220114 A1 | 9/2011 | Lithgow et al. |

FOREIGN PATENT DOCUMENTS

| | | |
|---|---|---|
| DE | 185017 | 5/1907 |
| DE | 30 11 900 | 10/1980 |
| DE | 146 688 | 2/1981 |
| DE | 37 19 009 | 12/1988 |
| DE | 39 27 038 | 2/1991 |
| DE | 29723101 U1 | 7/1998 |
| DE | 197 03 526 | 8/1998 |
| DE | 199 44 242 | 3/2001 |
| DE | 100 02 571 | 7/2001 |
| DE | 102 13 905 | 10/2002 |
| DE | 10 2004 055 433 | 11/2004 |
| EP | 0 288 937 | 11/1988 |
| EP | 0 427 474 | 5/1991 |
| EP | 0 466 960 | 1/1992 |
| EP | 303090 B1 | 4/1992 |
| EP | 0 658 356 | 6/1995 |
| EP | 0 776 679 | 6/1997 |
| EP | 1099452 | 5/2001 |
| EP | 1 116 492 | 7/2001 |
| EP | 1 258 266 | 11/2002 |
| EP | 1 481 702 | 12/2004 |
| FR | 2 720 280 | 12/1995 |
| GB | 532214 | 1/1941 |
| GB | 2 176 404 | 12/1986 |
| GB | 2 368 533 | 5/2002 |
| GB | 2 385 533 | 8/2003 |
| JP | H03-007173 | 1/1991 |
| JP | 2000-515784 | 11/2000 |
| JP | 2003-175106 | 6/2003 |
| JP | 2003-535657 | 12/2003 |
| WO | WO 82/03548 | 10/1982 |
| WO | WO 87/01950 | 4/1987 |
| WO | WO 92/20392 | 11/1992 |
| WO | WO 92/20395 | 11/1992 |
| WO | WO 96/28207 | 9/1996 |
| WO | WO 98/04310 | 2/1998 |
| WO | WO 98/12965 | 4/1998 |
| WO | WO 98/23305 | 6/1998 |
| WO | WO 99/16327 | 4/1999 |
| WO | WO 99/25410 | 5/1999 |
| WO | WO 99/43375 | 9/1999 |
| WO | WO 99/61088 | 12/1999 |
| WO | WO 00/20072 | 4/2000 |
| WO | WO 00/38772 | 7/2000 |
| WO | WO 00/50121 | 8/2000 |
| WO | WO 00/69521 | 11/2000 |
| WO | WO 00/72905 | 12/2000 |
| WO | WO 00/74758 | 12/2000 |
| WO | WO 00/76568 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |

(56) References Cited

FOREIGN PATENT DOCUMENTS

| | | |
|---|---|---|
| WO | WO 01/97893 | 12/2001 |
| WO | WO 02/38221 | 5/2002 |
| WO | WO 02/45784 | 6/2002 |
| WO | WO 03/090827 | 11/2003 |
| WO | WO 03/105921 | 12/2003 |
| WO | WO 2004/022146 | 3/2004 |
| WO | WO 2004/041342 | 5/2004 |
| WO | WO 2004/073778 | 9/2004 |
| WO | WO 2004/078230 | 9/2004 |
| WO | WO 2005/053781 | 6/2005 |
| WO | WO 2005/063328 | 7/2005 |
| WO | WO 2005/086943 | 9/2005 |
| WO | WO 2005/099801 | 10/2005 |
| WO | WO 2005/110220 | 11/2005 |
| WO | WO 2005/118040 | 12/2005 |
| WO | PCT/AU2006/000031 | 1/2006 |
| WO | PCT/AU2006/000417 | 3/2006 |
| WO | PCT/AU2006/000770 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | PCT/AU2007/001936 | 12/2007 |
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/108994 | 9/2009 |
| WO | WO 2009/109004 | 9/2009 |
| WO | WO 2010/028425 | 3/2010 |

OTHER PUBLICATIONS

Extended European Search Report issued in corresponding European Appln. No. 15 16 0073.1 dated Jun. 3, 2015.
U.S. Appl. No. 10/385,701, filed Aug. 2003, Berthon-Jones et al.
U.S. Appl. No. 10/533,928, filed Jul. 2005, Berthon-Jones.
U.S. Appl. No. 10/584,711, filed Dec. 2004, Davidson.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/597,909, filed Jul. 2007, Worboys.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/309,696, filed Jan. 2009, Kwok et al.
U.S. Appl. No. 12/448,250, filed Jun. 2009, Veliss et al.
U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
"Ear Loop Face Mask".
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
"If You Hate CPAP! You Need CPAP Pro®," www.cpappro.com.
Webster's New World Dictionary, Third College Edition 1988, definition for engaged and flexible.
European Search Report filed on Jul. 27, 2009 in EP Application No. 07784697.0.
European Search Report issued in EP 07845378.4, mailed Dec. 1, 2009.
Examination Report filed in New Zealand Application 539836, dated Aug. 25, 2005.
Examiner's Report No. 3 mailed Nov. 18, 2009 in New Zealand Application No. 2003275762.
Extended European Search Report dated Mar. 19, 2009 in European Application No. EP 08161249.
Extended European Search Report Mailed Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/osa/products.asp/.
Hans Rudolph, Inc.—Mask Products—http://www.rudolphkc.com/products.php?category=MASKS.
International Preliminary Report on Patentability for PCT/AU2004/001832, dated Jul. 3, 2006.
International Search Report for PCT/AU2005/000803, dated Jun. 30, 2005.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action mailed Dec. 22, 2009 in European Appln. No. 04802133.1.
ResMed Co.—Mask Products—http://resmed.com/portal/site/ResMedUS/index.jsp? . . . .
Respironics Co.—Mask Family—http://masksfamily.respironics.com/.
Snapp Nasal Interface, Tiara Medical Systems, Inc.—http://www.tiaramed.com/asp_shops/shopdisplayproducts.asp?id=109&cat=SNAPP%2A+Nasal+Interface.
Subbu Venkatraman et al., "Review Skin Adhesives and Skin Adhesion 1. Transdermal Drug Delivery Systems," Biomaterials, vol. 19, 1998, pp. 1119-1136.

(56) References Cited

OTHER PUBLICATIONS

Supplementary European Search Report mailed Sep. 8, 2009 in European Appln. No. 04802133.1.
Supplementary European Search Report mailed Dec. 18, 2009 in European Application No. 03810331.3.
Supplementary Search Report issued in European Appln. 05746824.1, dated Dec. 17, 2009.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
EP Supplementary Search Report issued in EP Appln. 03793493 (Dec. 2, 2009).
Office Action issued in European Appln. No. 03793493.2 (Mar. 18, 2011).
Office Action issued in related Japanese Appln. No. 2009-140433 (Aug. 20, 2011) with English translation thereof.
Office Action issued in related Chinese Appln. No. 201010000226.3 (Apr. 26, 2012) with English translation thereof.
Office Action issued in related a Japanese Appln. No. 2010-1955897 (Jun. 12, 2012) with English translation thereof.
Notice of Allowance issued in related Japanese Appln. No. 2009-140433 (Sep. 4, 2012).
Office Action issued in corresponding Chinese Appln. No. 201010000226.3 (Jan. 14, 2013) with English translation thereof.
Office Action issued in corresponding Japanese Patent Appln. No. 201010000226.3 (Jun. 3, 2013) with English translation thereof.
Office action issued in corresponding European Patent Appln. No. 03 793 493.2-1662 (Jun. 7, 2013).
Final Office Action issued in corresponding Japanese appln. No. 2010-195597 (Jun. 25, 2013) with English translation thereof.
Decision of Rejection issued in corresponding Japanese Appln. No. 2010-195597 dated Apr. 28, 2014, with English translation thereof.
Decision to Reject the Amendments issued in corresponding Japanese Appln. No. 2010-195597 dated Apr. 28, 2014, with English translation thereof.
Summons to Attend Oral Proceedings issued in corresponding European Appln. No. 03793493.2 dated May 6, 2014.

\* cited by examiner

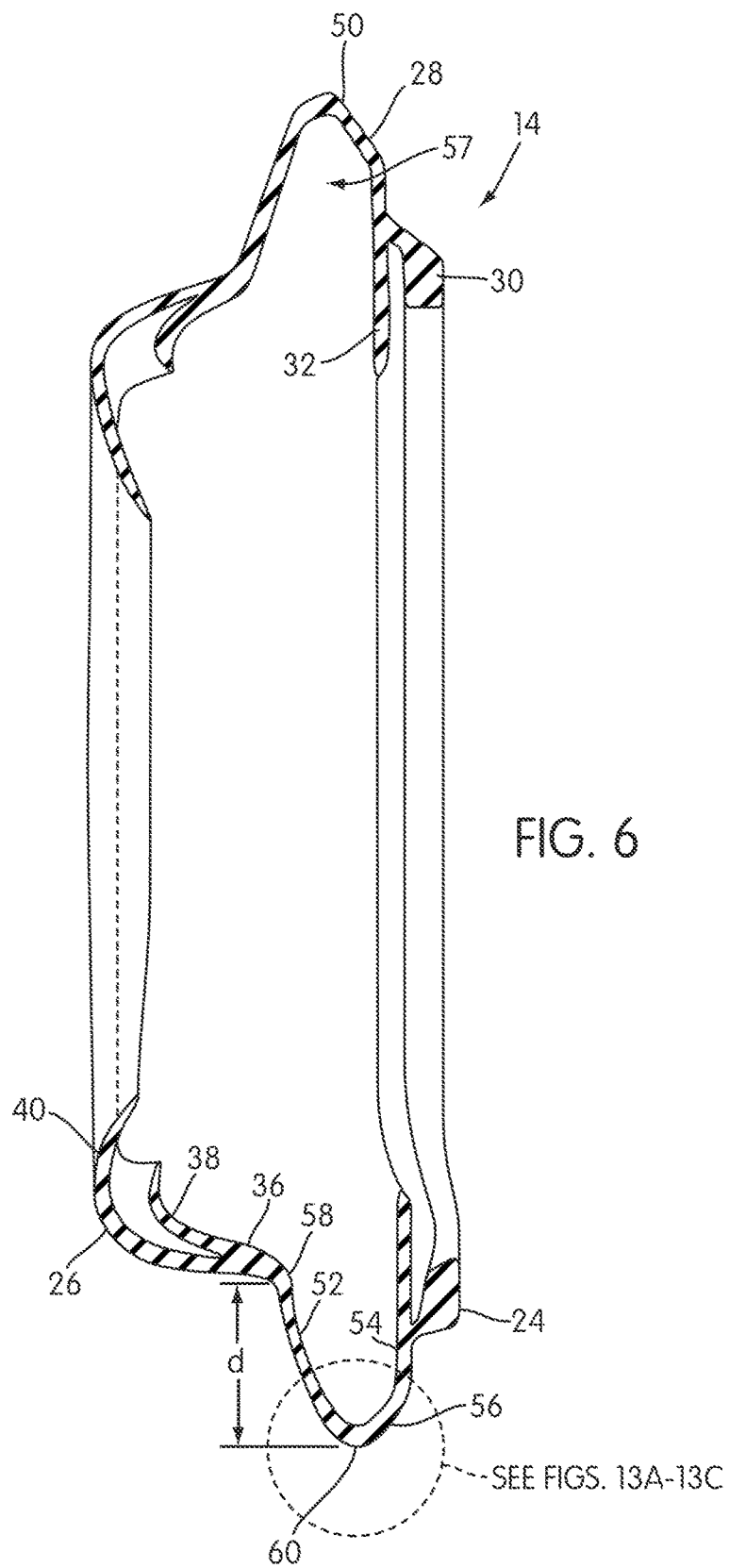

Tailored Contact Force to keep within the zone for constant gusset extension

CUSHION FOR A RESPIRATORY MASK ASSEMBLY

CROSS REFERENCE TO PRIORITY APPLICATIONS

This application is a continuation of U.S. patent application Ser. No. 13/067,211, filed May 17, 2011, allowed, which is a continuation of U.S. patent application Ser. No. 12/382,517, filed Mar. 18, 2009, now U.S. Pat. No. 7,958, 893, which is a divisional of U.S. patent application Ser. No. 10/655,622, filed Sep. 5, 2003, now U.S. Pat. No. 7,523,754, which claims the benefit of U.S. Provisional Application No. 60/424,686 filed Nov. 8, 2002, U.S. Provisional Application No. 60/483,622 filed Jul. 1, 2003, and is a Continuation-In-Part of U.S. Non-Provisional application Ser. No. 10/235, 846 filed Sep. 6, 2002, now U.S. Pat. No. 6,823,869, which in turn claims priority to U.S. Provisional Application No. 60/317,486 filed Sep. 7, 2001 and U.S. Provisional Application No. 60/342,854 filed Dec. 28, 2001. Each of the above identified applications is incorporated herein by reference in its entirety.

FIELD OF THE INVENTION

The present invention relates to a cushion for a respiratory mask assembly used for providing ventilatory support, e.g., for treatment of Sleep Disordered Breathing (SDB) with Non-invasive Positive Pressure Ventilation (NPPV).

BACKGROUND OF THE INVENTION

The use of NPPV for treatment of SDB such as Obstructive Sleep Apnea (OSA) was pioneered by Sullivan (see U.S. Pat. No. 4,944,310). Apparatus for the treatment of SDB involves a blower which delivers a supply of air at positive pressure to a patient interface via a conduit. The patient interface may take several forms, such as a nasal mask assembly and a nasal and mouth mask assembly. Patients typically wear a mask assembly while sleeping to receive the NPPV therapy.

Mask assemblies typically comprise a rigid shell or frame and a soft face-contacting cushion. The cushion spaces the frame away from the patient's face. The frame and cushion define a cavity which receives the nose or nose and mouth. The frame and cushion are held in position on the patient's face by a headgear assembly. The headgear assembly typically comprises an arrangement of straps which pass along both sides of the patient's face to the back or crown of the patient's head.

U.S. Pat. No. 5,243,971 (Sullivan and Bruderer) describes a nasal mask assembly for Continuous Positive Airway Pressure (CPAP) having a ballooning/molding seal that conforms with the patient's nose and facial contours. The mask assembly has a face-contacting portion mounted to a shell which is sized and shaped to overfit the nose region of the patient. The face-contacting portion is in the form of a distendable membrane which is molded from an elastic plastics material. The distendable membrane and the shell together define a chamber. Pressurized gas admitted to the chamber causes the membrane to distend outwardly from the patient's face. The contents of this patent are hereby incorporated by reference.

U.S. Pat. No. 6,112,746 (Kwok et al.) describes a nasal mask assembly and a mask cushion therefor. The cushion comprises a substantially triangularly shaped frame from which extends a membrane. The frame has a scalloped edge by which the cushion is affixed to a mask body. The membrane has an aperture into which the patient's nose is received. The membrane is spaced away from the rim of the frame, and its outer surface is of substantially the same shape as the rim. The contents of this patent are hereby incorporated by reference.

In a traditional mask assembly including a cushion, a seal is formed between the cushion and the face of a patient as the result of a contact force which acts along a contact line of the cushion. The contact force typically is a function of tension in the headgear straps which acts through the frame of the mask assembly, the walls of the cushion and the seal-forming portion of the cushion. In a traditional mask assembly, the frame defines a cavity or volute adapted to receive at least a portion of the nose, with the cushion forming a perimeter of the cavity. Thus, in use, the portion of the patient's face within the cavity is exposed to air or breathable gas at positive pressure and hence receives a force as the result of that positive pressure.

PCT Patent Application AU01/00746, published as WO 01/97893 (Frater et al.), describes a mask assembly for delivering air to a patient that includes a suspension mechanism to allow relative movement between a face-contacting cushion and a mask shell. The suspension mechanism also provides a predetermined force to the cushion that is a function of mask pressure, displacement of the cushion, or both. The contents of this patent are hereby incorporated by reference.

U.S. Pat. No. 5,074,297 (Venegas) describes a respiratory mask assembly for use with intermittent positive pressure breathing treatment which is said to facilitate the formation and automatic adjustment of the seal between a patient's face and a facial unit of the respiratory mask. The respirator mask assembly comprises a facial unit, an expandable piston adjacent the facial unit and a rigid support structure attached to one end of the piston, and an attachment mechanism for securing the mask assembly to a patient. During the inspiration portion of the ventilation cycle a positive pressure is developed within the mask assembly, causing the piston to expand. Because the attachment mechanism and the support cooperate to resist significant expansion of the piston, a force is generated which presses the facial unit against the patient's face and maintains an air tight seal. When pressure within the mask unit decreases, the contact force on the facial unit is likewise decreased and the seal is eliminated.

A common problem with prior art mask assemblies, such as the mask assemblies taught by U.S. Pat. Nos. 5,074,297, 5,243,971 and 6,112,746 and PCT Patent Application AU01/ 00746, is patient comfort. Patients can develop sores and red marks on their faces after several hours use of a mask assembly. The nasal bridge area of the patient's face has been identified as being particularly sensitive.

Moreover, the face contacting portion may apply excessive pressure to the wearer's face resulting in discomfort and possibly skin irritation. This can occur when the face contacting portion is distorted beyond its normal range of elasticity to conform to certain facial contours, thus requiring the application of excessive forces to obtain a seal. In some cases, these excessive pressures and forces may cause the wearer's face to distort to conform with the face contacting portion, which increases wearer discomfort, facial soreness and ulceration.

Another common problem with prior art mask assemblies is buildup of $CO_2$ in the mask cavity. Mask assemblies typically include a vent which allows the continuous washout of exhaled gasses from the cavity. One factor affecting the washout of exhaled gases is the dead space within the mask cavity.

Another common problem with these masks is a broken or ineffective seal. for example, the mask may become dislodged if the wearer rolls over when sleeping, thereby creating a drag force on the gas supply line which is transmitted to the mask and breaking the seal between the mask and wearer. If a mask is used for the administration of Continuous Positive Airway Pressure (CPAP) treatment for the condition obstructive sleep apnea, such a leak can result in a pressure supplied to the entrance of the wearer's airway that is below the therapeutic value. Thus, treatment becomes ineffective.

Another problem with mask assemblies which include a gusset section is visual size, both perceived and actual.

Another problem with existing full face masks occurs when wearers move their jaws during treatment, which often happens. As a result, air leaks are created below the mouth from the mid-region extending to the region at the sides or corners of the mouth.

It would be desirable to design a respiratory mask that can be securely sealed to a wearer's face without causing discomfort and minimize leak.

SUMMARY OF THE INVENTION

One aspect of the invention is directed towards a mask assembly having a cushion that provides more comfort to the patient.

Another aspect of the invention is directed towards a mask assembly having a cushion that controllably distributes facial contact pressure around the patient's face.

Another aspect of the invention is directed towards a mask assembly having a cushion that controllably distributes facial contact forces around a contact line on the patient's face.

Another aspect of the present invention provides a respiratory mask assembly for delivering breathable gas to a patient. The respiratory mask assembly according to one embodiment includes a frame and a cushion. The cushion has a non-face contacting portion structured to be connected to the frame, a face-contacting portion structured to engage the patient's face, and an intermediate portion that interconnects the non-face contacting portion and the face-contacting portion. The intermediate portion includes a gusset portion that applies a first component of force to the patient's face through the face-contacting portion. A spring structure is coupled with the face-contacting portion of the cushion. The spring structure applies a second component of force to the patient's face through the face-contacting portion. The first and second components of force applied by the gusset portion and spring structure, respectively, determine a contact force of the cushion applied to the patient's face through the face-contacting portion.

Another aspect of the invention is directed towards a mask assembly having a curvature which follows the line of the patient's face.

Another aspect of the invention is directed towards a mask assembly having a gusset portion which has minimal impingement of a patient's vision.

Another aspect of the invention is directed towards a mask assembly having a cushion with a gusset portion which has a low profile.

Another aspect of the invention is directed towards a mask assembly having a gusset portion which seals at a low pressure and which is comfortable at high pressures.

Another aspect of the invention is directed towards a mask assembly having a cushion with gusset portion which provides stop structures to regulate pressure distribution.

Another aspect of the invention is directed towards a mask assembly having a gusset portion providing additional footprint area and a spring section with a spring constant constructed so that the forces on the face from the cushion are a function of the additional footprint area, the mask pressure and the spring constant of the spring section.

Another aspect of the invention is to provide an elastic cuff to the cushion. The elastic cuff may have a modulus of elasticity which is greater than a modulus of elasticity of the remaining portions of the cushion, such that it may vary more easily deform or stretch in response to localized pressure and/or force changes between the mask and the wearer's face, thereby avoiding a compromise in the seal during movement of the patient. The elastic cuff may be formed in one piece with the cushion, along an intermediate portion of the cushion between the contacting and non-contacting portions of the cushion. The elastic cuff may also be formed separate from the cushion and assembled to the contacting and/or non-contacting portions of the cushion.

A further aspect of embodiments of the invention provides a full face mask with a cushion that forms a stable and reliable seal with a wearer's face.

An additional aspect of embodiments of the invention provides a full face mask that effectively seals the region directly below and/or to the sides of the lower lip.

A further aspect of embodiments of the invention provides a full face mask that offers effective sealing at relatively high pressures.

Another aspect of embodiments of the invention provides a full face mask that abuts the more stable bony regions of a wearer's face.

A further aspect of embodiments of the invention provides a full face mask that follows the natural contour of the face's bony structure below the mouth.

In one example, a full face respiratory mask comprises a frame including a breathable gas port and cushion. The frame defines an inner chamber that receives a wearer's nasal region and mouth. The cushion includes a flange connected to the frame, an inner rim defining an opening to the inner chamber of the frame, and a sealing portion disposed between the flange and the inner rim that contacts the wearer's face. The sealing portion includes a nasal seal section that spans a wearer's face above the wearer's nares, side seal sections extending from each side of the nasal seal section on both sides of the wearer's mouth, and a chin seal section that extends between the side sections. The chin seal section is upwardly curved in an arch to follow the chin's bony contour.

In another example, a cushion for use in a full face respiratory mask, comprises a flange for connection to a mask frame, an inner rim defining an opening for surrounding the wearer's nares and mouth, and a sealing portion disposed between the flange and the inner rim that contacts the wearer's face. The sealing portion includes a nasal seal section that spans a wearer's face above the wearer's nares, side seal sections extending from each side of the nasal seal section on both sides of the wearer's mouth, and a chin seal section that extends between the side sections, wherein the chin seal section is upwardly curved in an arch to follow the chin's bony contour.

Principles of these examples may be applied to any type of cushion for use on a respiratory mask, including but not limited to silicone elastomer, gel, foam or any combination thereof.

Principles of these examples may be applied to any type of respiratory mask, including CPAP systems or non-positive ventilation masks, such as respirators.

Other aspects, features and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 6 is a cross-sectional view of the cushion shown in FIG. 1;

DETAILED DESCRIPTION OF ILLUSTRATED EMBODIMENTS

Figure 1:
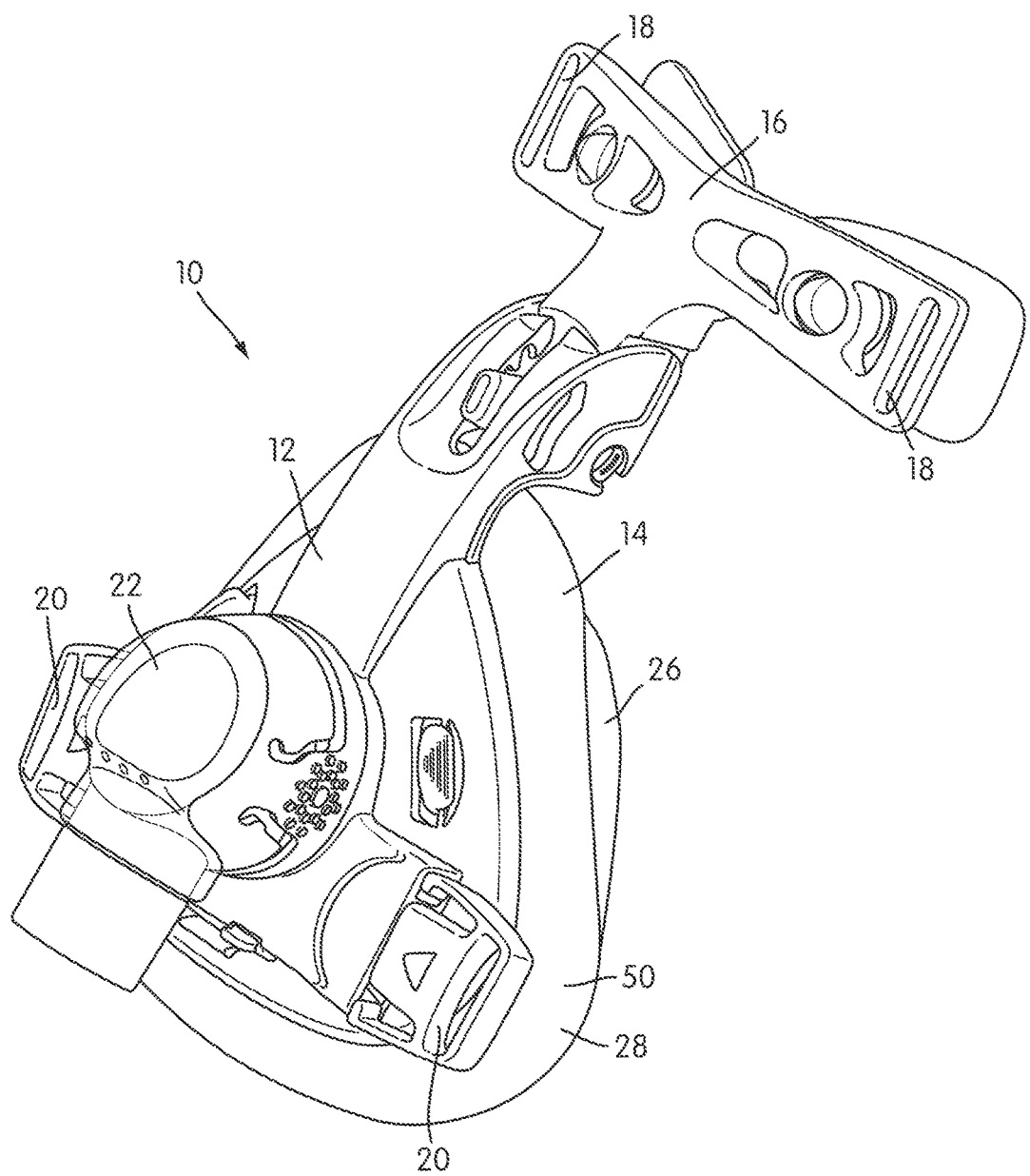
FIG. 1 is a front perspective view illustrating a mask assembly having a cushion constructed in accordance with an embodiment of the invention.
Figure 1B:
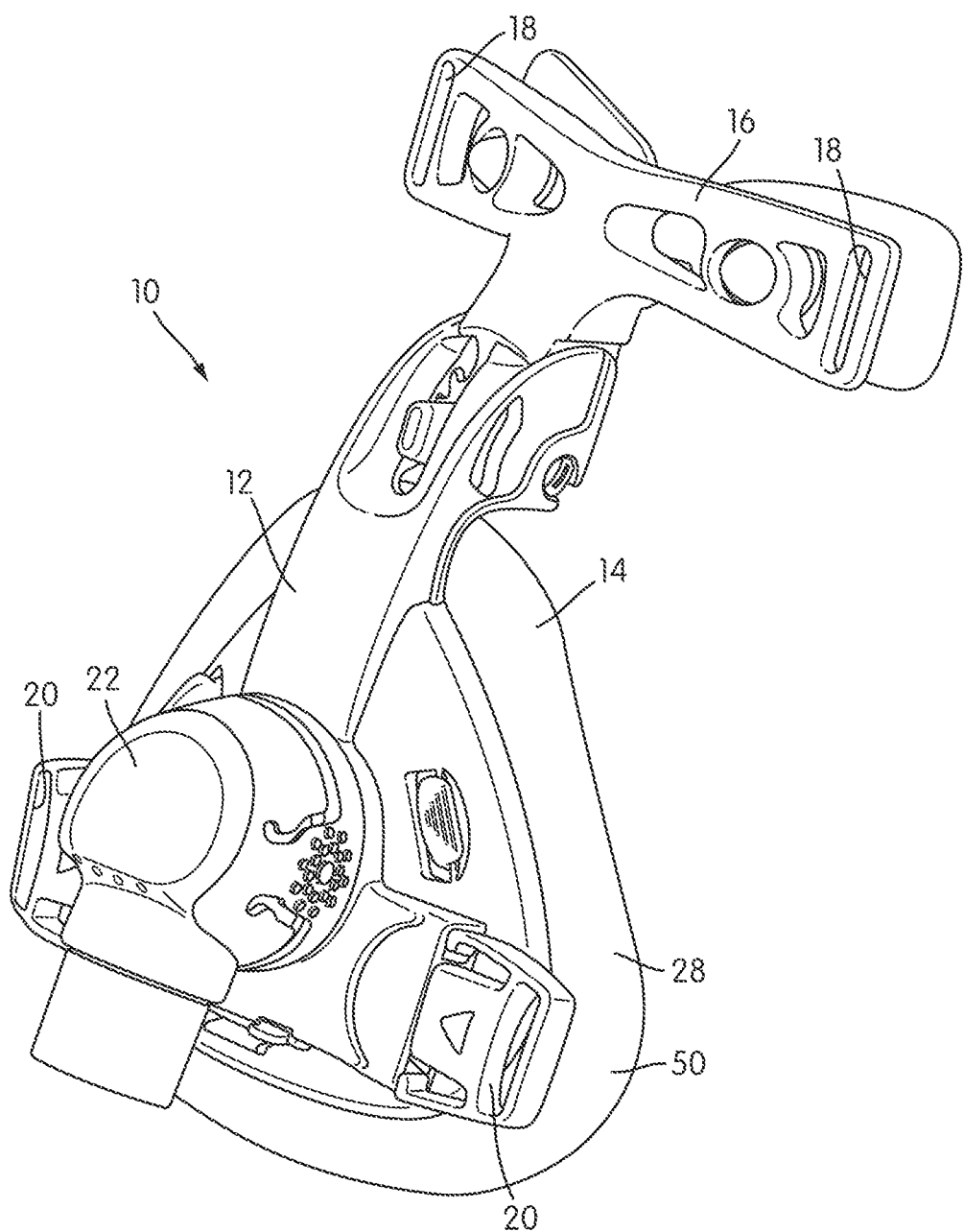
FIG. 1B is a perspective view similar to FIG. 1.
Figure 1C:
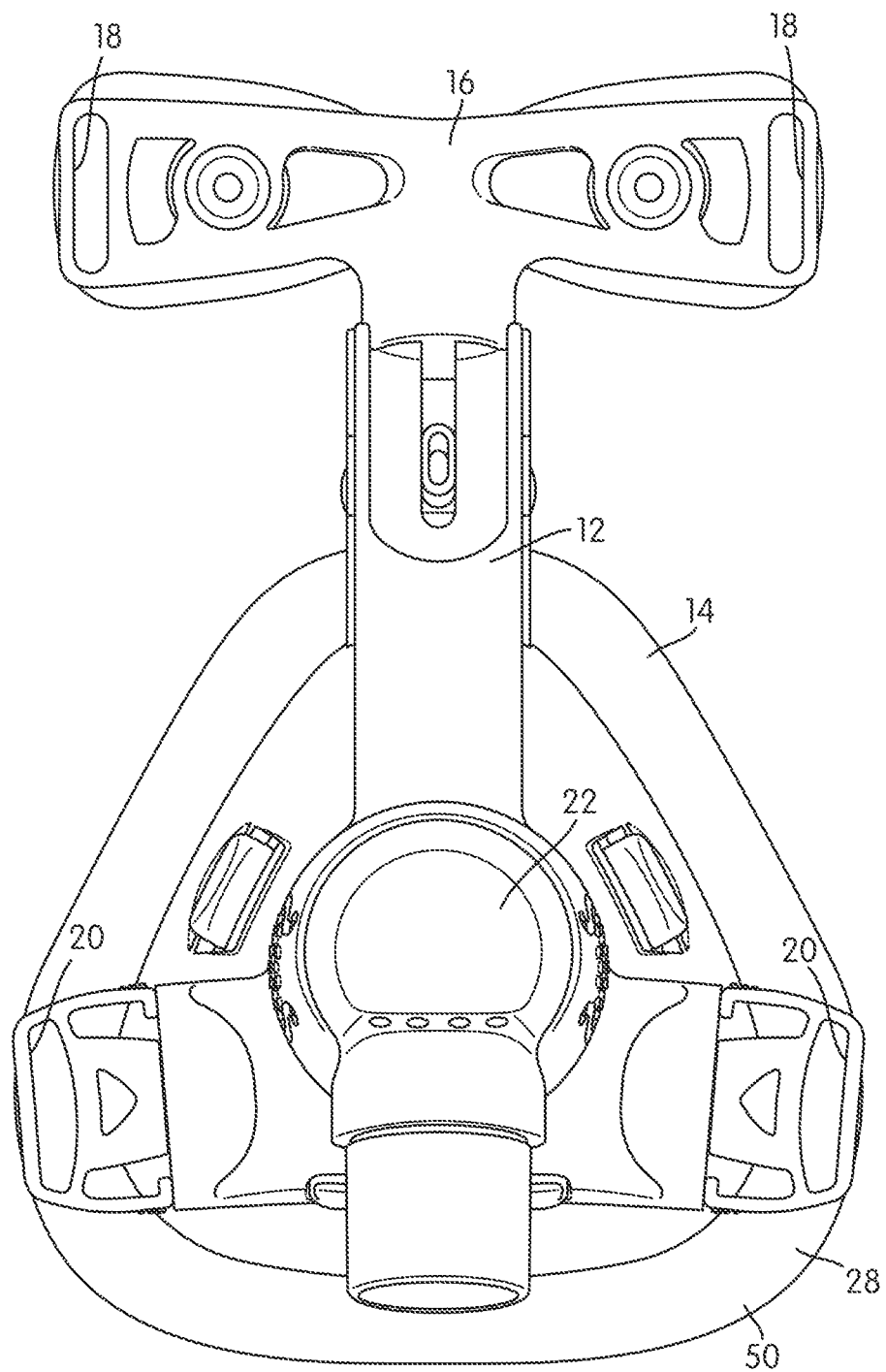
FIG. 1C is a perspective view similar to FIG. 1, but taken from another angle.
Figure 2:
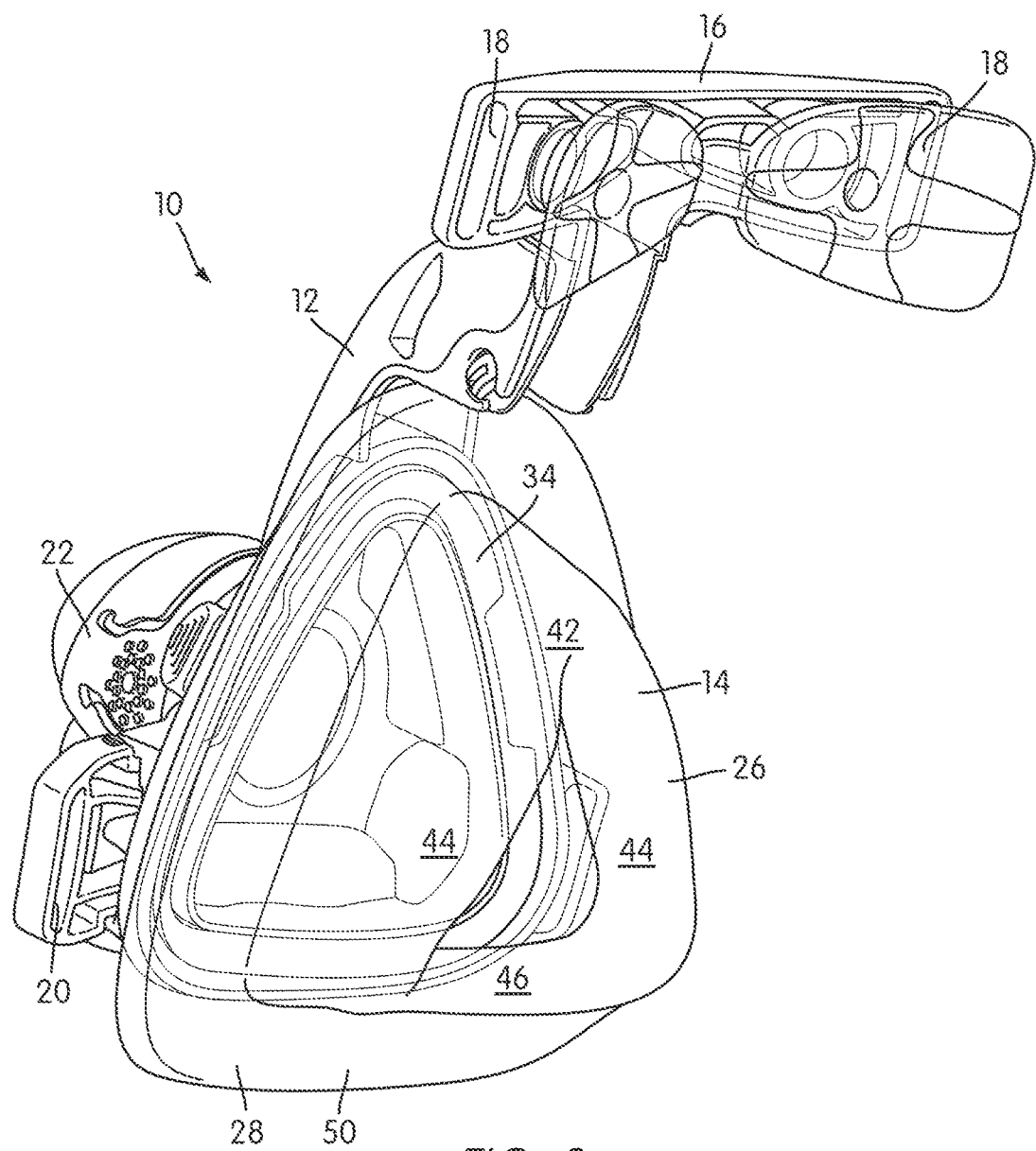
FIG. 2 is a rear perspective view of the mask assembly shown in FIG. 1.
Figure 2B:
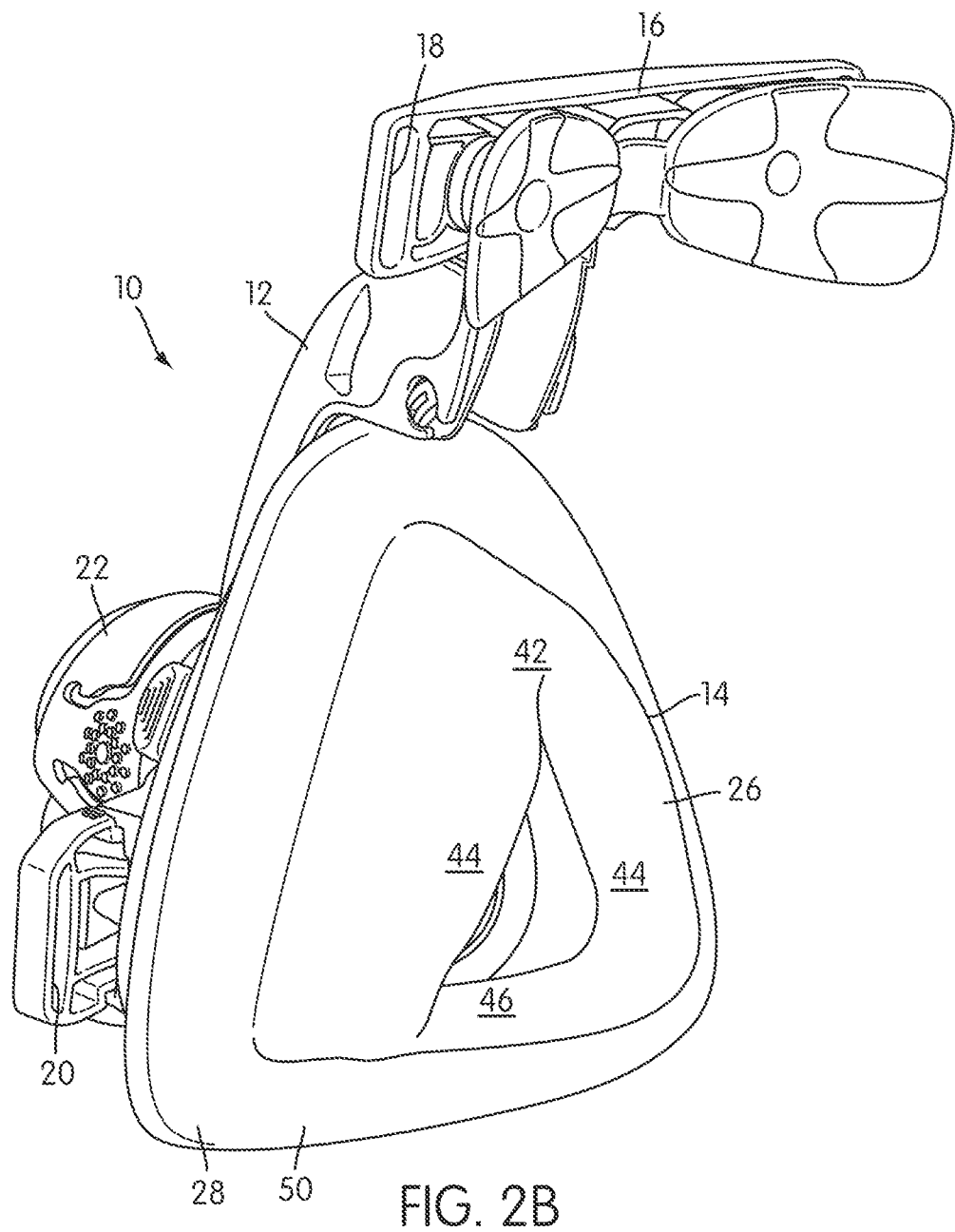
FIG. 2B is a perspective view similar to FIG. 2.
Figure 3:
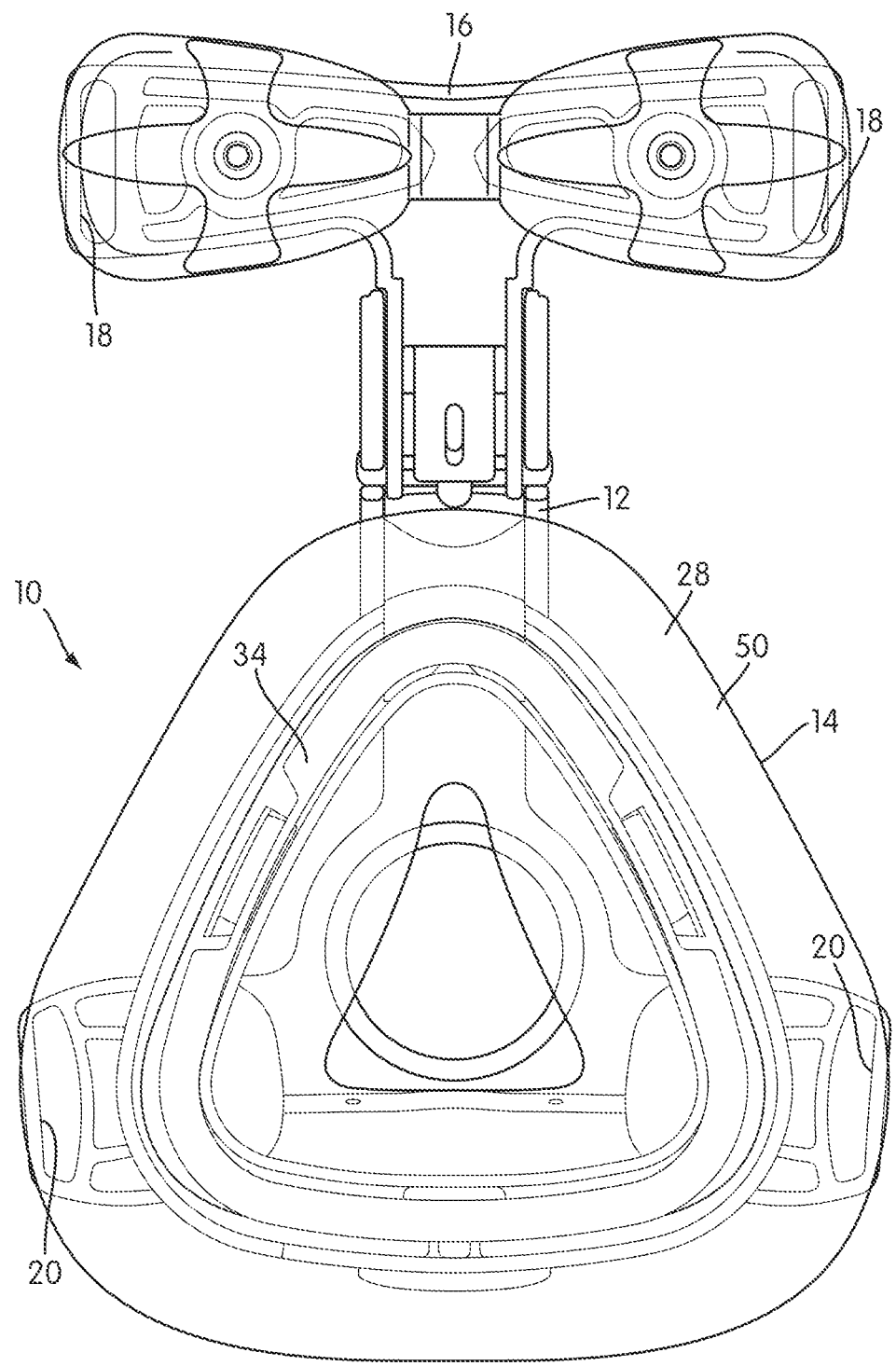
FIG. 3 is a rear view of the mask assembly shown in FIG. 1.
Figure 3B:
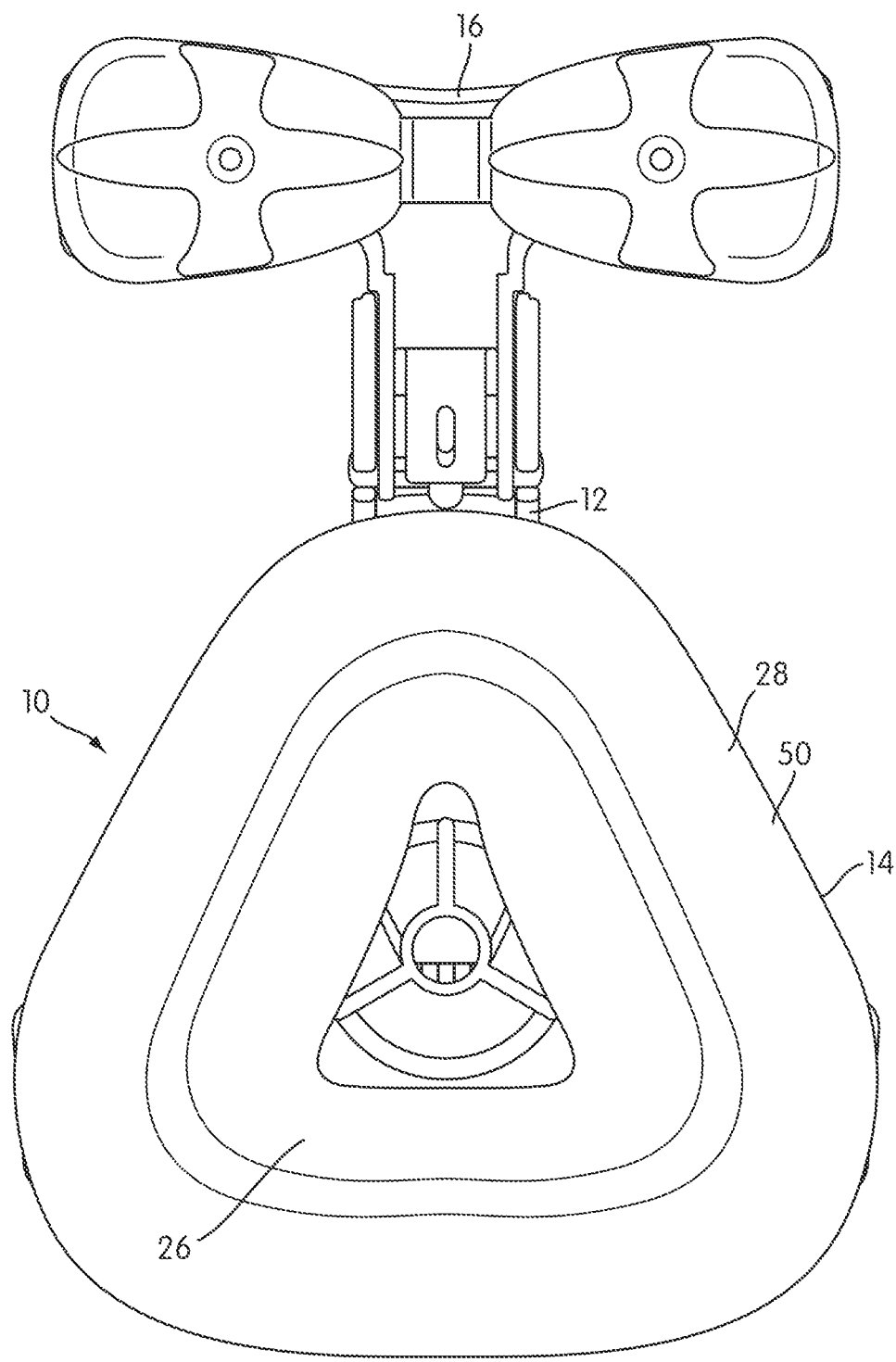
FIG. 3B is a perspective view similar to FIG. 3.
Figure 4:
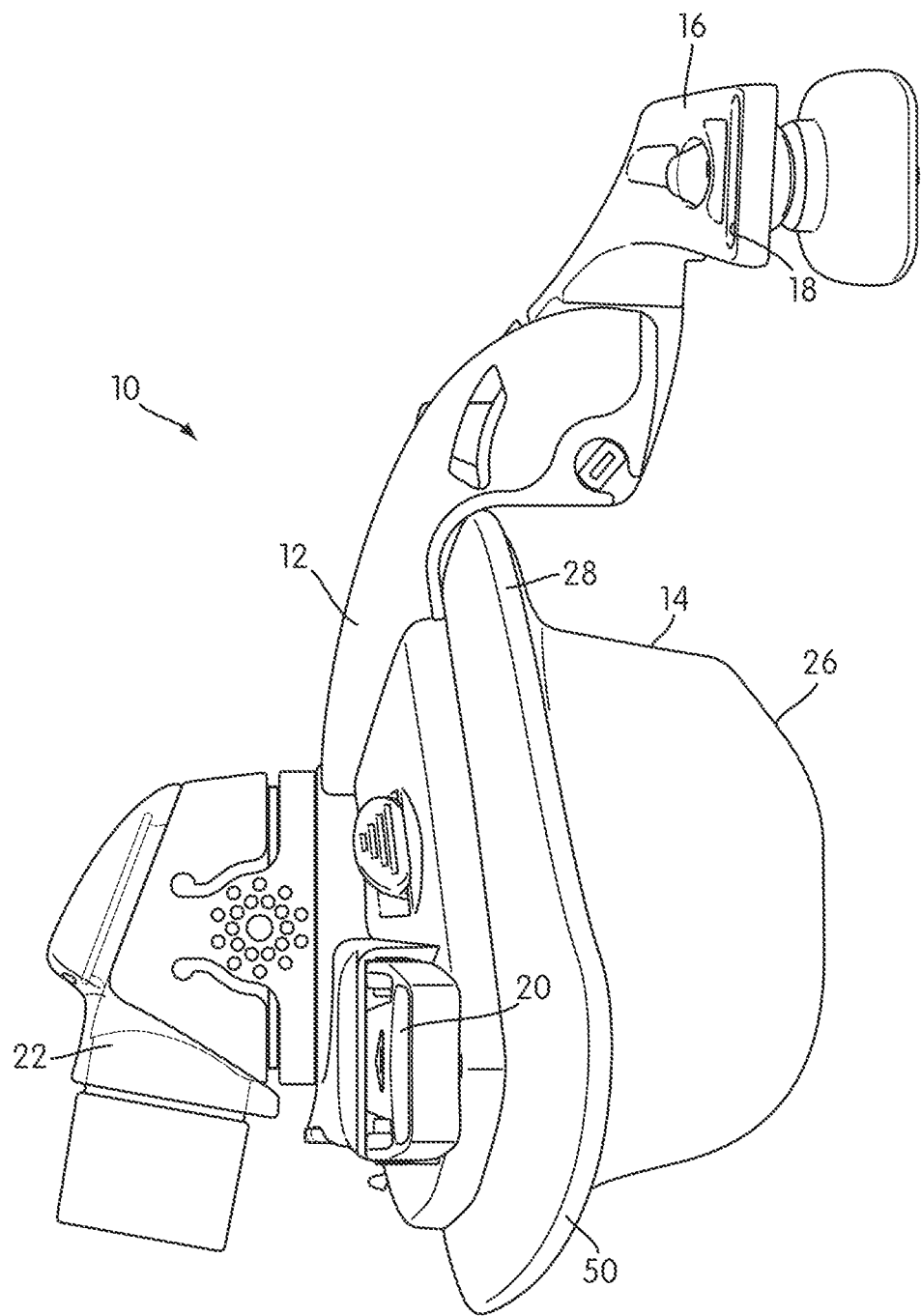
FIG. 4 is a side view of the mask assembly shown in FIG. 1.
Figure 4B:
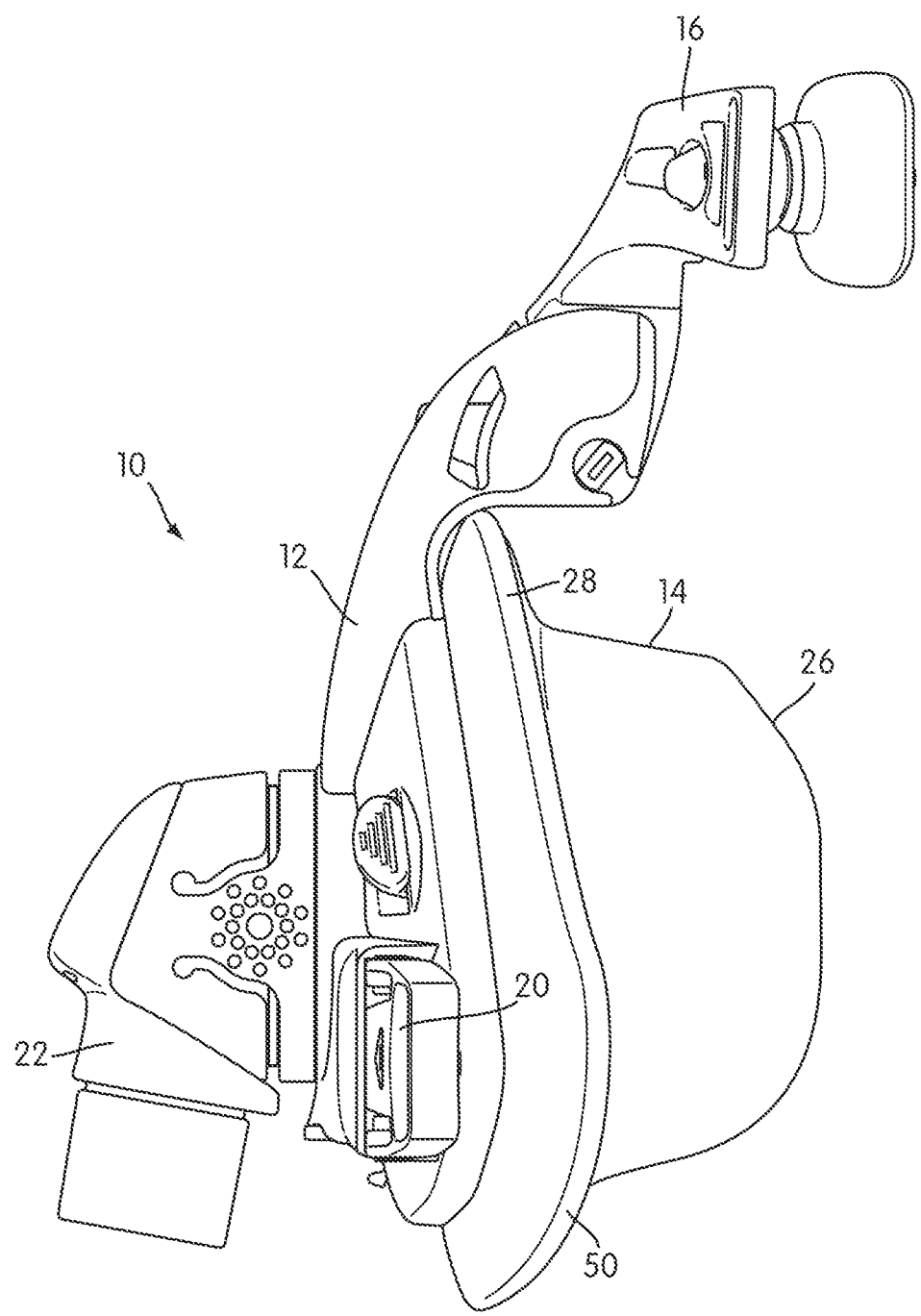
FIG. 4B is a perspective view similar to FIG. 4.
Figure 5:
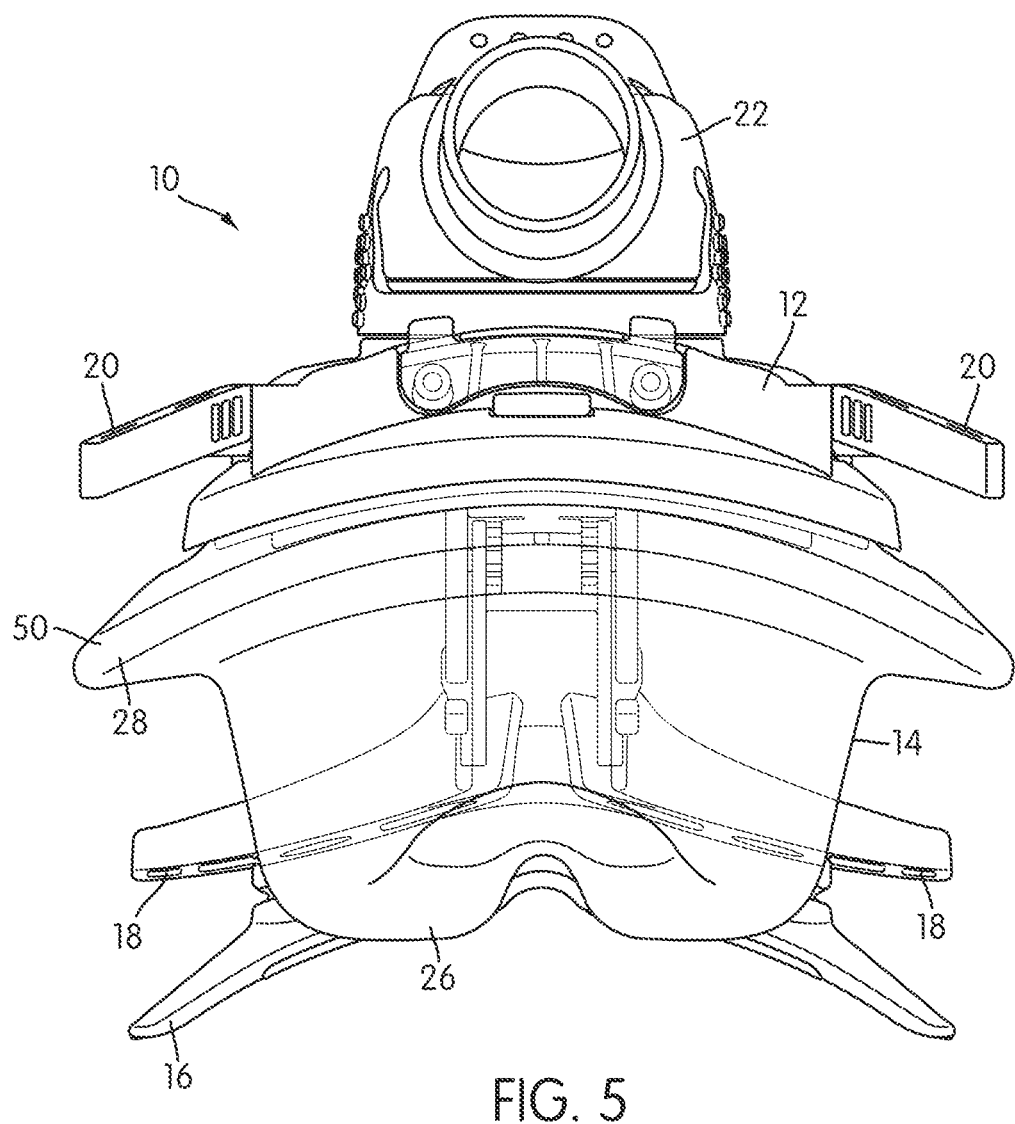
FIG. 5 is a bottom view of the mask assembly shown in FIG. 1.
Figure 5B:
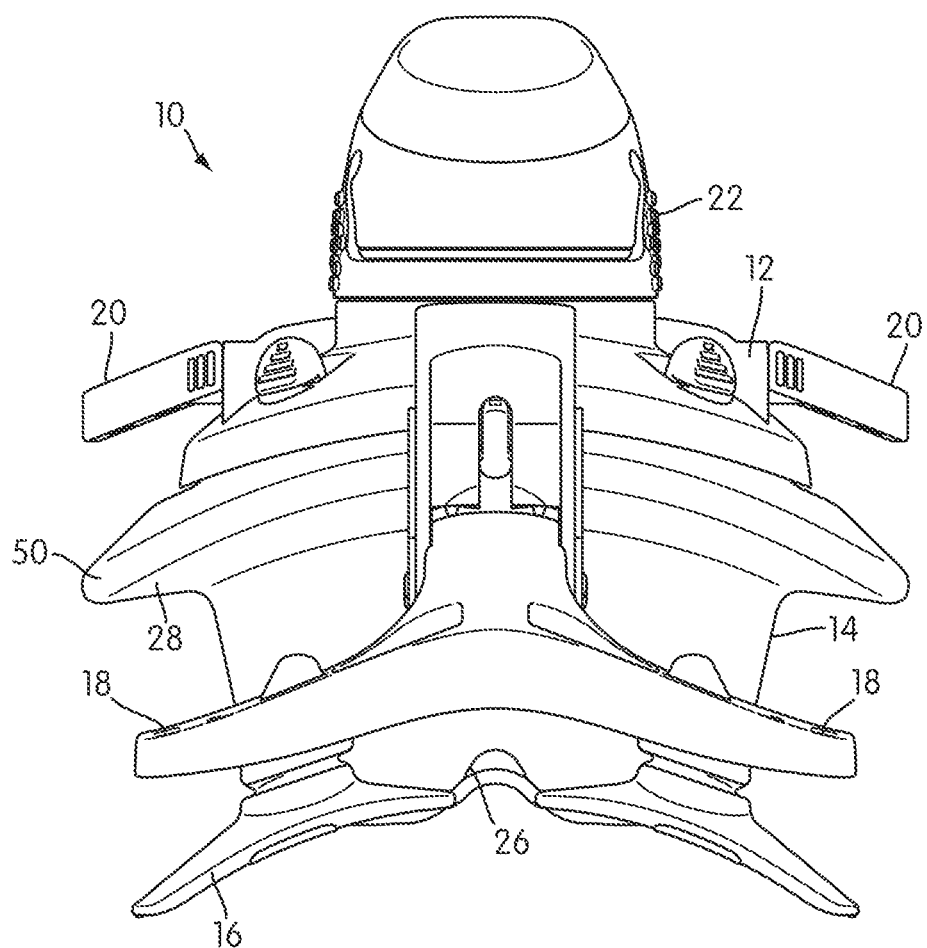
FIG. 5B is a top view of the mask assembly shown in FIG. 1.

FIGS. 1-5B show a respiratory mask assembly 10 that includes a frame 12 and a cushion 14 that may be permanently or removably connected to the frame 12. A forehead support 16 is movably mounted to an upper portion of the frame 12. A headgear assembly (not shown) can be removably attached to the frame 12 to maintain the frame 12 and cushion 14 in a desired adjusted position on the patient's face. For example, the headgear assembly may include a pair of upper and lower straps with the upper straps removably connected to clip structures 18 provided on the forehead support 16 and the lower straps removably connected to clip structures 20 provided on the frame 12. However, the headgear assembly and frame 12 may be removably attached to one another in any suitable manner.

In the illustrated embodiment, the mask assembly 10 is a nasal mask structured to deliver breathable gas to a patient's nose. However, the mask assembly 10 may be nasal and mouth mask or the mask assembly may be a full-face mask.

A swivel elbow assembly 22 is removably attached to a front portion of the frame 12. The elbow assembly 22 is structured to be connected to a conduit that is connected to a pressurized supply. The pressurized supply supplies pressurized breathable gas through the conduit and elbow assembly 22 and into the cushion 14 for breathing by the patient.

As shown in FIGS. 1-9B, the cushion 14 includes a non-face-contacting portion 24 (FIGS. 6 and 6C) structured to be connected to the frame 12, a face-contacting portion 26 structured to engage a patient's face, and an intermediate portion 28 that interconnects the non-face contacting portion 24 and the face-contacting portion 26. A seal-forming portion 68 (see FIG. 10B) of the cushion 14 is designed to seal on the patient's face. The cushion 14 achieves a seal by applying a contact force along the seal-forming portion 68 as will be described in further detail below. In one form, the seal-forming portion 68 is a strip with an area. For example, the strip 68 that contacts the patient's face could be that area between the dashed sets of lines in FIG. 10B. The contact force applied to sensitive regions on the patient's face can be minimized. Some portions of the patient's face require special attention to achieve a balance of comfort and seal.

In the illustrated embodiment, the non-face-contacting portion 24 of the cushion 14 is removably attached to the frame 12. For example, as shown in FIGS. 3, 3B, 6, 6C, and 15, the non-face-contacting portion 24 includes a shoulder 30 and a flange 32. A cushion clip 34 (see FIGS. 2, 2B, 3, and 3B) is detachably engaged with the frame 12 such that the shoulder 30 is positioned between the clip 34 and the frame 12 to attach the cushion 14 to the frame 12, e.g., see co-owned and co-pending U.S. patent application Ser. No. 10/235,846, filed on Sep. 6, 2002, incorporated herein by reference in its entirety. Further, the flange 32 is positioned to provide a seal. Alternatively, the non-face-contacting portion 24 of the cushion 14 may be removably attached to the frame 12 with straps, a friction or interference fit, and/or a tongue-and-groove arrangement, as is known in the art. However, the non-face-contacting portion 24 of the cushion 14 may be permanently attached to the frame 12 with glue and/or mechanical fastening means, for example.

As shown in FIGS. 6, 6C, and 14-33, a preferred face-contacting portion 26 of the cushion 14 includes a side wall 36, a rim 38 extending away from the side wall 36, and a membrane 40 provided to substantially surround the rim 38, e.g., see U.S. Pat. No. 6,112,746 of Kwok et al. and U.S. Provisional Application No. 60/402,509, filed on Aug. 12, 2002, incorporated herein by reference in its entirety. The rim 38 and side wall 36 provide a support structure for the face-contacting portion 26 and the membrane 40 provides a sealing structure for the face-contacting portion 26.

The membrane 40 provides a large effective rolled over section (large radius) to allow some degree of movement or rotation of the mask assembly 10 relative to the patient's face, and prevents the membrane distal edge from irritating the patient's face. Further, the membrane 40 extends further than the edge of the rim 38 to prevent the rim 38 from being a source of irritation.

The rim 38 has a curved shape that curves inwardly into the nasal cavity of the cushion 14. While it is preferable that the membrane 40 be thinner than the rim 38, they could have the same thicknesses.

The inside surface of the membrane 40 is spaced from the outside surface of the rim 38 so as to form a compliant seal with the patient. By compliant seal, it is meant that the membrane 40 can accommodate small variations in the shape of a patient's facial/nasal features without undue force, and can account for small movement of the mask relative to the patient during use, while maintaining an effective seal. The spacing between the rim 38 and membrane 40 may vary in different regions of the patient's face.

Figure 40:
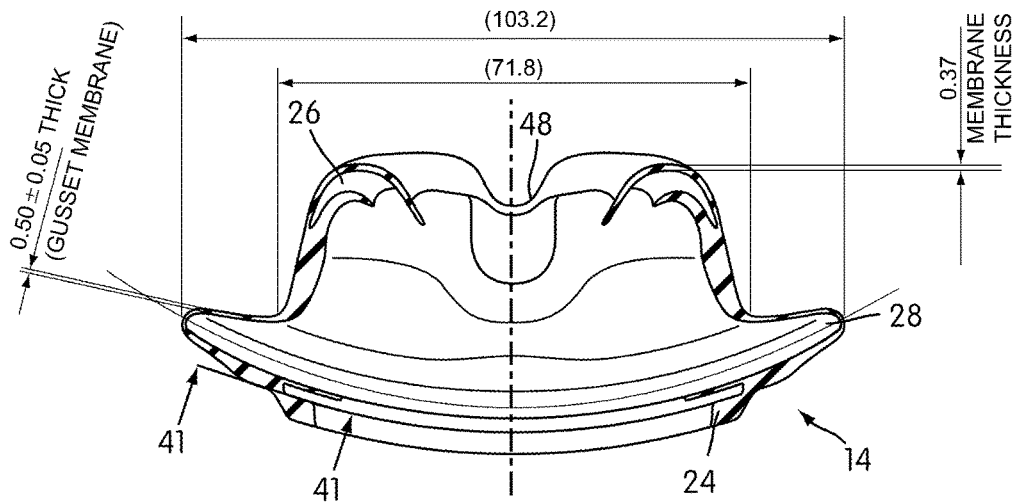
FIG. 40 is a cross-section taken along line 40-40 of FIG. 36.
Figure 41:
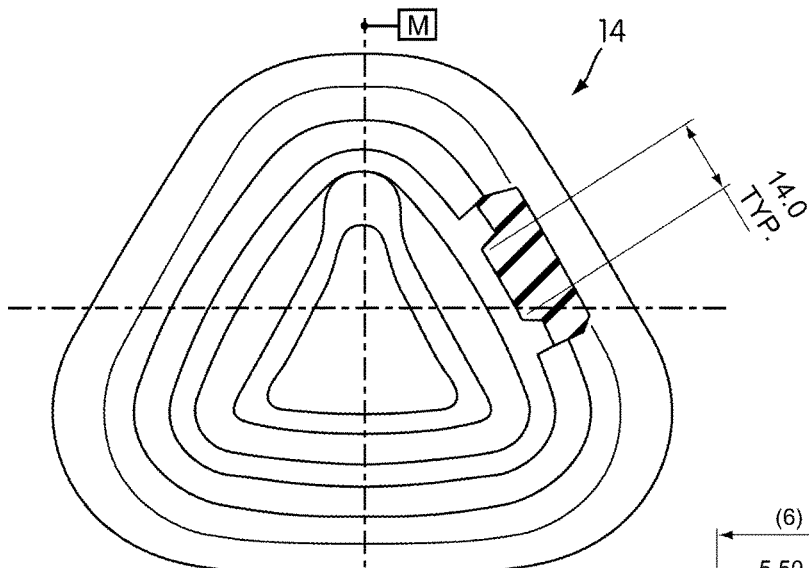
FIG. 41 is a cross-section taken along line 41-41 of FIG. 40.
Figure 42:
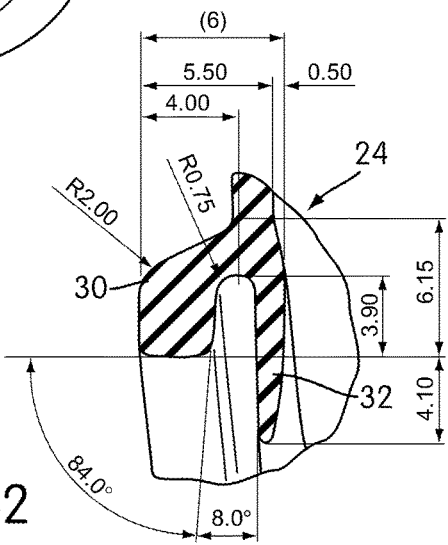
FIG. 42 is an enlarged cross-sectional view of FIG. 38.

As shown in FIGS. 2, 2B, and 10-11B, the face-contacting portion 26 of the cushion 14 preferably has a generally triangular shape and is structured to contact the nasal bridge, cheek, and lip regions of the patient. However, the face-contacting portion 26 may have any other suitable shape, e.g., a generally trapezoidal shape. In the illustrated embodiment, the cushion 14 includes a pair of cheek regions 44 to provide a seal in the crease between the cheeks and the sides of the nose, a lip region 46 to provide a seal below the nose and above the upper lip of the patient, and a nasal bridge region 42. The nasal bridge region 42 spans across the bridge and sloping sides of the bridge that intersect with the nasal crease formed between the cheeks and the sides of the nose. The transition between the lip region 46 and each cheek region 44 is where the cushion 14 begins to turn around the bottom of the nose towards the side of the nose. The transition between the nasal bridge region 42 and each cheek region 44 is where each cheek region 44 diverges upwardly towards the bridge of the nose. In other words, the nasal bridge region 42 starts where the cheek region 44 begins to angle upwardly. As shown in FIG. 40, the membrane 40 may include a preformed, contoured notch 48 in the nasal bridge region 42 to match generally the typical contours of the nasal bridge region of the patient.

The cushion 14, including the gusset portion 50, is curved to generally follow the curvature of the face. See FIGS. 4-5B and 7-9B. The advantages of the above structure include a reduced height profile, increased stability, better fit to the patient's face and a reduced visual impact. Other advantages include a reduced height at sides of the frame 12 and headgear clip section which might otherwise protrude from the mask frame, decreased weight and volume of silicone, decreased deadspace and stiffened gusset portion which holds its shape better.

In the illustrated embodiment, the membrane 40 is structured to contact an upper portion of the nasal bridge region of the patient. However, the membrane 40 may contact a lower portion of the nasal bridge region. For example, see U.S. Provisional Application No. 60/402,509, filed on Aug. 12, 2002, the contents of which are hereby incorporated by reference.

In the illustrated embodiment, the face-contacting portion 26 of the cushion 14 has a double-walled construction, e.g., one membrane 40 and one rim 38. However, the cushion 14 may have a single walled, triple walled or more walled construction. For example, a cushion with a combined membrane and rim could be provided, e.g., a single walled construction. Conversely, the support function of the rim could be accomplished with two or more support rims to support a single membrane, or two or more membranes could be provided over a single rim. In another alternative, the support function of the rim and the sealing function of the membrane could be split into two different members, which may be made of different materials, for example either being made of a foam. In another embodiment, a gel membrane may be used.

Figure 10:
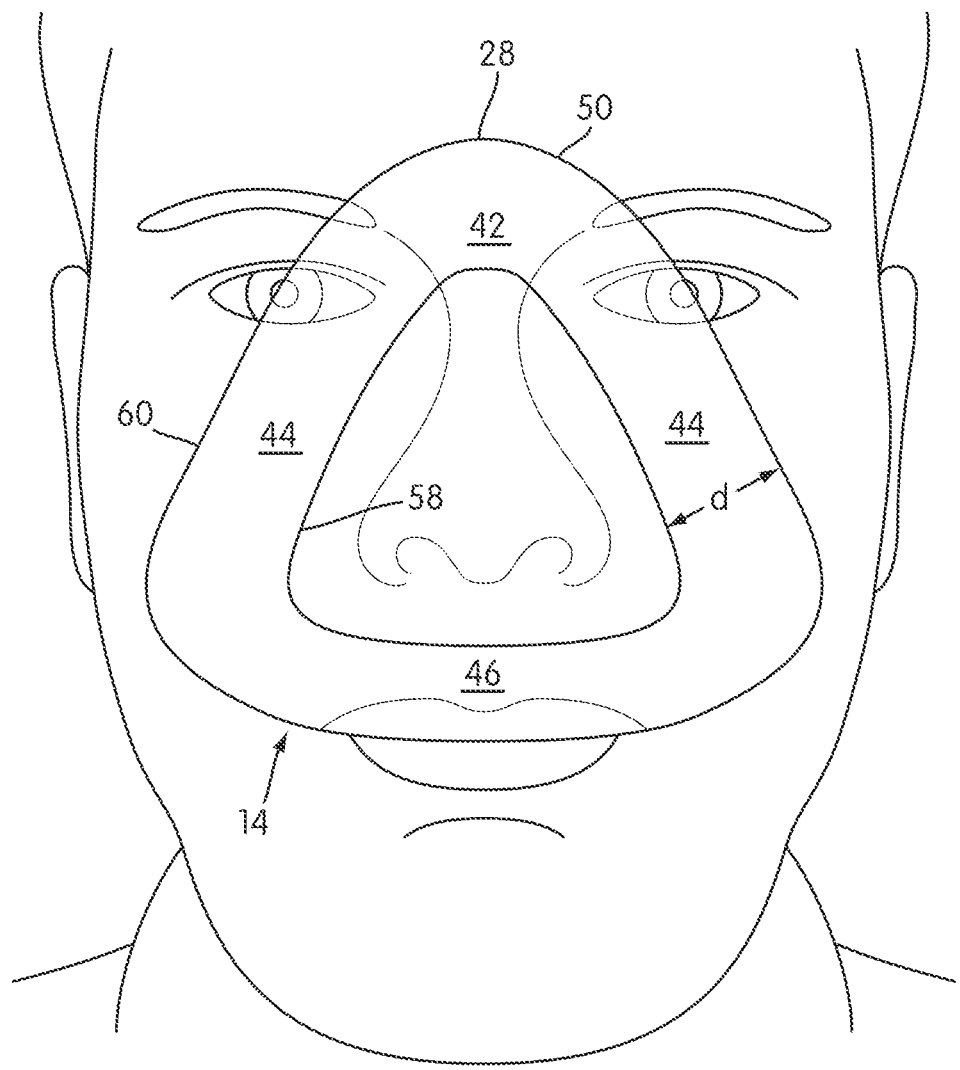
FIG. 10 is a front view of a gusset portion of the cushion shown in FIG. 1 superimposed on a patient's face.

The intermediate portion 28 of the cushion 14 includes a gusset portion 50 that extends radially outwardly with respect to the non-face-contacting and face-contacting portions 24, 26. The gusset portion 50 allows the face-contacting portion 26 to move relative thereto. Furthermore, the gusset portion 50 has a larger footprint area than the face-contacting portion 26 (e.g., FIG. 10 shows the gusset portion 50 superimposed on a patient's face to illustrate the additional area provided by the gusset portion 50). The additional footprint area of the gusset portion 50 provides a contact force on the patient's face acting on the sealing strip 68 (FIG. 10B) through the membrane 40, which increases the sealing efficiency of the cushion 14, as will be further discussed.

Figure 6B:
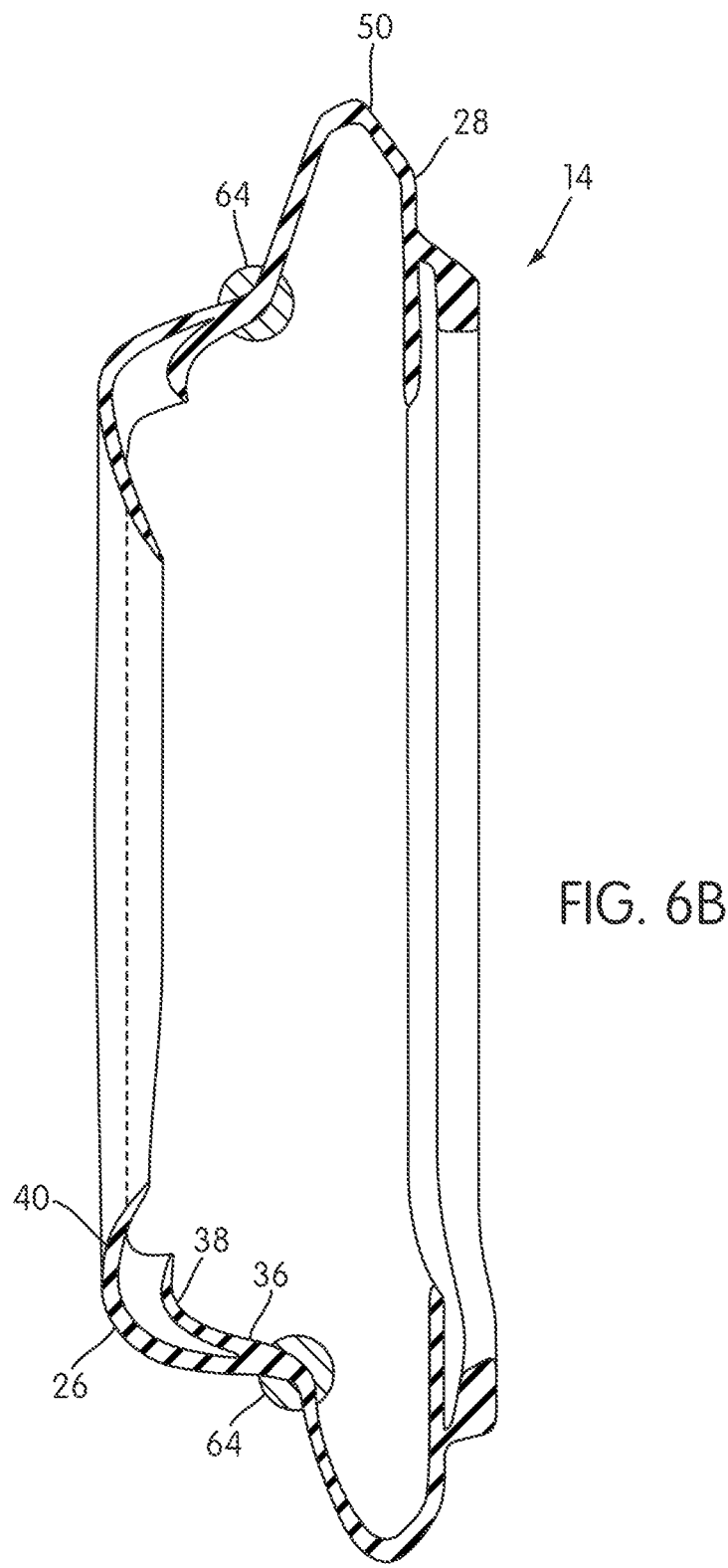
FIG. 6B is a cross-sectional view of the cushion shown in FIG. 1 in accordance with an alternative embodiment of the invention.
Figure 6C:
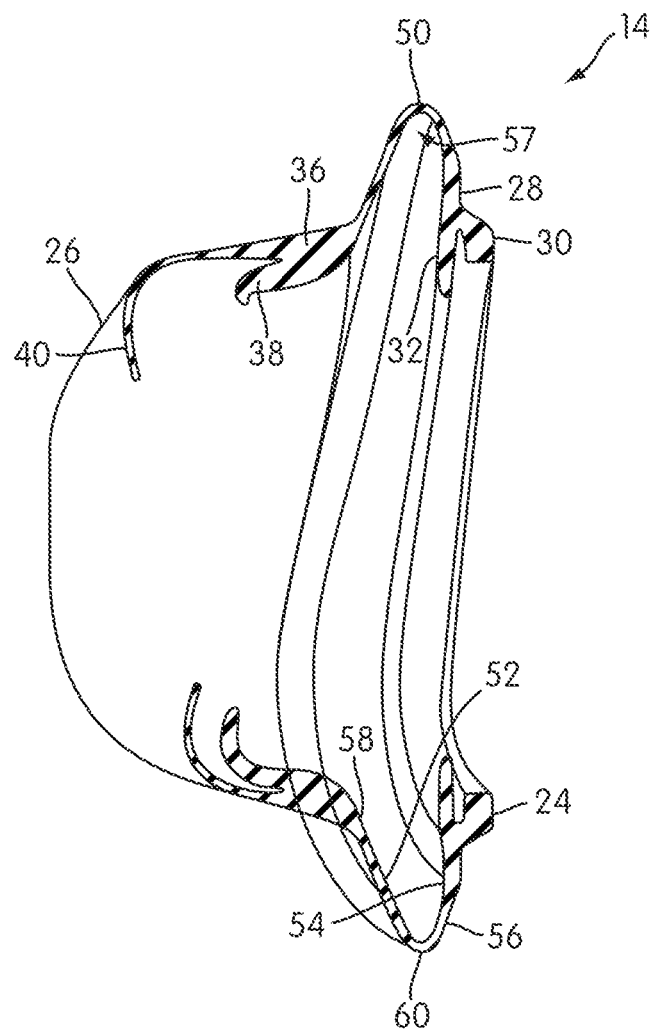
FIG. 6C is a perspective view similar to FIG. 6.
Figure 7B:
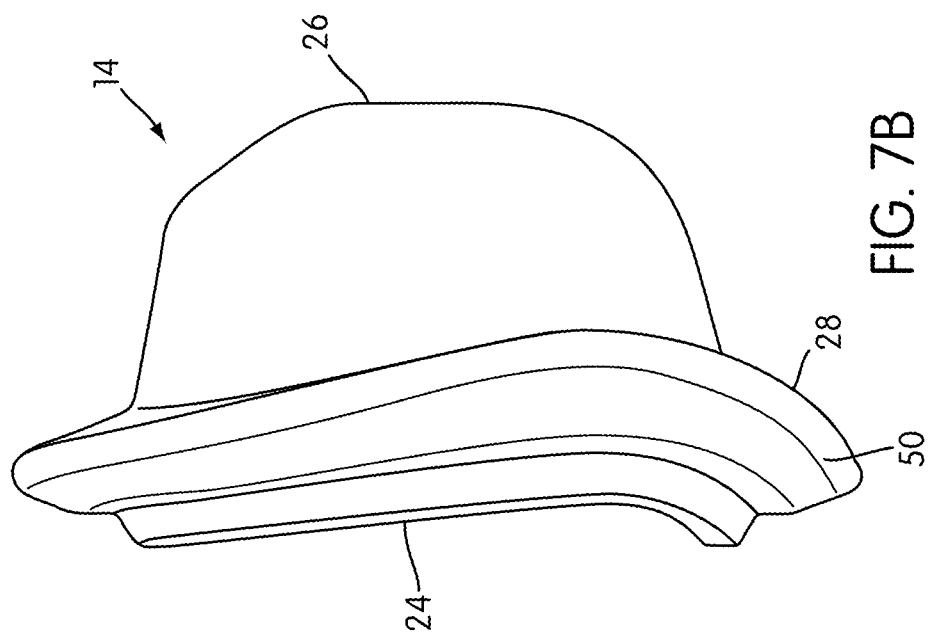
FIG. 7B is a perspective view similar to FIG. 7.
Figure 7:
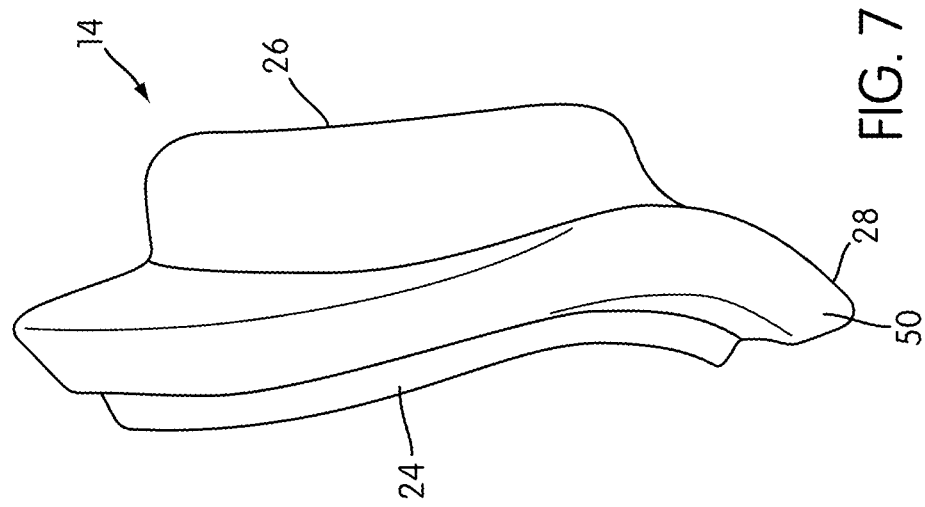
FIG. 7 is a side view of the cushion shown in FIG. 1.
Figure 8B:
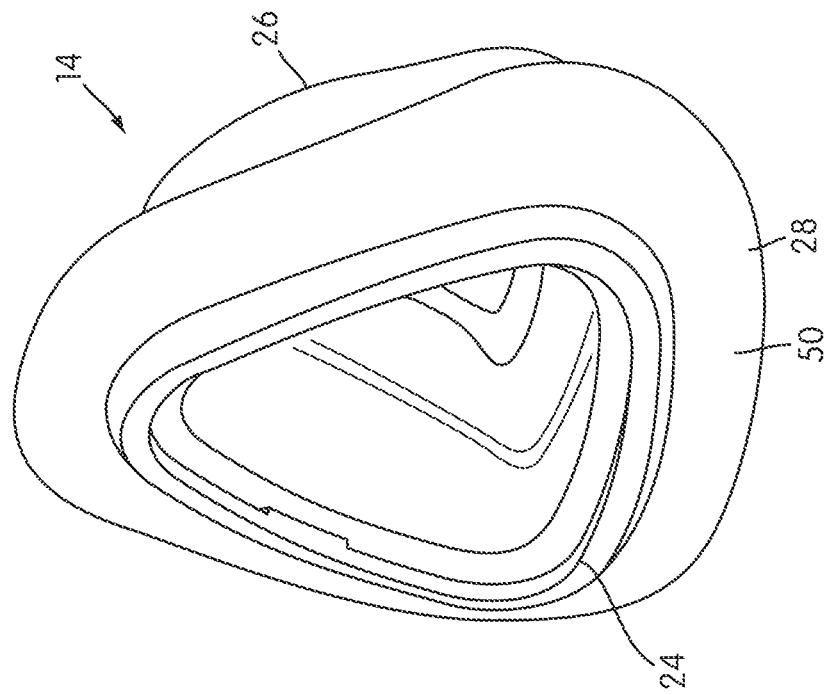
FIG. 8B is a perspective view similar to FIG. 8.
Figure 8:
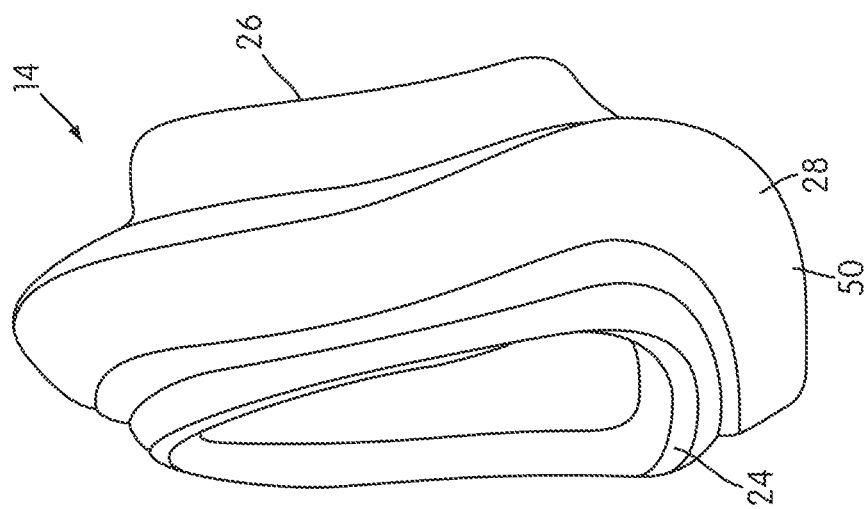
FIG. 8 is a perspective view of the cushion shown in FIG. 1.
Figure 9:
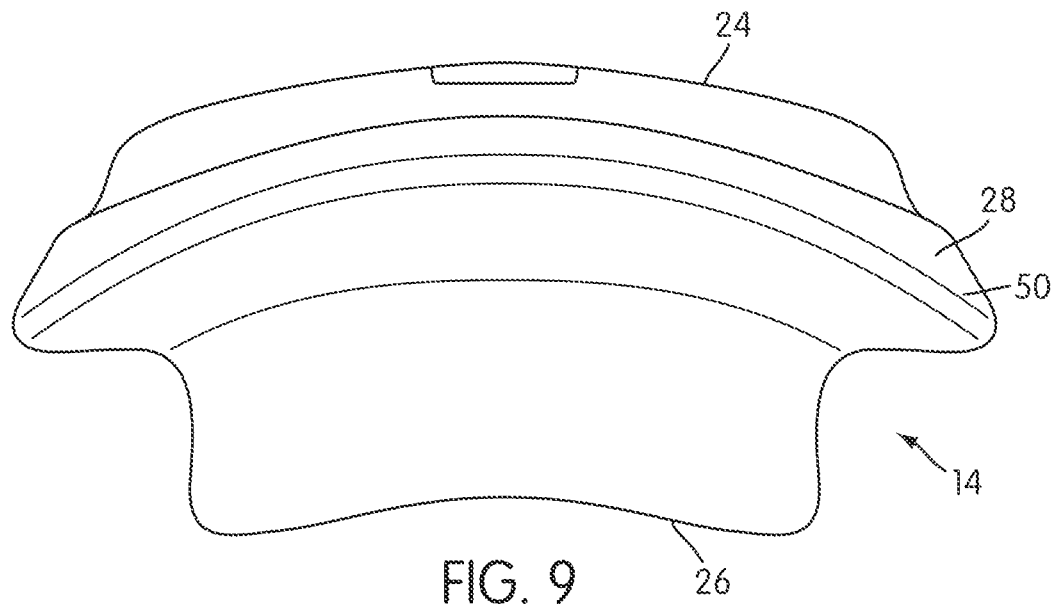
FIG. 9 is a bottom view of the cushion shown in FIG. 1.
Figure 9B:
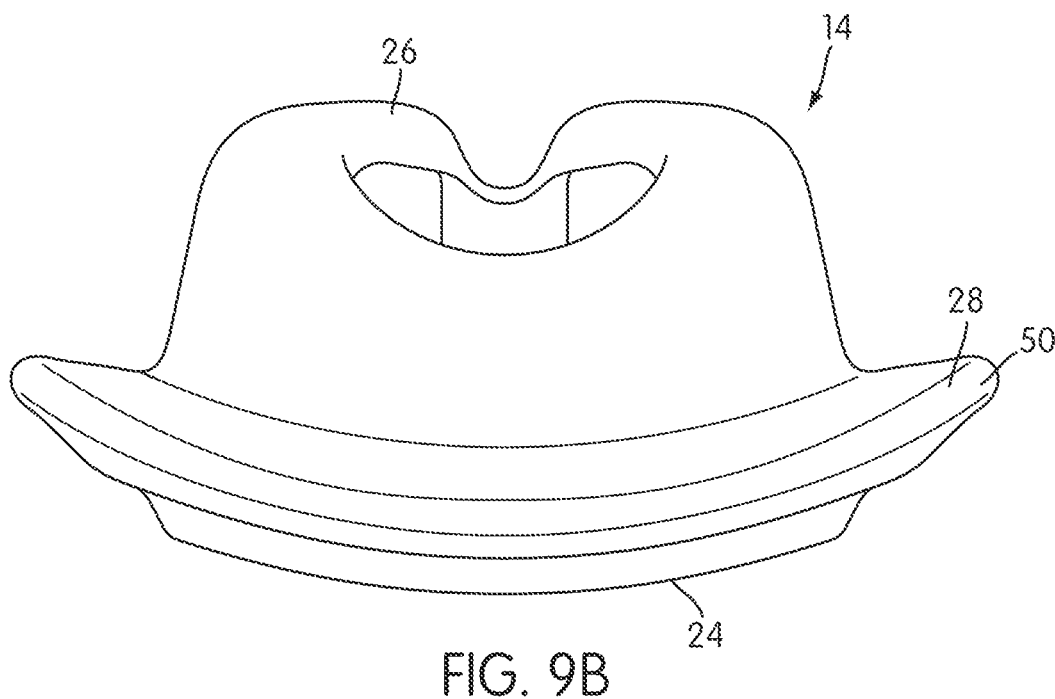
FIG. 9B is a perspective view similar to FIG. 9.
Figure 15:
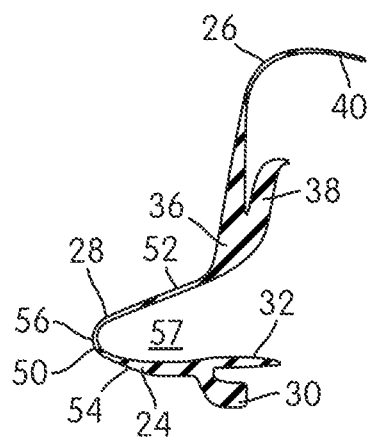
FIG. 15 is a cross-section taken along line 15-15 of FIG. 14.
Figure 16:
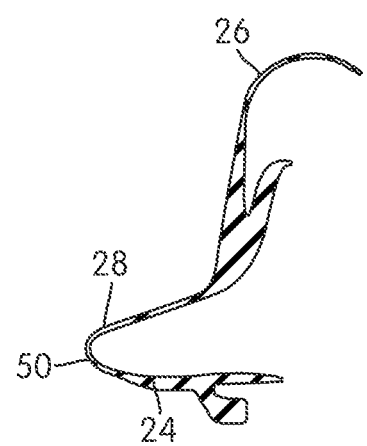
FIG. 16 is a cross-section taken along line 16-16 of FIG. 14.
Figure 17:
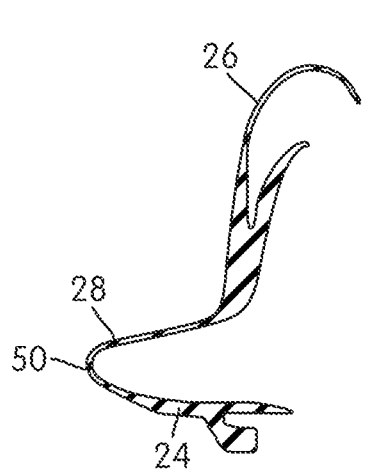
FIG. 17 is a cross-section taken along line 17-17 of FIG. 14.
Figure 18:
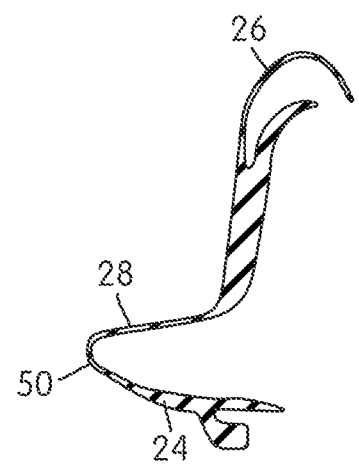
FIG. 18 is a cross-section taken along line 18-18 of FIG. 14.
Figure 19:
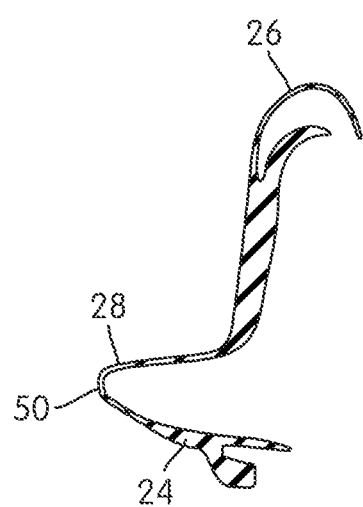
FIG. 19 is a cross-section taken along line 19-19 of FIG. 14.
Figure 20:
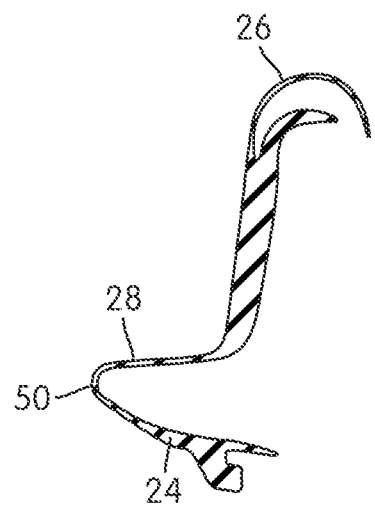
FIG. 20 is a cross-section taken along line 20-20 of FIG. 14.
Figure 21:
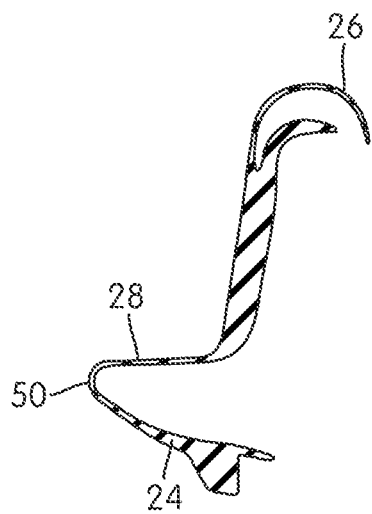
FIG. 21 is a cross-section taken along line 21-21 of FIG. 14.
Figure 22:
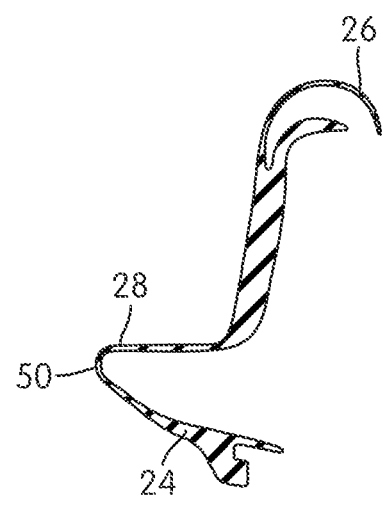
FIG. 22 is a cross-section taken along line 22-22 of FIG. 14.
Figure 23:
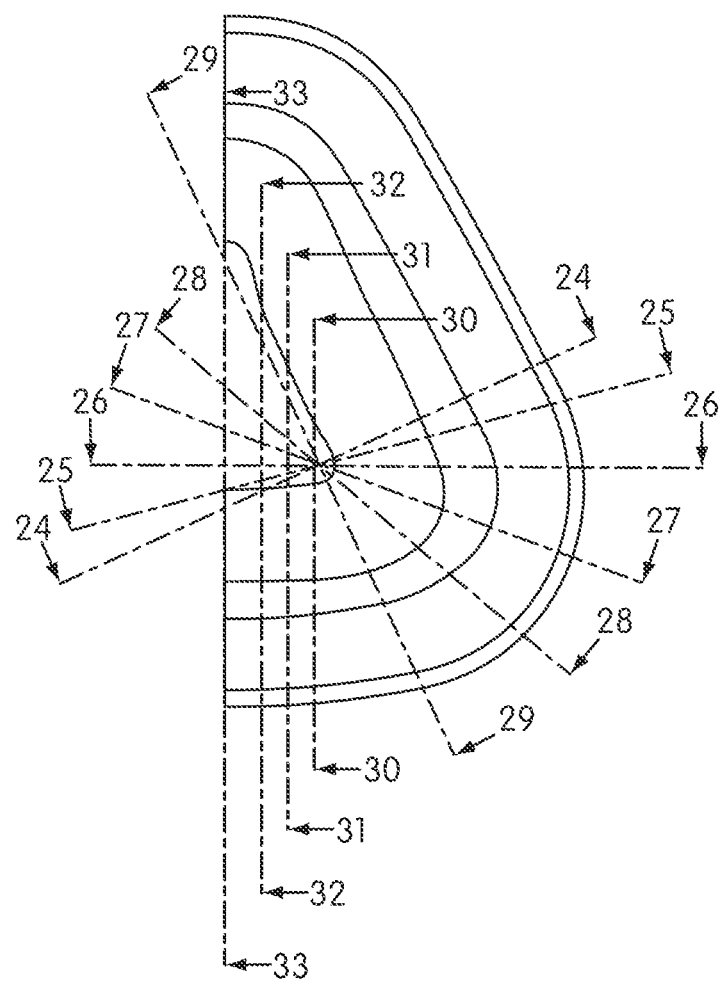
FIG. 23 is a partial top view illustrating an embodiment of the cushion shown in FIG. 1.
Figure 24:
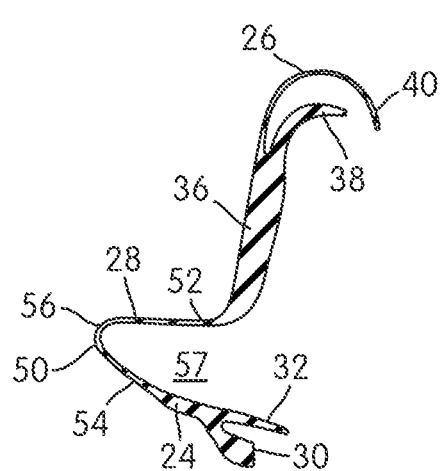
FIG. 24 is a cross-section taken along line 24-24 of FIG. 23.
Figure 25:
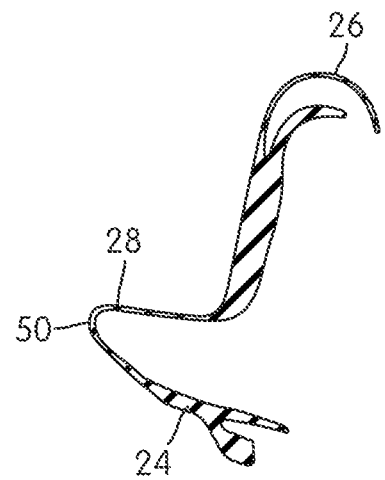
FIG. 25 is a cross-section taken along line 25-25 of FIG. 23.
Figure 26:
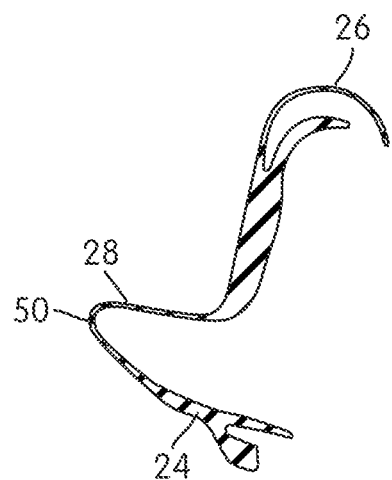
FIG. 26 is a cross-section taken along line 26-26 of FIG. 23.
Figure 27:
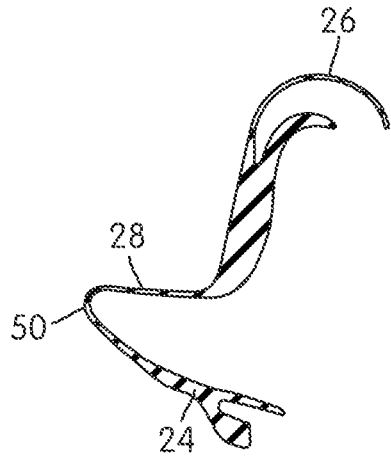
FIG. 27 is a cross-section taken along line 27-27 of FIG. 23.
Figure 28:
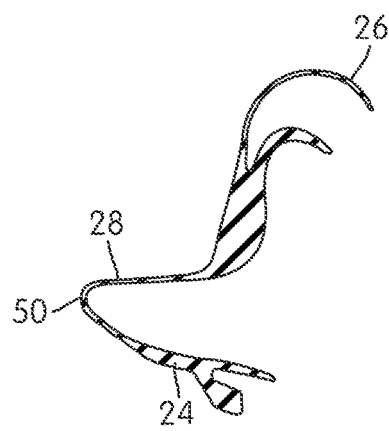
FIG. 28 is a cross-section taken along line 28-28 of FIG. 23.
Figure 29:
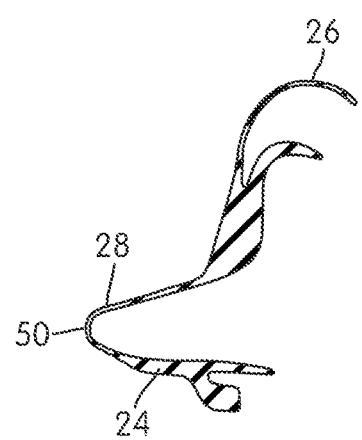
FIG. 29 is a cross-section taken along line 29-29 of FIG. 23.
Figure 30:
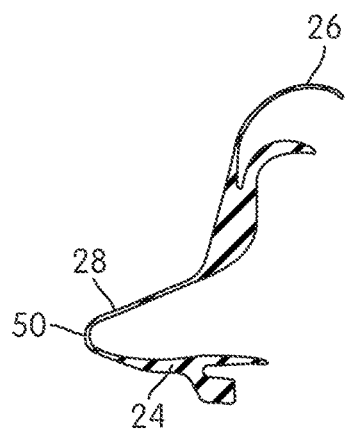
FIG. 30 is a cross-section taken along line 30-30 of FIG. 23.
Figure 31:
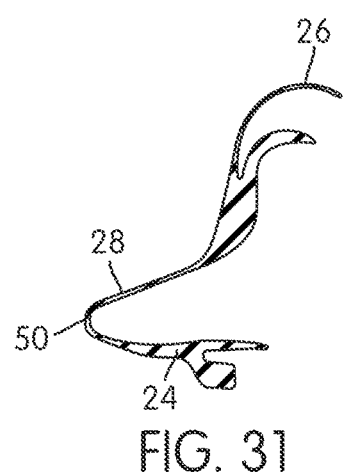
FIG. 31 is a cross-section taken along line 31-31 of FIG. 23.
Figure 32:
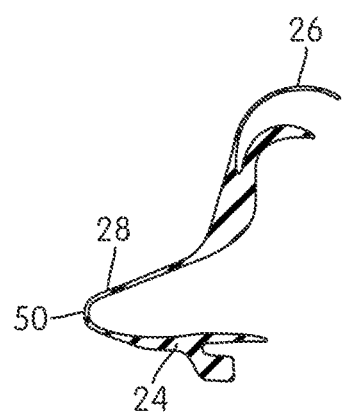
FIG. 32 is a cross-section taken along line 32-32 of FIG. 23.
Figure 33:
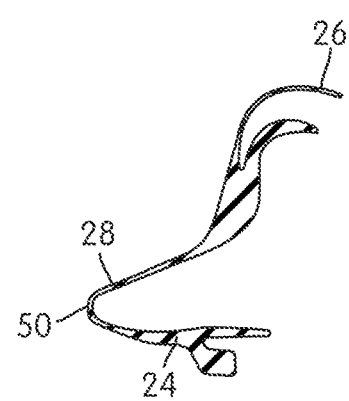
FIG. 33 is a cross-section taken along line 33-33 of FIG. 23.
Figure 34:
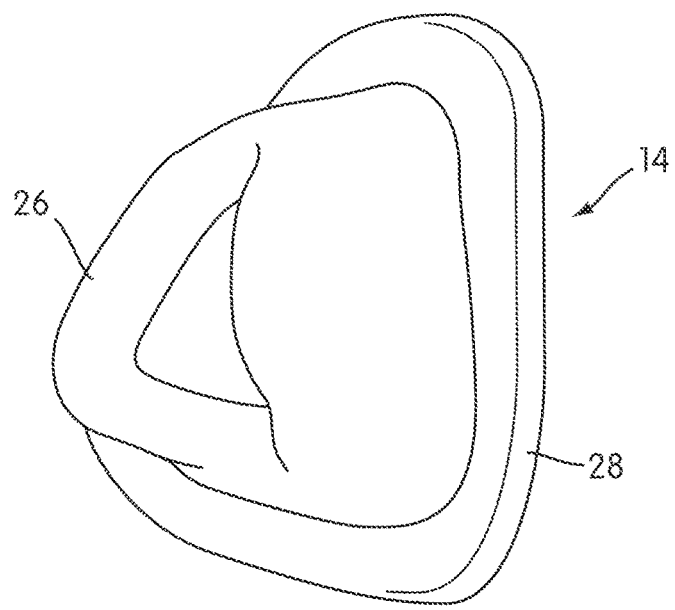
FIG. 34 is a front perspective view of an embodiment of the cushion shown in FIG. 1.
Figure 35:
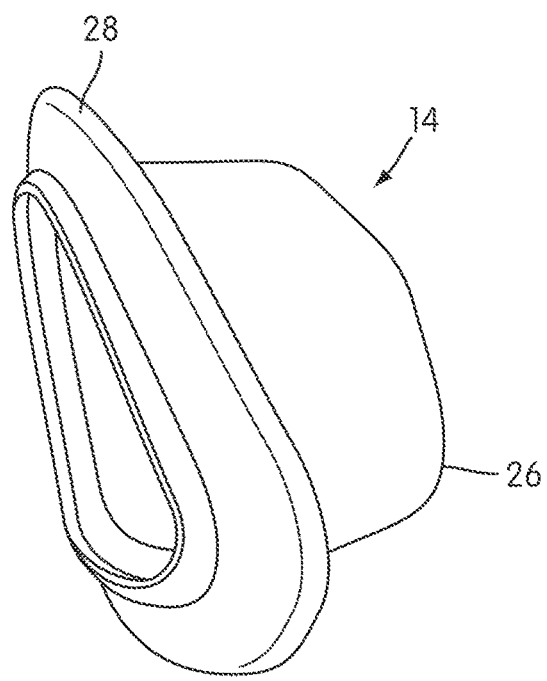
FIG. 35 is a rear perspective view of the cushion shown in FIG. 34.
Figure 36:
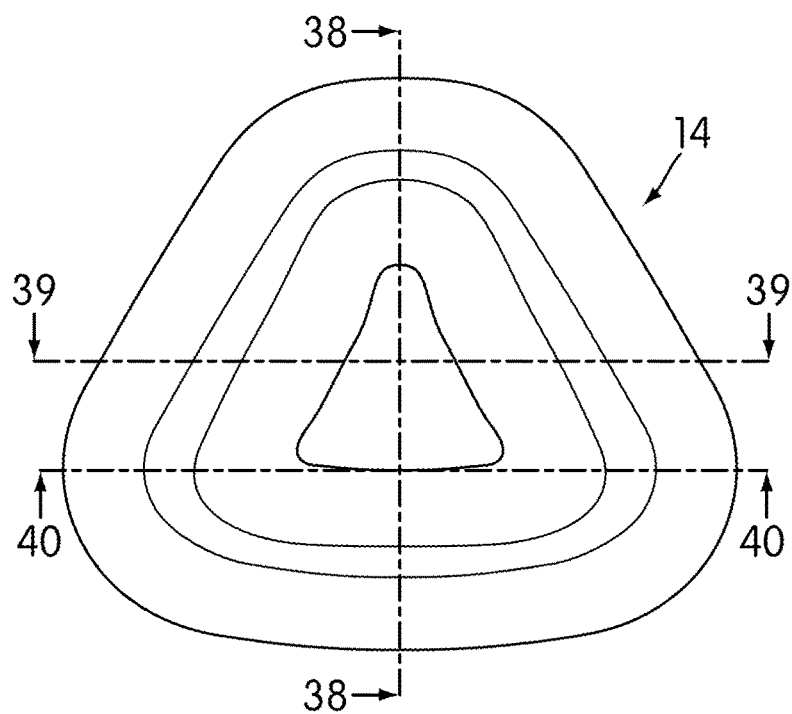
FIG. 36 is a top view of the cushion shown in FIG. 34.
Figure 37:
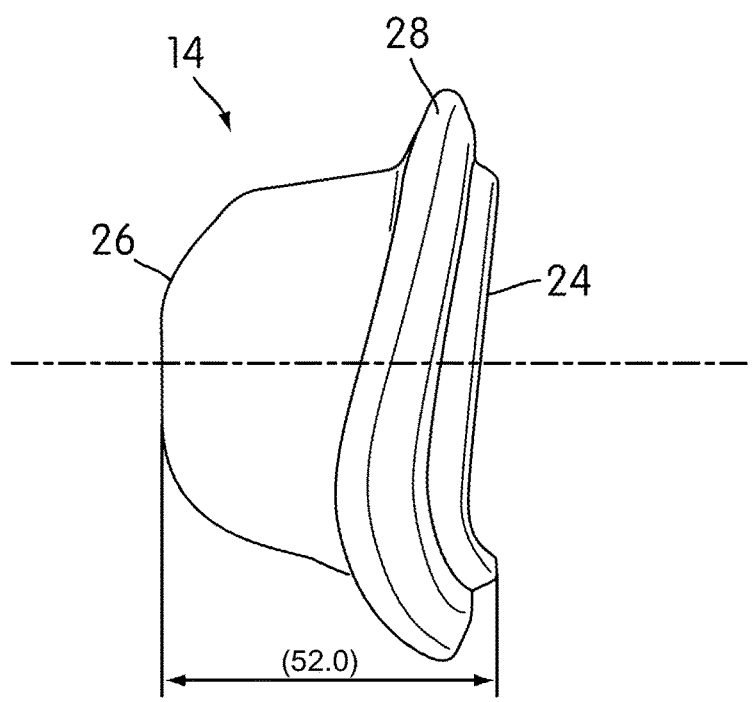
FIG. 37 is a side view of the cushion shown in FIG. 34.
Figure 38:
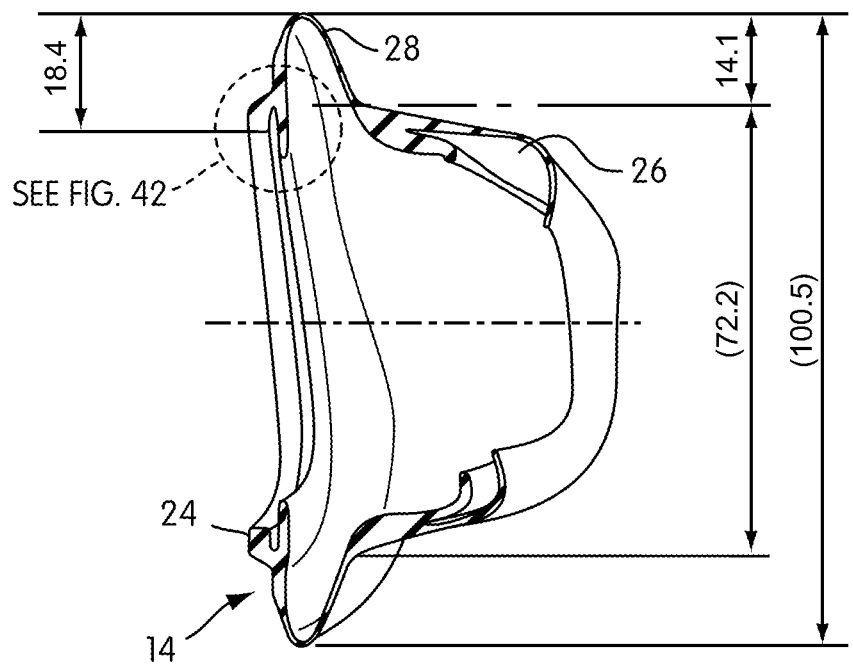
FIG. 38 is a cross-section taken along line 38-38 of FIG. 36.
Figure 39:
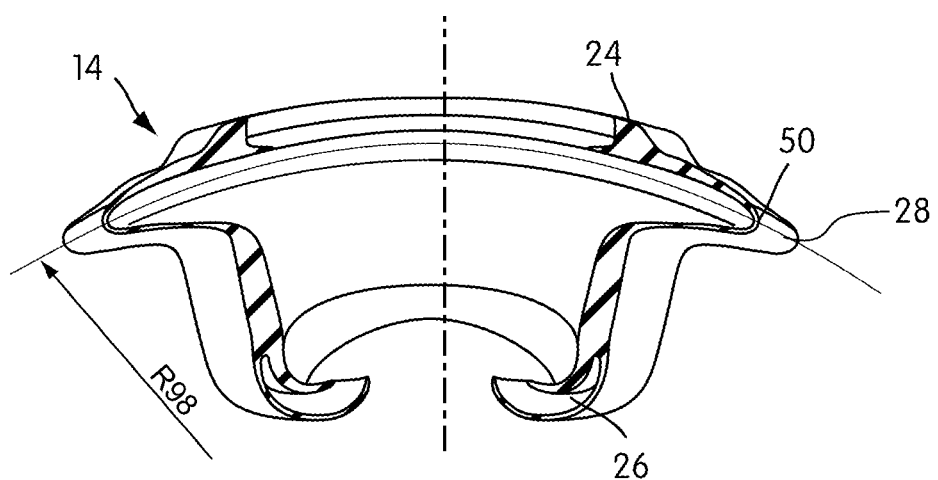
FIG. 39 is a cross-section taken along line 39-39 of FIG. 36.

As shown in FIGS. 6, 6C, and 15, the gusset portion 50 extends outwardly from the side wall 36 of the face-contacting portion 26 and curves back inwardly into the flange 32 of the non-face-contacting portion 24. Specifically, the gusset portion 50 includes a first side wall 52 extending outwardly from the side wall 36 of the face-contacting portion 26, a second side wall 54 extending outwardly from the flange 32 of the non-face-contacting portion 24, and an arcuate wall 56 that interconnects the first and second side walls 52, 54. The walls 52, 54, and 56 of the gusset portion 50 defines a space 57 therebetween. Thus, the gusset portion 50 is curved as viewed from above to follow the contour of the patient's face. As shown in FIG. 39, for example, the gusset portion has a radius of curvature in the range of 80-120 mm, preferably in the range of 95-105 mm.

Figure 10B:
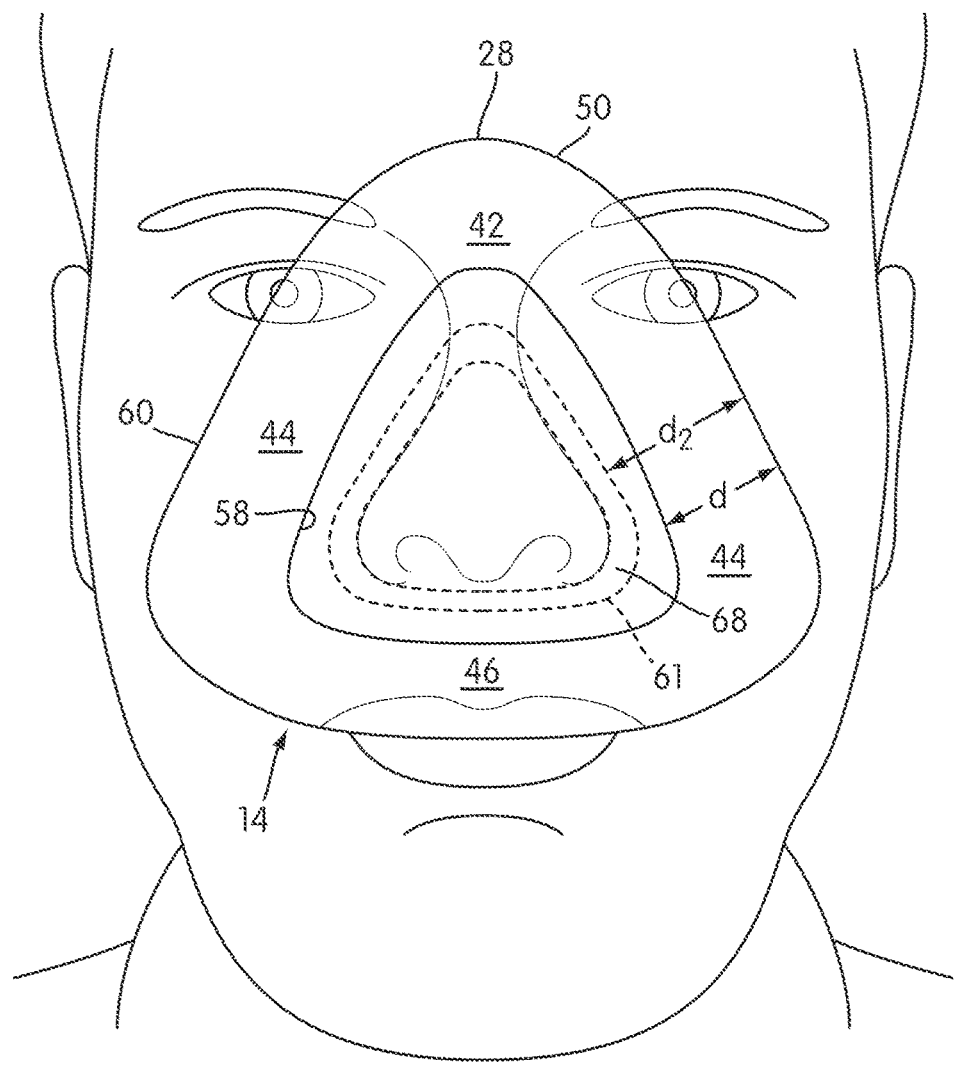
FIG. 10B is a front view of a gusset portion of the cushion shown in FIG. 1 superimposed on a patient's face, the contact line of the membrane on the patient's face shown in dashed lines.
Figure 11B:
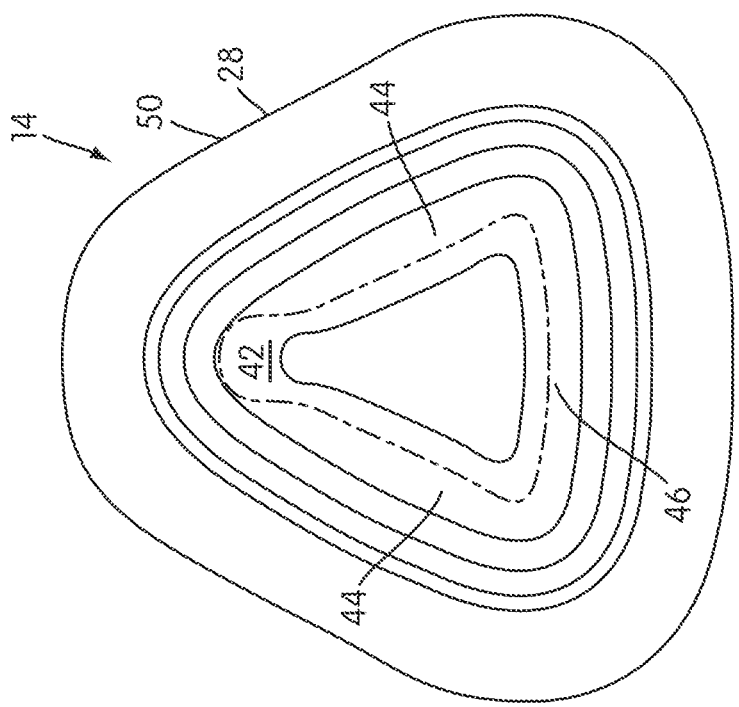
FIG. 11B is a perspective view similar to FIG. 11.
Figure 11:
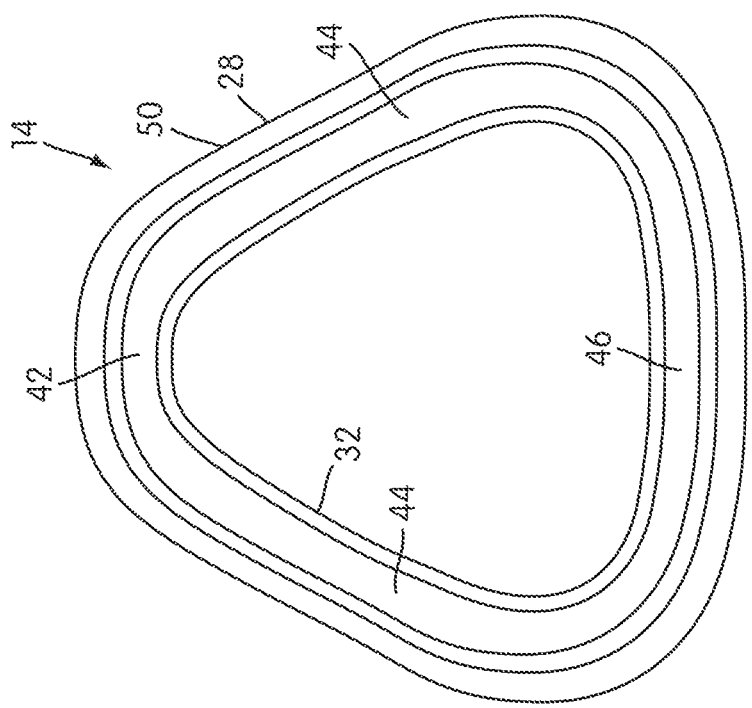
FIG. 11 is a front view of a gusset portion of the cushion shown in FIG. 1.

The gusset portion 50 has an inner edge 58 and an outer edge 60. The inner edge 58 corresponds to an outer edge of the side wall 36 and the outer edge 60 corresponds to an apex of the arcuate wall 56 of the gusset portion 50. A perpendicular distance d is defined between the inner and outer edges 58, 60, as shown in FIGS. 6 and 10. The distance d may be varied to vary the pressure applied by the cushion 14 on the patient's face. The distance $d_2$ is defined as shown in FIG. 10B to be the perpendicular distance between the outer edge 60 and a cushion contact line 61 on the face. The contact line 61 is the outer perimeter of the seal-forming portion 68, that is, the sealing strip of the cushion 14. The additional area between the contact line 61 and the outer edge 60 leads to an additional force on the membrane 40. The contact force on the patient's face is proportional to the pressure in the mask cavity and the footprint area of the gusset portion 50. Thus, the additional area of the gusset portion 50 may be varied, e.g., by varying the distance d, to vary the contact force applied to the patient's face.

An aspect of the invention is that the contact force is controllably distributed around the patient's face. The pressures and forces should be distributed while maintaining the cushion's seal. It is desirable to avoid localized pressure points along sensitive regions of the patient's face. For example, localized points of contact force should be avoided in the nasal bridge region to increase comfort to the patient.

Figure 12:
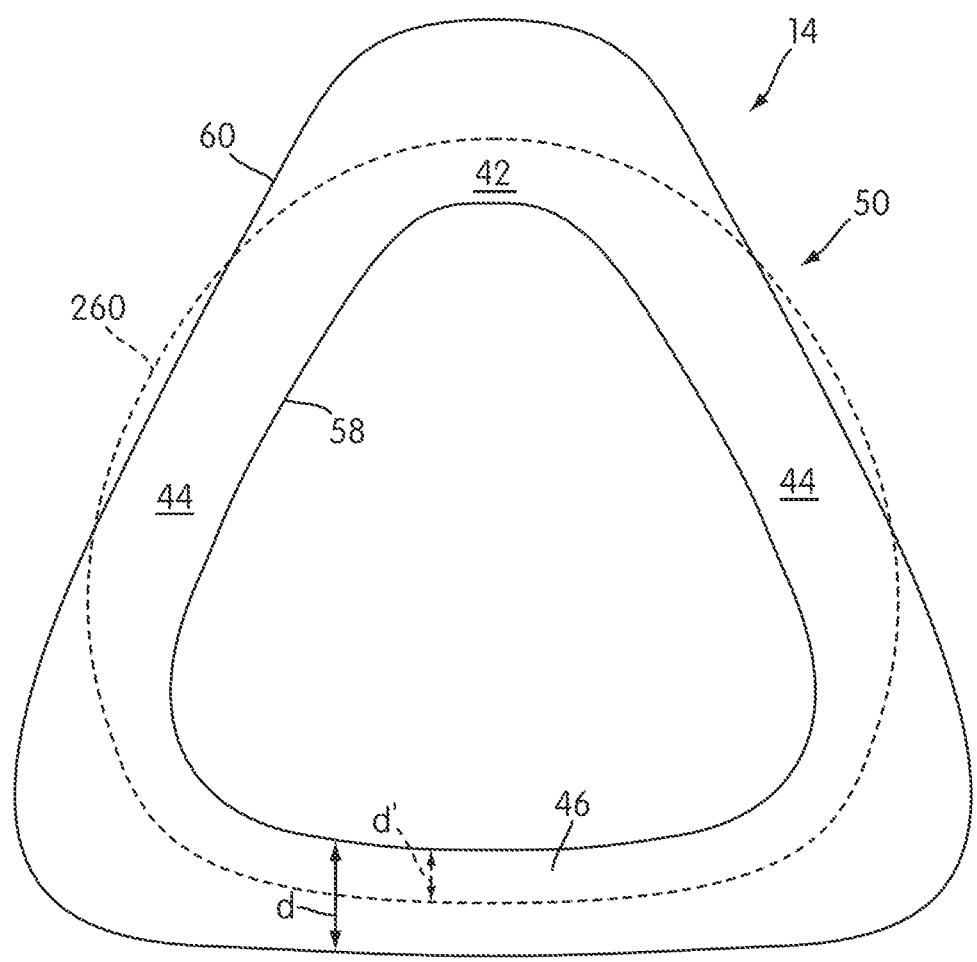
FIG. 12 is a front view illustrating different embodiments of a gusset portion of the cushion shown in FIG. 1.
Figure 12C:
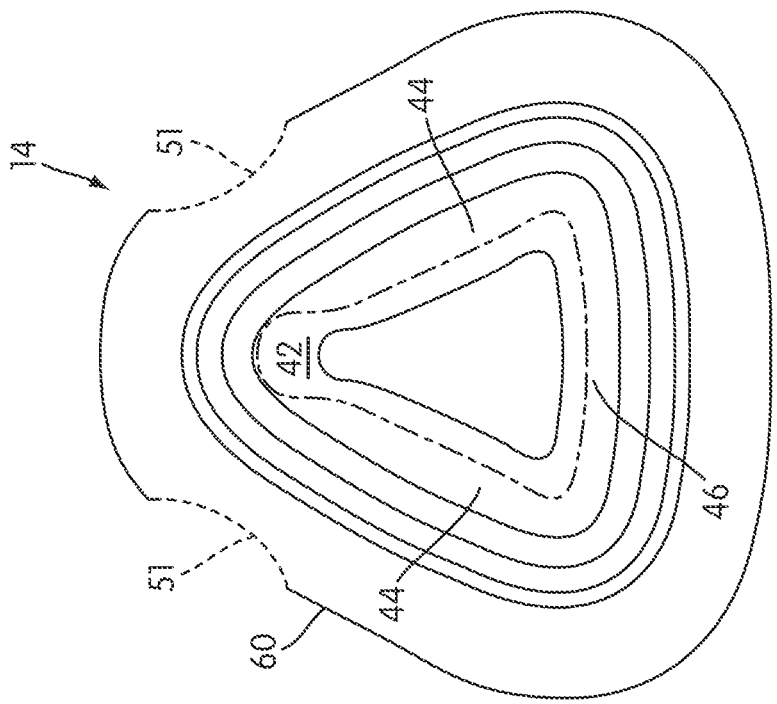
FIG. 12C is a front view similar to FIG. 12 illustrating a different embodiment of a gusset portion of the cushion shown in FIG. 1.

Another aspect of the invention is that not only can the contact force be redistributed while maintaining the cushion seal, but also the patient's field of view can be optimized by reshaping the gusset area around the eyes. For example, as shown in FIG. 12C, the gusset portion 50 has cutaway portions 51 around the eyes to improve the patient's field of view.

Since the contact force applied to the patient's face is proportional to the footprint area of the gusset portion 50, it is possible to vary the force applied to different regions of the patient's face by varying the distance d in different regions of the gusset portion 50. For example, FIG. 12 shows a gusset portion 50 with two possible outer edges. A first outer edge 60, shown in a solid line, has an approximately constant distance d between the inner and outer edges 58, 60. In contrast, the second outer edge 260, shown in dashed lines, has a smaller distance d' in the lip and nasal bridge regions in comparison to the cheek regions.

The gusset portion 50 can be provided in only selected regions of the face, and not others. It need not be provided along the entire perimeter of the cushion. For example, the gusset portion 50 could be provided along only the lip portion.

Thus, the gusset portion 50 with the outer edge 260 in dashed lines has a smaller contact force applied to the nasal bridge and lip regions of the patient's face than the gusset portion 50 with the outer edge 60 in a solid line. In this way, the contact force applied to the patient's face can be redistributed away from more sensitive areas of the patient's face, e.g., nasal bridge and lip region, and applied to less sensitive areas of the patient's face, e.g., cheek regions. Since the nasal bridge region of the patient's face is particularly sensitive, a gusset portion 50 with a reduced area in the nasal bridge region 42 should be more comfortable for the patient. However, the distance d can be tailored for any region of the gusset portion 50 to tailor the force applied to any region of the patient's face for maximum comfort. This can be done on a customized basis to get both an ideal force and a customized area around the cushion.

Figure 12B:
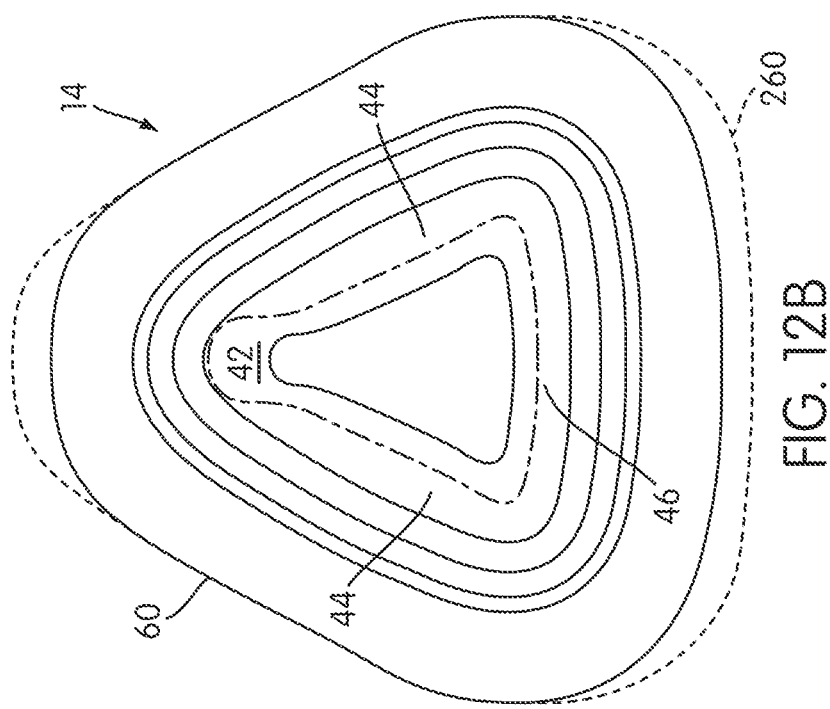
FIG. 12B is a front view similar to FIG. 12 illustrating different embodiments of a gusset portion of the cushion shown in FIG. 1.

FIG. 12B shows another embodiment of a gusset portion 50 with two possible outer edges. A first outer edge 60, shown in a solid line, has a smaller distance between the outer edge 260 and an inner edge (not shown) in the lip and nasal bridge regions in comparison to the cheek regions. In contrast, the second outer edge 260, shown in dashed lines, has an approximately constant distance between the outer edge 60 and an inner edge.

Figure 13A:
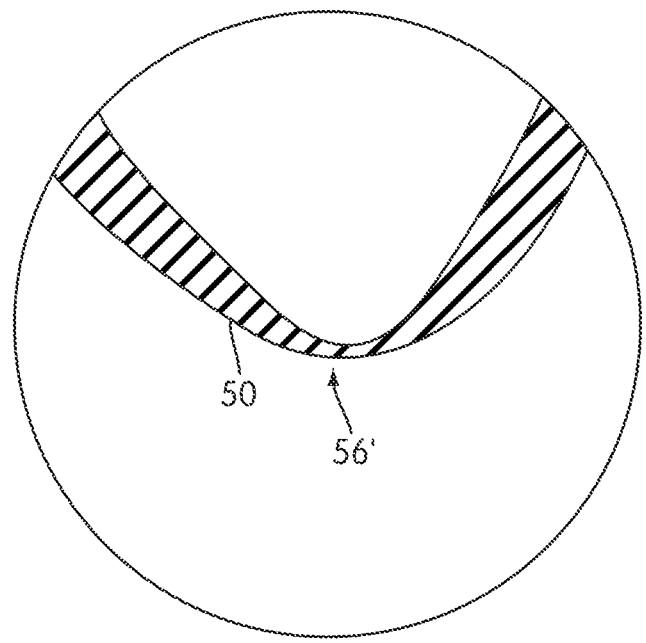
FIGS. 13A-13C are cross-sectional views illustrating different embodiments of a spring structure within a gusset portion of the cushion shown in FIG. 1.
Figure 13B:
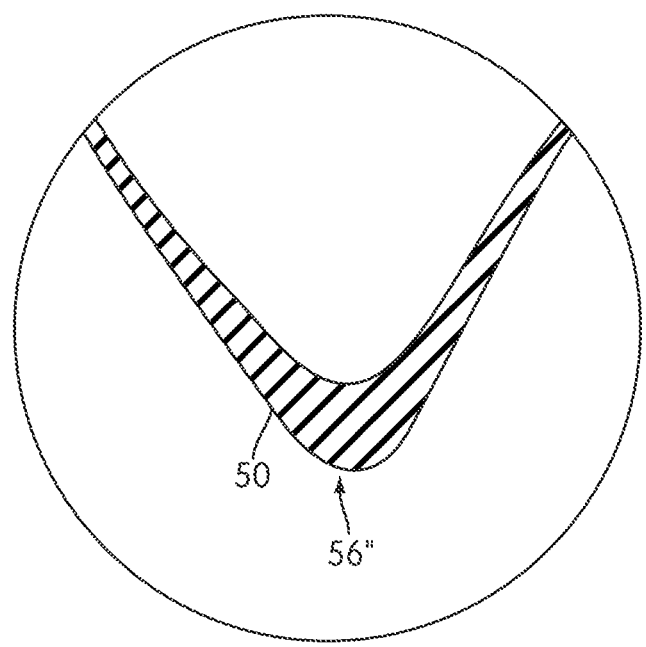

The contact force applied to the contact line on the patient's face can be further tailored by adjusting a thickness of the arcuate wall 56 of the gusset portion, as shown in FIGS. 6, 6C, and 13A-C. The arcuate wall 56 acts as a spring structure to provide a component of the contact force on the patient's face through the membrane 40. The arcuate wall 56' may have a uniform wall thickness or a thin cross-section as shown in FIG. 13A or the arcuate wall 56" may have a thicker cross-section as shown in FIG. 13B, with the thinner arcuate wall 56' providing a smaller component of force than the thicker arcuate wall 56". The cross-section of the arcuate wall 56, 56', 56", 56''' may vary around the perimeter of the gusset portion 50. For example, a gusset portion may have a thin walled arcuate wall in the patient's nasal bridge region, but a thicker walled arcuate wall in the patient's cheek region. Moreover, the arcuate wall may be varied in conjunction with the varying distance d, for example, by reducing the distance d but increasing the thickness of the arcuate wall.

Alternatively, the whole gusset portion 50 may be tapered, not just the arcuate wall.

Figure 13C:
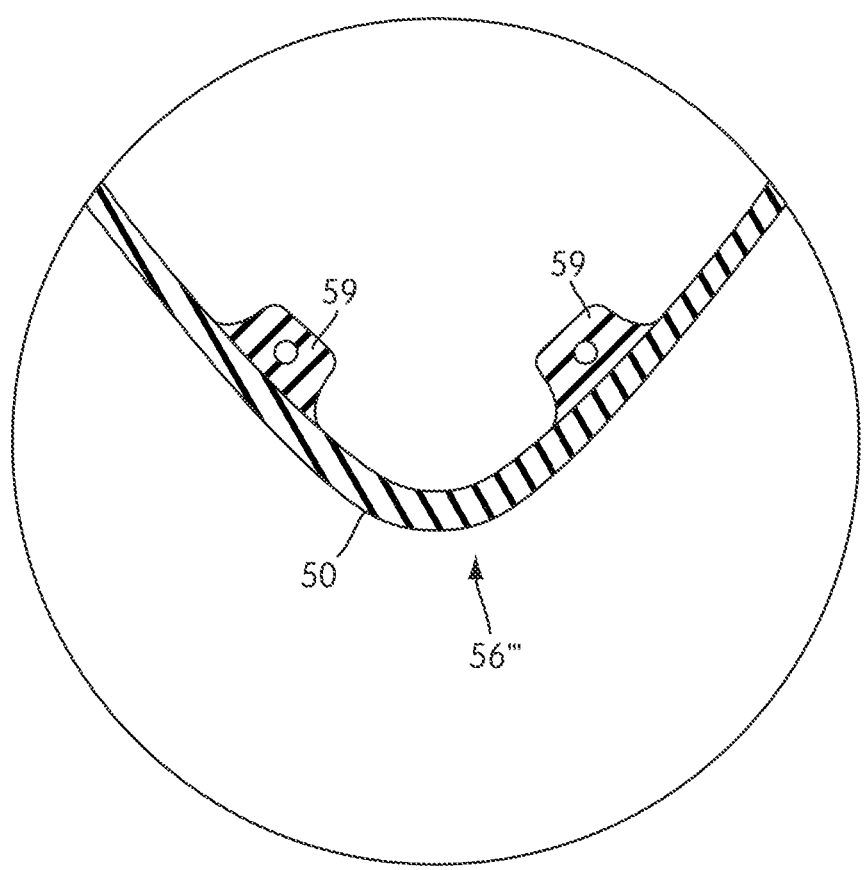
Figure 14:
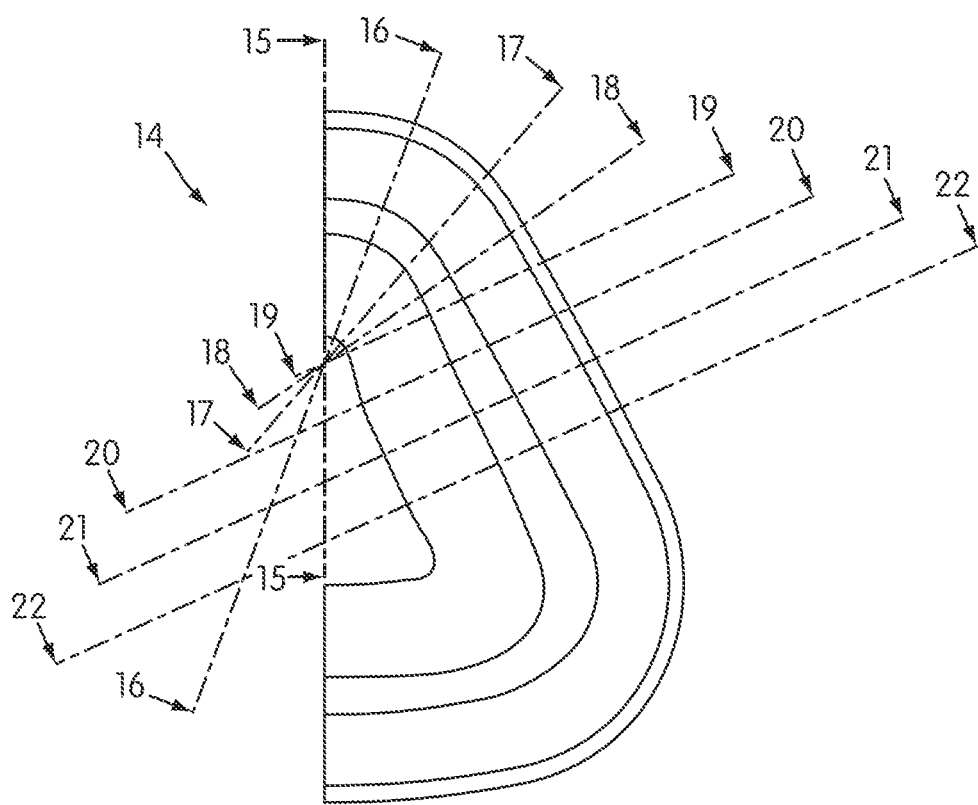
FIG. 14 is a partial top view illustrating an embodiment of the cushion shown in FIG. 1.

The contact force applied to the contact line on the patient's face can be further tailored by providing internal stop structures 59 as shown in FIG. 13C at the gusset portion 50. The size, shape and geometry of these stop structures 59 can be arranged to vary stiffness in different sections of the gusset portion 50. For example, less stiff sections at nasal bridge region, stiffer sections at cheek region, to provide the required comfort and seal level.

In another form, the contact force applied to the contact line on the patient's face can be tailored by inserting a spring (e.g. a steel spring) in the gusset portion 50. The spring has a spring constant that is designed to allow adjustment of the component of force applied by the spring.

In these ways, the contact force on the contact line of the face is not solely a function of mask pressure, but can also, for example, be a function of the spring element within the gusset portion 50. This improves low pressure stability, reduces the sealing force at high pressure, and reduces the visual impact a large gusset portion might otherwise have.

In the illustrated embodiment, the gusset portion 50 as well as the non-face-contacting and face-contacting portions 24, 26 of the cushion 14 have a generally triangular shape. However, the gusset portion 50 and non-face-contacting and face-contacting portions 24, 26 of the cushion 14 may have any suitable shape, e.g., non-triangular shape. Further, the shape of the gusset portion 50 and non-face-contacting and face-contacting portions 24, 26 may be similar to one another or may be different from one another, e.g., the gusset portion has a triangular shape and the face-contacting and non-face-contacting portions have a generally trapezoidal shape.

The cushion 14 is constructed from a soft, flexible skin-compatible material such as silicone. The cushion 14 may be formed, for example, in a one shot injection molding process as is known in the art. However, the cushion 14 may be formed with any suitable material and may be formed by any suitable process. For example, while face contacting portion 26 of cushion 14 may have a softer grade material, the gusset portion may have a harder grade material to provide stiffness as a spring element. The non-face contacting portion 24 may have a stiffer grade material so a direct assembly to frame without a cushion clip may be possible.

The cushion 14 provides improved seal stability and comfort over prior art cushions. Specifically, the curvature of the cushion 14 improves stability of the mask assembly generally and the gusset portion improves stability of seal. Changing the distances d and $d_2$ of the gusset portion in different regions of the patient's face improves patient comfort level.

FIGS. 14-33 show various cross-sections of the cushion 14. The various cross-sections illustrate the various distances between the rim and the membrane in different regions of the patient's face. Moreover, the various cross-sections illustrate the various structural configurations and distances d of the gusset portion 50 in different regions of the patient's face.

FIGS. 34-42 shows further structural details and various dimensions in one embodiment of the cushion 14. For example, the cushion 14 has a length in the range of 42-62 mm, preferably 52 mm, a height in the range of 90-110, preferably 100.5 mm, and a width in the range of 95-115 mm, preferably 103.2 mm. In an embodiment of the cushion 14, the dimensions illustrated in FIGS. 34-42 may vary ±62 or 100%.

FIG. 6B shows an alternative embodiment of the invention which includes a reinforcing ring 64 between the gusset portion 50 and face-contacting portion 26 of the cushion 14. In one form, the ring 64 is constructed from a thickened bead of silicone and is molded with the cushion 14. The ring 64 acts as a stiffening hoop reducing the tendency of the cushion 14 to expand at that point when under pressure. In another form, the ring 64 is made from polycarbonate and is overmolded or push-fit.

The face-contacting portion 26 of the cushion 14 has a surface which may be described by a function of at least one parameter, p, varying from 0 to 360 degrees representing angular position. With respect to the nose, the 0 degree position may be defined to be mid-nasal bridge and the nasal septum will occur at 180 degrees. FIGS. 15-22 and 24-33 depict a range of cross-sections cut at different angular positions, and hence different values of the parameter, p.

An advantage of the mask assembly 10 is that the contact force acting through the contact strip can be tailored to provide an acceptable seal at low mask pressures while not being too high at high mask pressures. For example, in a mask assembly having a gusset portion with no spring structure, the contact force might be too low at low mask pressures to provide a seal, forcing designers to increase the gusset area. This additional gusset area in turn would lead to an excessively high contact force at high mask pressures. The combination of a spring structure with a gusset portion means that at low mask pressures, the contact force may be provided by the spring structure, with the gusset portion making little additional contribution. At high mask pressures, the contact force provided by the gusset portion may be much greater than that provided by the spring structure. Thus, the mask assembly 10 provides a means to tailor the contact forces of a mask system over a range of pressures.

In another of the invention, the extensibility of the headgear is changeable. For example, relatively inextensible headgear might be used for low mask pressures, while more extensible headgear may be used for high mask pressures, such as around 20 cm $H_2O$. In one form, this is achieved by having duplicate straps within the headgear, one extensible, the other, relatively inextensible. At low pressures, both straps are used, the net effect being that the headgear is relatively inextensible. At high pressures, the inextensible strap is disengaged, with the result that the headgear is relatively extensible overall.

Figure 43:
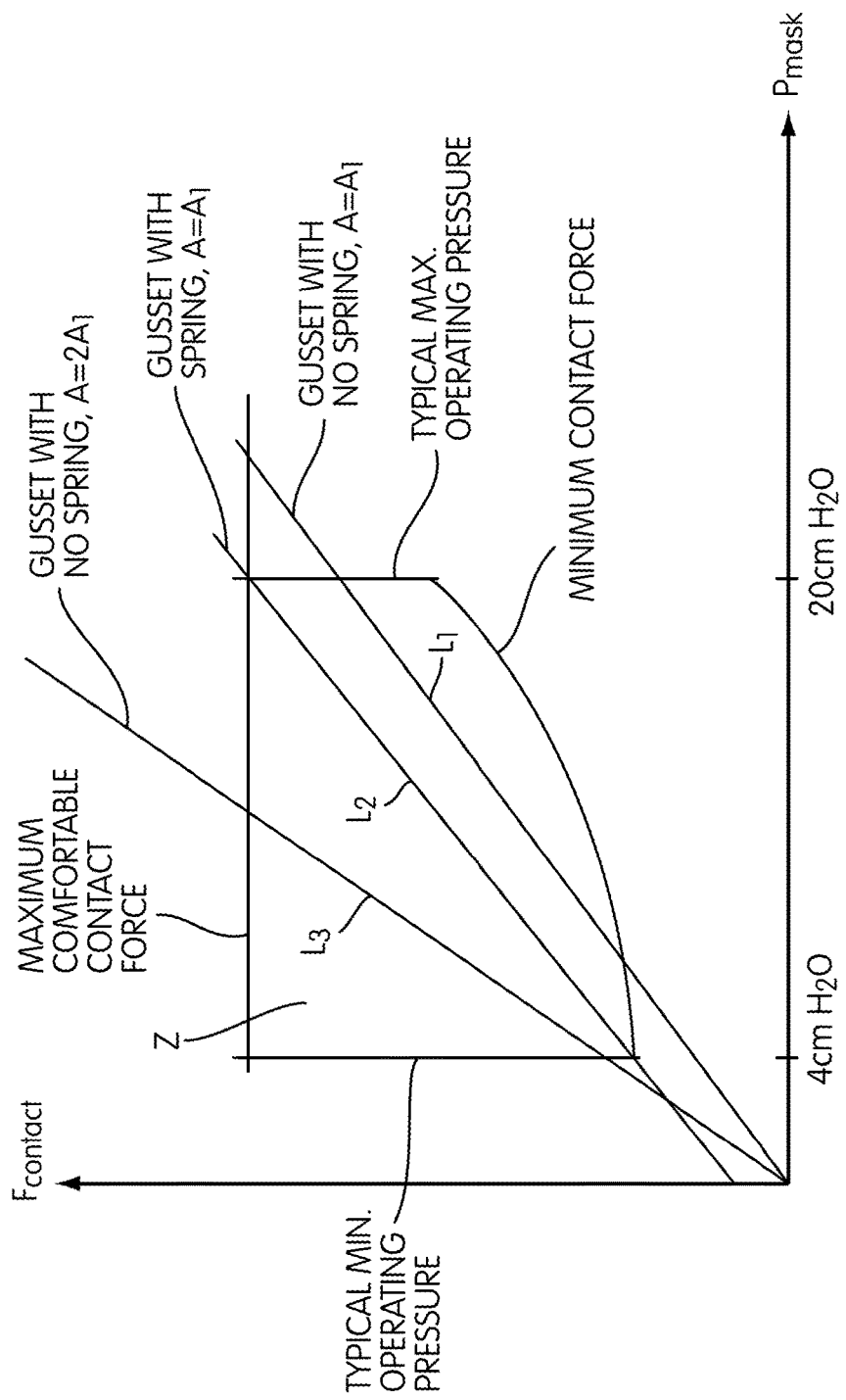
FIG. 43 is a graph that illustrates the relation between mask pressure and contact force on the patient's face for a mask with at least a gusset portion wherein the gusset portion is held at a fixed extension.

FIG. 43 illustrates the contact force on the patient's face for a mask with at least a gusset portion wherein the gusset portion is held at a fixed extension, e.g., expansion. The x-axis is the pressure inside the mask. The y-axis is the contact force on the patient's face. A zone of comfort and seal Z is defined by: (a) a range of typical operating pressures from 4 to 20 cm $H_2O$; (b) a minimum contact force that is required to maintain a seal on a patient's face, the minimum contact force defined as an increasing function of the pressure inside the mask; and (c) a maximum comfortable contact force.

In accordance with an embodiment of the invention, the cushion is designed to include a gusset portion and spring structure such that the contact force applied by the cushion is maintained within the zone of comfort and seal Z.

FIG. 43 shows three lines for three hypothetical cushions with at least a gusset portion. In general, at a first approximation, contact force increases linearly with mask pressure as the result of the additional footprint area provided by the gusset portion.

A first line L1 represents a cushion with a gusset portion which has an additional footprint area of A1 and which does not include a spring structure. As illustrated, the contact force is below the minimum contact force required to make a seal for mask pressures below about 7 cm $H_2O$. Thus, the cushion represented by line L1 falls outside the zone of comfort and seal Z. For higher pressures (e.g., mask pressures above about 7 cm $H_2O$), the contact force from the gusset portion is sufficient to maintain a seal.

A second line L2 represents a cushion according to one embodiment of the invention with a gusset portion which has an additional footprint area of A1 and includes a spring structure. The effect of the spring structure is to provide an additional contact force at low mask pressures when the effect of the gusset portion is insufficient to provide the minimum sealing force. As a result, the cushion maintains a seal through the range of operating pressures. Moreover, the cushion represented by line L2 falls within the zone of comfort and seal Z throughout the range of operating pressures.

A third line L3 represents a cushion with a gusset portion which has an additional footprint area of 2×A1 and does not include a spring structure. The extra footprint area (twice that of the cushions represented by L1 and L2) results in the contact force of the cushion being sufficient to maintain a seal at a low mask pressure of 4 cm $H_2O$. However, for mask pressures above about 10 cm $H_2O$, the contact force exceeds the maximum comfortable contact force. Thus, the cushion represented by line L3 falls outside the zone of comfort and seal Z.

Thus, by combining a gusset portion with a spring structure in a cushion, a designer can tailor the contact force of the cushion such that it falls within the zone of comfort and seal Z throughout the working range of pressure. The same principles may be applied for different pressure ranges.

Further, the size of the zone Z may change (e.g., by changing the maximum comfortable contact force) depending on a particular region of the patient's face. For example, the maximum comfortable contact force may be reduced for a nasal bridge region of the face. As a result, the cushion can be tailored for that particular region such that it falls within the zone of comfort and seal Z throughout the range of operating pressures.

Figure 44:
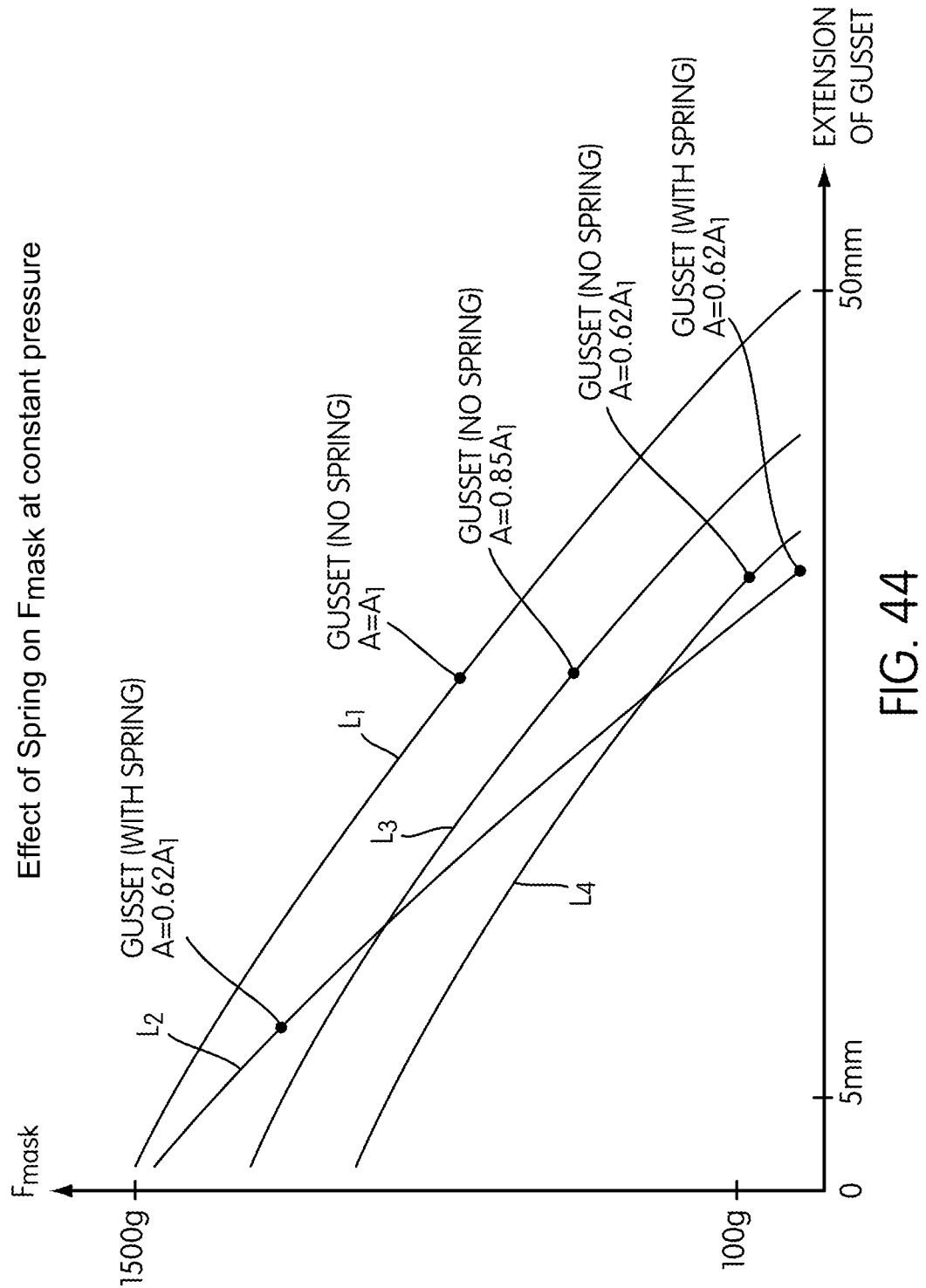
FIG. 44 is a graph that illustrates the effect a spring structure has on the total force applied to the patient's face at a constant mask pressure.

FIG. 44 illustrates the effect a spring structure has on the total force applied to the patient's face at a constant mask pressure. $F_{mask}$ the total force of the mask on a patient's face, as defined in WO 01/97893 (Frater et al.). The inclusion of the gusset portion on the mask allows the two sides of the cushion to travel relative to one another. When the extension or expansion of the gusset portion is 0 mm, the two sides of the cushion abut one another. When the extension of the gusset portion is 50 mm, the two sides of the cushion are 50 mm apart. The closer the two sides of the cushion are brought towards one another, the higher the value of $F_{mask}$.

FIG. 44 shows four lines that represent four different cushions. A first line L1 is for a cushion with a gusset portion with no spring structure and with an additional footprint area of A1. A second line L2 is for a cushion according to one embodiment of the present invention with a gusset portion, a spring structure, and an additional footprint area of 62% of A1. A third line L3 is for a cushion with a gusset portion without a spring structure and with an additional footprint area of 85% of A1. A fourth line L4 is for a cushion with a gusset portion without a spring structure and with an additional footprint area of 62% of A1.

As illustrated, the addition of a spring structure to a cushion having a gusset portion increases $F_{mask}$ generally throughout the range of gusset extensions. As a result, a cushion may be constructed with a gusset portion having a smaller footprint area than would otherwise be required to provide sufficient $F_{mask}$ to maintain a seal.

Further, the effect of the spring on $F_{mask}$ can be determined for various mask pressures so that the cushion can be tailored for particular regions of the patient's face.

Elastic Cuff

Figure 45:
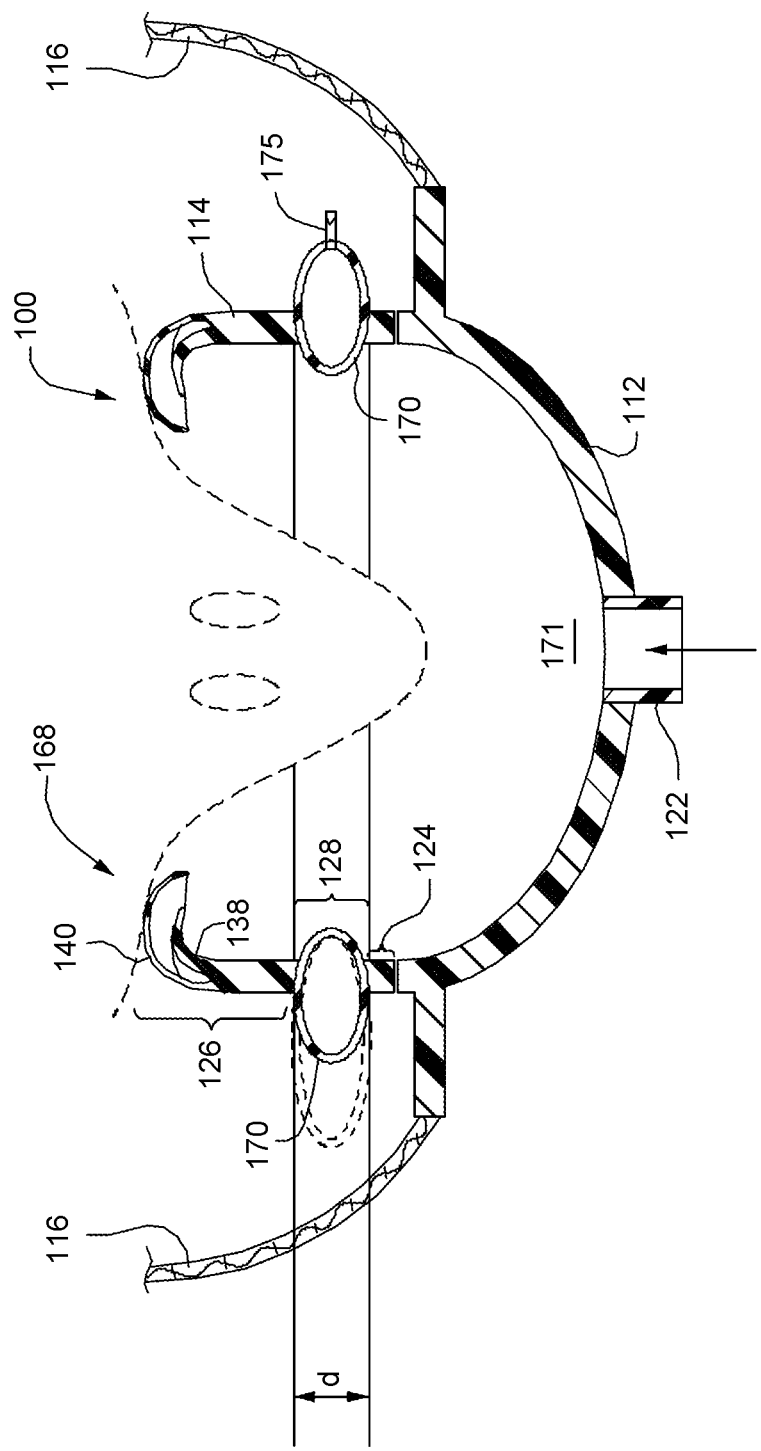
FIG. 45 is a cross-sectional view of another embodiment of the invention including an elastic nasal cuff.

FIGS. 45-49 show an alternative embodiment of the present invention which may be used in conjunction with earlier or later described embodiments. As shown in FIG. 45, a mask assembly 100 includes a mask frame 112, a cushion 114 and a strap 116, all of which can be assembled in a fashion which is similar to that described above in relation to other embodiments.

The frame includes an inlet 122 which is in communication with the source of pressurized air or breathable gas. Preferably, the inlet is connected to a swivel elbow which in turn is connected to an air delivery tube.

The cushion 114 includes a non-contacting portion 124 which is provided to the mask frame 112, as described above. The cushion 114 further includes a face contacting portion 126 and an intermediate portion 128 which is between the non-contacting portion and the face contacting portion 126. The face contacting portion 126 includes a face-contacting seal portion 168 including a membrane 140 and a rim 138, as described above.

The intermediate portion 128 may be provided with at least one cuff 170 that may be resiliently inflatable. The cuff 170 includes walls that can stretch as opposed to being simply flexible. As the straps 116 are tightened, membrane 140 and rim 138 are pushed onto the face. This action causes a force to be applied to the membrane 140, the rim 138 and the face-contacting portion 126, displacing the face contacting portion 126 in the direction of the non-contacting portion 124. The displacement of the face contacting portion 126 and its associated force causes the cuff 170 to balloon outwards. The force is dependent on the degree of strap tightening and the stiffness (force-displacement relationship) of the cuff 170. Initial inflation of the cuff 170 can be achieved via a valve 175. The valve 175 can be in communication with the same source which provides pressurized air to the breathing chamber 171 of the mask assembly 100, or the source can be a separate pressurized source independent of the source for providing pressurized breathable gas to the breathing chamber 171. The elastic cuff 170 can be formed in a single piece with the cushion 114. Alternatively, the elastic cuff 170 may be formed separately from the cushion 114, and later attached, e.g., using adhesives, mechanical fasteners, or the like, etc.

Current mask systems use inflatable cuffs that are relatively stiff being made from materials having a relatively high modulus of elasticity. By contrast the cuffs 170 of the present embodiment are designed to have a relatively low stiffness. This is achieved, e.g., by providing the cuffs 170 with walls that stretch under relatively low forces. Walls with this characteristic typically are made from a material with a relatively low modulus of elasticity. For example, the modulus of elasticity of the material of the elastic cuff material, as determined by bench testing, is in the range of 0.15 MPa to 0.6 MPa. The preferred value for the modulus of elasticity is in the range of 0.25 MPa to 0.45 MPa. In one example, the modulus of elasticity is about 0.35 MPa. In comparison, the gusset portion described above may have a modulus of elasticity of 0.40 MPa to 0.80 MPa, and preferably the modulus of elasticity is about 0.60 MPa. The modulus of elasticity for both the gusset and the elastic cuff 170 can be more or less than that stated above or modified to give the appropriate stretch characteristics in conjunction with the delivered mask pressure and headgear tension/strap displacement.

In the embodiments described above, for example in relation to FIG. 1, a mask system and cushion provided with a gusset produces a number of positive attributes, for example, the ability to maintain cushion seal with relative frame instability, less fine adjustment required of head gear straps to apply a cushion force towards the face to maintain a seal. A cushion provided with the elastic cuff 170 of FIG. 45 also exhibits similar results to the above embodiments. However, the elastic cuff forces are independent of the supply air from the flow generator.

Prior art masks use inflatable (verses elastic) cuffs or pneumatic seals and/or seal rings. These inflatable cuffs are typically made from PVC that has a relatively high modulus of elasticity causing them to be relatively stiff. Bench testing of this PVC material found that the modulus of elasticity was of the order of 5.2 MPa. Although they may include some flexibility, it is not resiliently expandable like the elastic cuff 170 shown in FIG. 45. Examples of inflatable cuffs with a relatively high modulus of elasticity include U.S. Pat. No. 4,971,051 to Toffolon and anesthesia masks available from King Systems.

Figure 46:
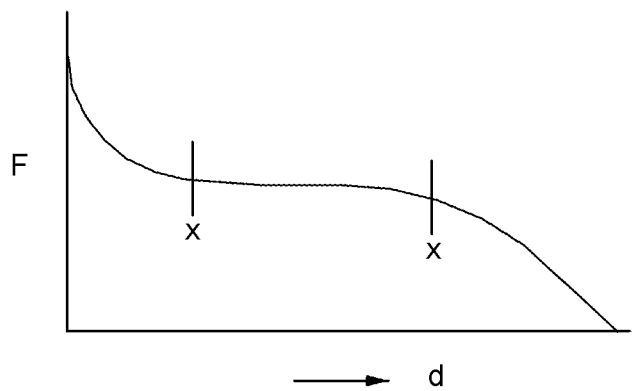
FIG. 46 is a force versus displacement graph for ResMed's Activa™ mask.
Figure 47:
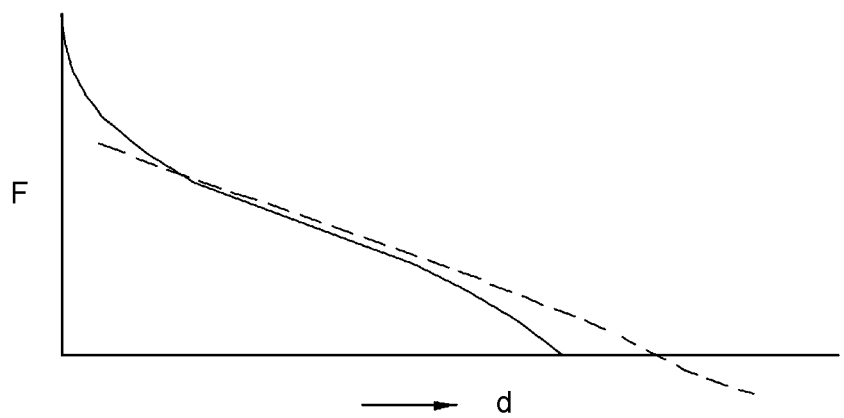
FIG. 47 is a force versus displacement graph for a prior art mask.
Figure 47A:
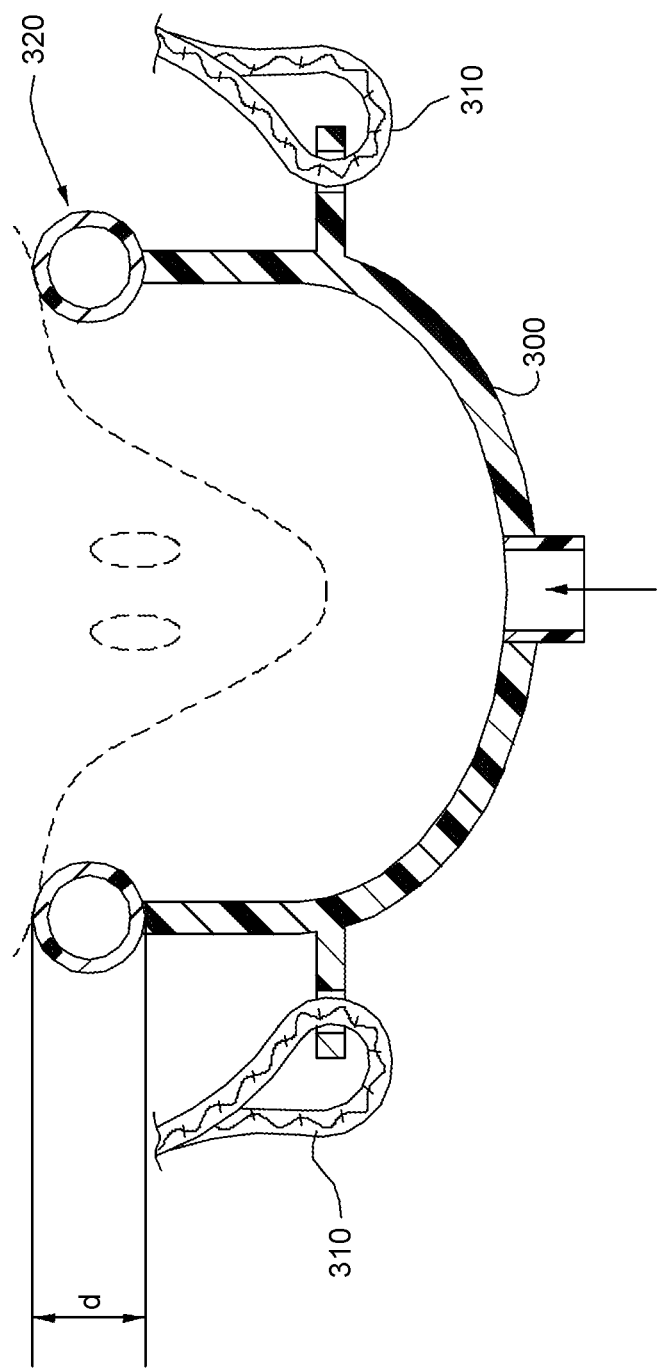
FIG. 47A is a cross-sectional view of a mask according to the prior art.
Figure 48:
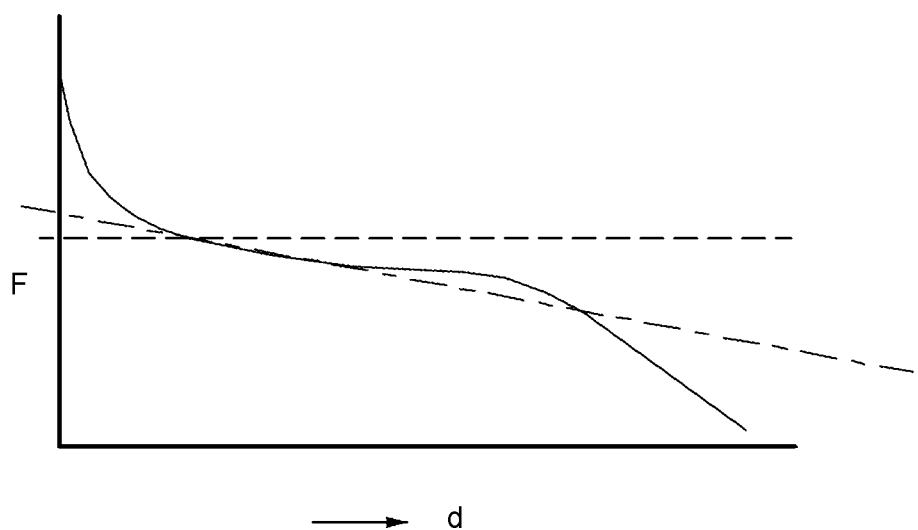
FIG. 48 is a force versus displacement graph for an embodiment of the present invention.
Figure 49:
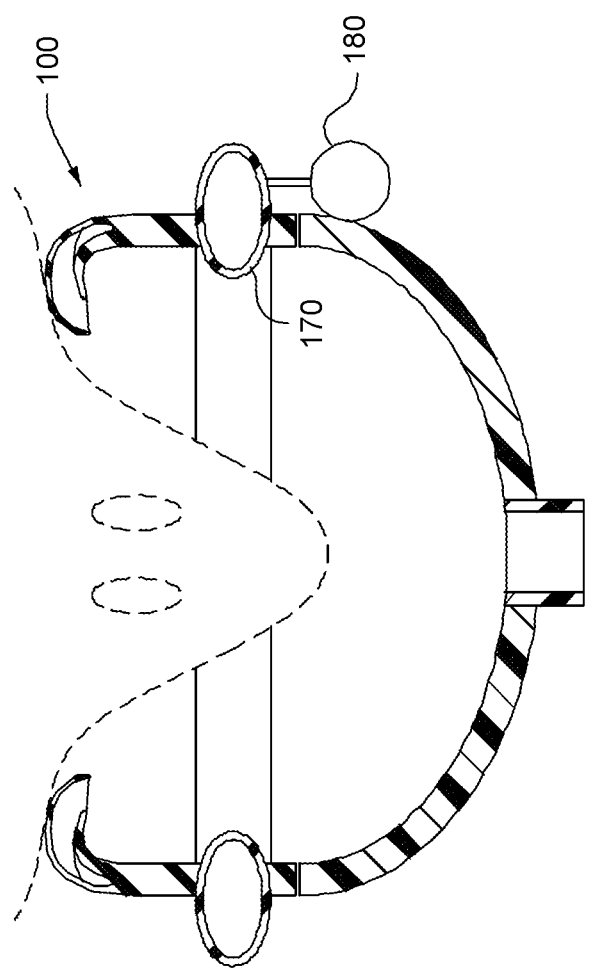
FIG. 49 is a cross-sectional view of yet another nasal cuff embodiment of the present invention.

FIGS. 46-48, respectively, are force-displacement (stiffness) graphs for 1) the embodiment shown above with a gusset (ResMed's Activa™ mask); 2) the Prior Art; and 3) the elastic cuff shown in FIG. 45. It should be noted that the horizontal axis in these graphs labeled 'd' represents the dimension shown as 'd' in FIG. 45 (described above) and FIG. 47A which shows a prior art mask frame 300 with straps 310 and an inflatable cuff 320. As shown in FIG. 46, the flattened region according to the Activa™ mask gives a mask system with greater tolerance to strap tension or mask instability while maintaining relatively constant force of cushion seal to face. See the line between points X-X in FIG. 46.

In contrast, the graph of FIG. 47 shows that the prior art inflatable cuff being made of a material with a relatively higher modulus of elasticity has a more linear force-displacement characteristic and is stiffer. Therefore slight changes in the mask or cushion relative to the face that result in small changes to the dimension 'd' will cause relatively large changes in the sealing force applied to the face. Therefore, this prior art mask system cannot maintain a good seal over increased displacement (due to instability). Strap tension is critical to maintain the tolerable level of comfort.

Therefore, one aspect of this embodiment is to produce an elastic cuff from a material with a relatively low modulus of elasticity, like that of a stretchy balloon. The elastic cuff material has the ability to stretch under standard strap tension experienced in this application.

When the mask is not fitted, the inflatable cuff is not necessarily under pressure. When fitted correctly, the cuff is compressed as the straps are tightened. Given the low modulus of elasticity of the elastic cuff material, the cuff is designed to stretch, billow, bloat and/or swell as the cuff elongates as shown in phantom in FIG. 45.

The force applied to the cushion seal could be fine tuned by modifying the stiffness of the cuff walls, e.g., increasing or decreasing the modulus of elasticity, or by pre-pressurizing the elastic cuff 170 via a valve that, in this example, would increase cushion seal forces when the cushion is displaced and/or fitted into position and the straps tensioned.

As shown in FIG. 48, the elastic cuff 170 is made from a material with a lower modulus of elasticity that produces a similar flattened line to that shown in FIG. 46. However, this graph is slightly angled as compared to FIG. 46, but it is flatter than that shown in FIG. 47. The ideal is to have the angle flat in the middle such as shown in FIGS. 46 and 48.

A stiffer cuff made from a material with a higher modulus of elasticity would produce a greater rate of fall as compared to that shown in FIG. 48. For prior art inflatable cuffs, the relatively very high stiffness results in a very large change in cushion seal force for very slight displacements that may lead to a loss of the seal of the face. Events that may lead to slight displacement include, for example, nocturnal movements that result in changes to strap tightness, human face fluid reduction, relaxation of the lower jaw, etc.

In a further embodiment, the elastic cuff 170 may be filled with any compressible or non-compressible fluid, or some combination thereof. The fluid could be, for example, air, flowable liquid, flowable or semi-flowable gel. In the case of air, the cuff walls in tension cause the air inside the cuff to compress and forces the cushion seal outwards towards the face; there is some compression of the air as it is a gas. In the case of liquid filled, all the force onto the cushion seal is acted on by the cuff wall tension alone without the influence of compressed gas also.

Change in behavior of the cushion is achieved by any of or combination of modulus of elasticity, geometry/shape of the elastic cuff, material choice (for example the modulus of elasticity), and the initial mass of fluid (before fitting).

The initial mass of fluid may be adjusted by a valve either manually or automatically (incorporating external-internal control relative to cuff pressure and/or treatment CPAP pressure). In FIG. 45, it can be seen that the elastic cuff is separate from the cushion assembly, i.e. that portion of the cushion which seals against the face. It therefore provides minimal possible displacement, and only describes a flexible pneumatic seal, not elastic or resilient.

In FIG. 45, the expandable/contractible elastic cuff 170 is incorporated into the cushion seal.

In another embodiment, the elastic cuff may be pressurized with a manual pump 180 to fine tune the initial mass of fluid in the elastic cuff 170. See, for example, FIG. 49.

Another embodiment may incorporate automatic cuff mass of fluid change that can synchronize to delivered treatment pressure and/or react to leak or discomfort sensing.

Any elastic material that can be formed into a chamber or the elastic cuff 170 may be used. The use of a latex balloon is one material that may be used. Also, low durometer and/or low modulus of elasticity characteristic silicone rubbers may also be used, or a combination thereof. The cuff may have rigid or semi-rigid detail to provide structural integrity.

The cuff 170 need not surround the entire perimeter. For example, it may be excluded around the nasal bridge to modify received cushion seal forces. The elastic cuff 170 as disclosed herein may also be incorporated or used in conjunction with prior art mask systems, to create a new and improved product. For example, Respironics makes a "Profile Lite" gel cushion that could incorporate the elastic cuff 170 either integrated or otherwise attached between the frame and sealing interface. The elastic cuff may be filled with a compressible or non-compressible fluid such as air or gel, or any combination thereof.

In another example, the elastic cuff 170 may be combined with aspects of U.S. Pat. No. 4,971,051 to Toffolon. The elastic cuff could be incorporated as part of the cushion assembly to provide a force action in the cushion seal and also independent movement/displacement of the cushion seal relative to the mask frame.

While a nasal mask has been described in the preferred embodiments, the principles of the invention can be applied to full-face masks or mouth masks. Furthermore, the principles of the invention can be applied to nasal masks having a very small sealing region sealing near the flares.

"Boomerang" Seal

Figure 50:
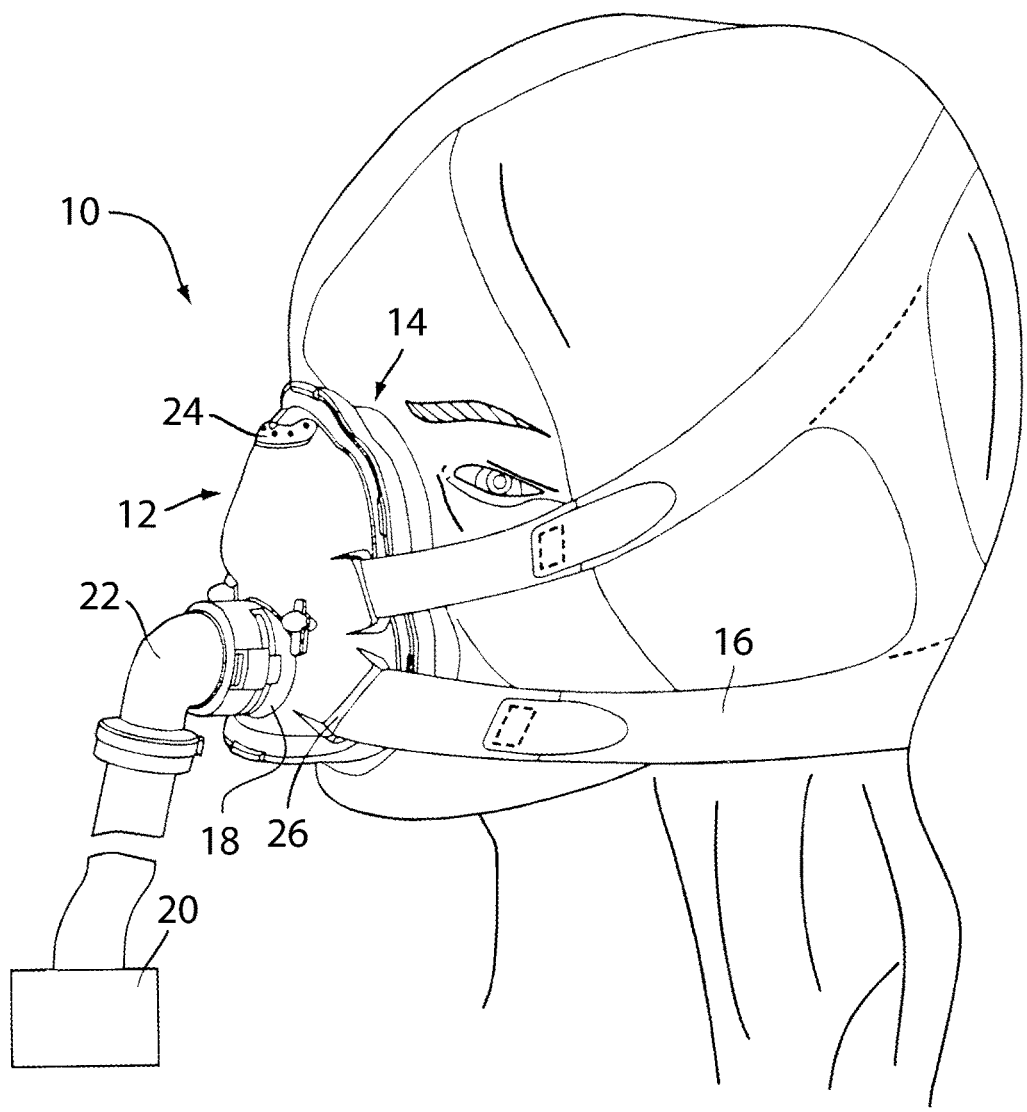
FIG. 50 is a front perspective view of a full face mask positioned on a wearer in accordance with a preferred embodiment of the invention.

FIGS. 50-56 illustrate another embodiment of the invention which may be usable with earlier embodiments. FIG. 50 is a perspective view of the full face respiratory mask 10 secured to a wearer's head. The mask 10 includes a frame 12 that supports a cushion 14. The mask 10 is secured over the wearer's nasal area and mouth by head gear that includes fastening straps 16 that may be adjusted around the wearer's head.

The frame 12 is preferably saddle shaped, generally triangular or trapezoidal to fit over the wearer's nose, or at least over the wearer's nares, and extends downwardly on each side of the mouth to the chin. The frame 12 has a port 18 for connection to a breathable gas supply 20 through a swivel elbow assembly 22. The gas supply 20 may be a pressurized gas supply that supplies breathable gas to an inner chamber in the mask 10 that receives the wearer's nose and mouth.

The frame 12 also preferably includes a vent opening 24 through which expired gas is exhausted. Fasteners 26 are provided to secure the straps 16 of the head gear and allow selective adjustment of the head gear. In this case, the fasteners 26 are slots formed in the frame 12 through which the straps 16 are fed. Of course, any suitable fastener can be used. If desired, a forehead support may also be used, which would extend from the frame upward toward the forehead.

Figure 51:
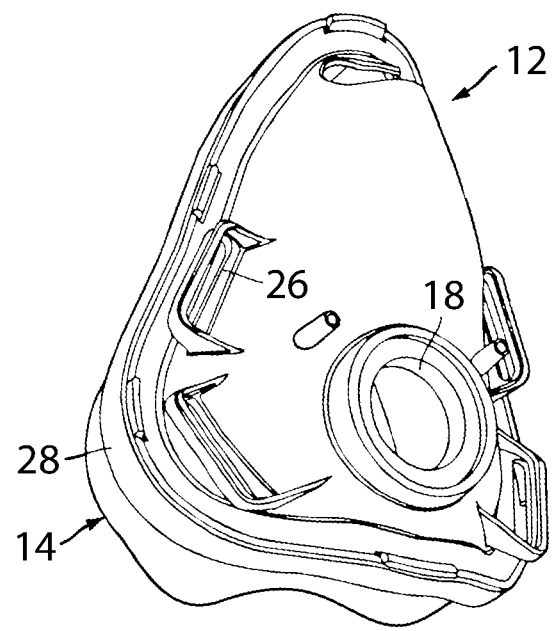
FIG. 51 is a front perspective view of the mask frame and cushion in accordance with a preferred embodiment of the invention.

The frame 12 is shown alone with the cushion 14 in FIG. 51. As can be appreciated by those of ordinary skill in the art of respiratory masks, the cushion 14 may be secured to a flange 28 on the frame 12 by a variety of methods. The cushion 14 may be formed integral with the flange 28, it may be adhered to the flange 28, or it may be removably clipped thereto. Other methods of attachment could also be used including straps, friction or interference fit, or tongue and groove.

Figure 52:
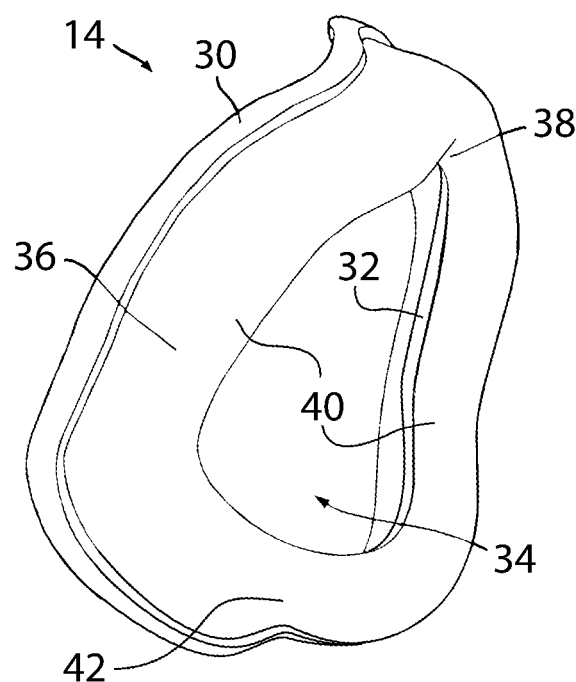
FIG. 52 is a rear perspective view of the cushion in accordance with a preferred embodiment of the invention.

In FIG. 52, the cushion 14 is removed from the frame 12 and flipped over with respect to the view in FIG. 51 to show the face contacting portions of the cushion 14. The cushion 14 includes a flange 30 that connects to the mask 12, an inner rim 32 that defines an opening 34 to the inner chamber of the frame 12, and a sealing portion 36 disposed between the flange 30 and the inner rim 32.

Preferably, the cushion 14 is formed of a soft, flexible skin compatible material such as silicone. One suitable material is SILASTIC™, a silicone elastomer manufactured by Dow Corning. It may be molded, by a one shot injection process as known in the art, for example. Different portions of the cushion 14 may be made with different thicknesses, or even of different materials to affect stiffness and resiliency for example. It is also contemplated that the cushion 14 may be made in whole or in part of foam or gel materials. The cushion 14 may be made based on a combination of the above processes and materials.

Figure 56:
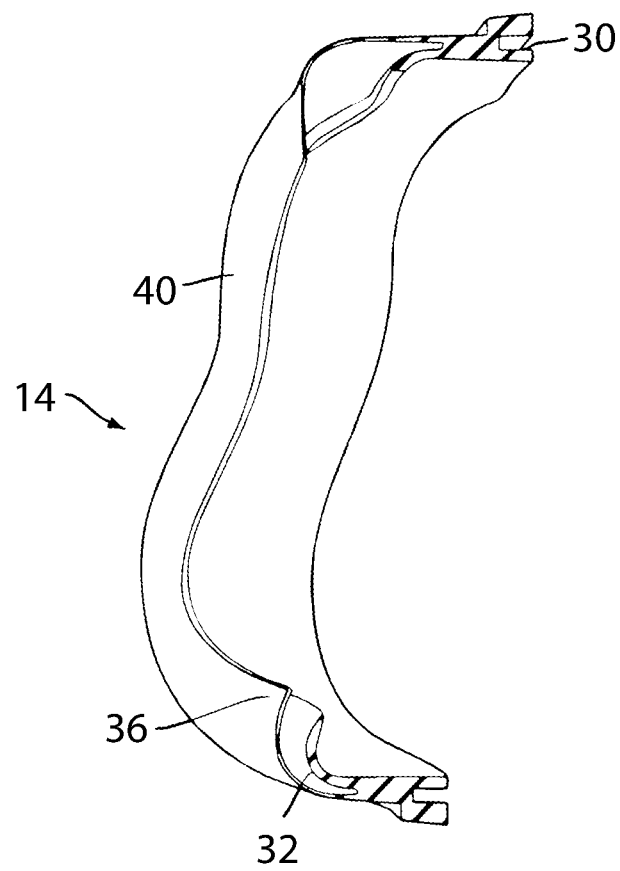
FIG. 56 is a cross section side perspective view of the cushion taken along line 56-56 of FIG. 54.

The inner rim 32 and sealing portion 36 are best seen in FIG. 56, which shows that the sealing portion 36 has a gently curved shape that provides a lip that extends beyond the inner rim 32. Preferably, the sealing portion 36 is formed to be more flexible or thinner than the inner rim 32 to conform more easily to the wearer's facial contours. The sealing portion 36 offers a compliant seal, which can accommodate small variations in the shape of the wearer's face and can account for small movements of the mask relative to the wearer while maintaining an effective seal. Depending upon the securing force supplied to the mask 10, the cushion 14 may deform to a point where it butts against the rim 32. The flange 30 has a rigidity sufficient to withstand usual securing pressures in use of the full-face cushion 14 and tends to retain its shape and resist deformation. It thus also acts as a supporting structure.

The embodiment shown herein has a single rim 32 and a single sealing portion 36 thus forming a double walled construction. It is also possible to have a single, triple or multiple walled construction. Further, the rim 32 and the sealing portion 36 could be made of different materials.

If desired, the sealing portion 36 can include a gusset portion that is a gently curved enlarged portion that follows the curvature of the face.

Figure 53:
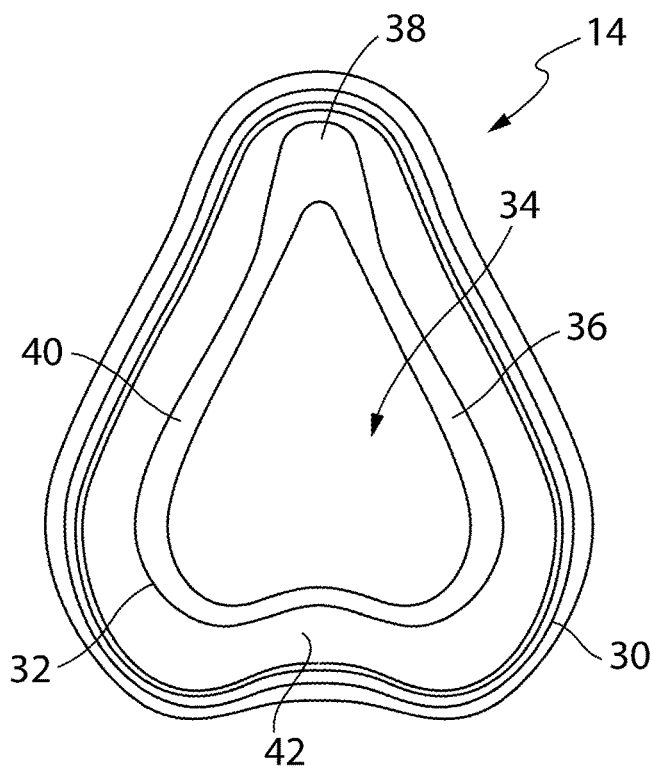
FIG. 53 is a front view of the cushion of FIG. 52.
Figure 54:
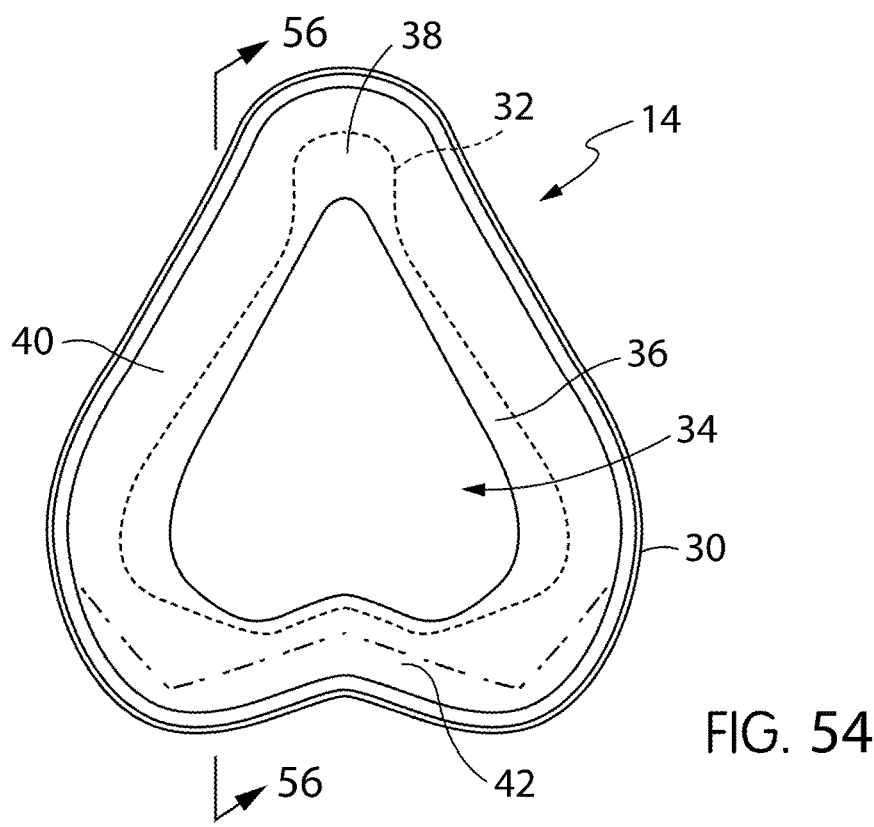
FIG. 54 is a rear view (from the wearer's side) of the cushion of FIG. 52.

The sealing portion 36 is designed to contact the wearer's face and form a seal therewith so that the gas supplied to the inner chamber of the frame 12 does not leak outside the mask 10. The sealing portion 36 includes a nasal section 38 that spans the nasal area, which extends above the wearer's nares across the bridge of the nose and is generally an inverted V-shape as seen in FIGS. 52-54. On each side of the nasal section 38, side sections 40 extend downwardly to the outside of both sides of the wearer's mouth, continuing the generally inverted V-shape. A chin section 42 extends between the side sections 40 and is described in greater detail below.

Figure 55:
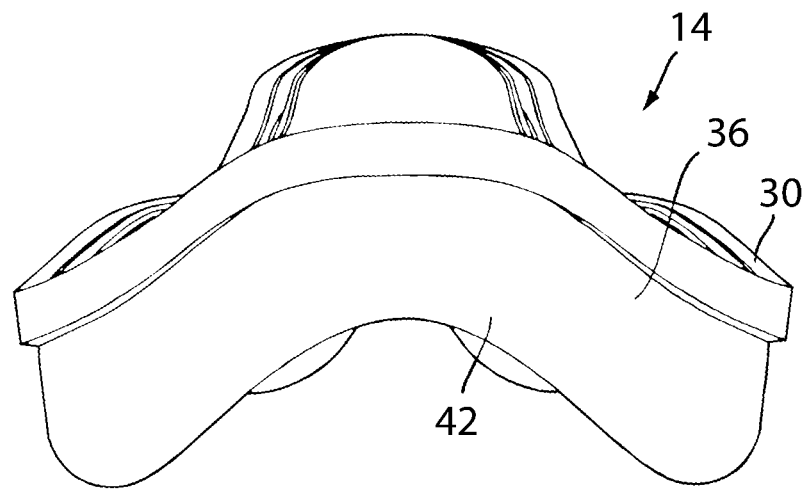
FIG. 55 is a bottom view of the cushion of FIG. 52.

The profile of the cushion 14 when viewed from above or below has an concave central portion at the nasal end and the chin end and a convex portion at the cheek portions to fit a wearer's face as seen in FIG. 55. That is, in the plane perpendicular to a wearer's face, the cushion 14 is curved to follow the contours of the human face, including the protruding nose and chin. This is known in the art of respiratory masks.

Referring to FIGS. 53 and 54, the chin section 42 of the cushion 14 assumes a shape when viewed from the front and the rear that is not conventional in respiratory masks. As discussed above, in conventional masks, the chin section of a cushion is straight or U-shaped in the plane generally parallel to the wearer's face. The conventional idea is to make the chin section conform closely around the mouth. However, in this embodiment of the invention, the chin section 42 is shaped to closely conform to the chin's bony contour instead. The bone descriptor for this region is between the mental protuberance and lower teeth on the jaw, and it forms an outwardly extending bone line that is curved downward, much like the shape of a frown. The cushion 14 therefore includes the chin region 42 that is shaped like a boomerang or an inverted U and is designed to rest between the lower lip and the mental protuberance. As seen in FIG. 54, the shape of the seal may be described as W-shaped. Any portion of the inverted U or W shape may be adjustable to refine the fit on the wearer. For example, a malleable wire could be formed in the sealing portion to provide such adjustability, by bending the wire to conform the sealing portion to the wearer's facial contours. This upwardly curved design or arch is seen in FIGS. 51-54. The section rear view may have an arched shape while the front and/or side views could still maintain the current shape of the full face mask.

This shape allows the side sections 40 to extend farther downward toward the lower jaw. If desired, the cushion 14 can be sized to extend to the lower jaw to provide more stable support. By this, the cushion 14 rests on the bony regions of the face that are less likely to change shape and compromise the seal than the softer, fatty regions like the lower lip and cheek.

During treatment, as pressure is applied to the wearer, the lips, which are flexible, are forced slightly open. The lower lip thus moves outwardly and slightly downwards. As the lower lip moves as described, an intimate contact with the arch shaped cushion 14 is created, improving the sealing even further, and/or reducing leak through the mouth, if desired.

The cushion 14 and mask 10 have been described with reference to CPAP or assisted respiration treatment, however it is to be understood that the invention generally is applicable to any application where gas and/or atomized liquid is to be supplied to the entrance of the airways. Such applications include nebulisers, gas masks and anesthetic machines. In addition, the mask can be for use with an oral only mouth mask where the mask covers the mouth only. Also, the cushion could extend down beyond the chin to further stabilize the cushion.

It can thus be appreciated that the aspects of the present invention have been fully and effectively accomplished. The foregoing specific embodiments have been provided to illustrate the structural and functional principles of the present invention, and are not intended to be limiting. To the contrary, the present invention is intended to encompass all modifications, alterations and substitutions within the spirit and scope of the detailed description.

What is claimed is:
1. A respiratory mask assembly, comprising:
  a frame; and
  a cushion provided to the frame, the cushion including:
    a non-face contacting portion removably attached to the frame;
    a face-contacting portion adapted to engage a patient's face, the face-contacting portion including a side wall, a rim extending from the side wall and curving inwardly into a cavity of the cushion, and a membrane substantially surrounding the rim and including an inside surface spaced from an outside surface of the rim;
    a gusset portion extending radially outwardly from the side wall of the face-contacting portion; and
    a reinforcing ring between the gusset portion and the face-contacting portion, said reinforcing ring being constructed and arranged to act as a stiffening hoop to reduce the tendency of the cushion to expand when under pressure.

2. A respiratory mask assembly according to claim 1, wherein said reinforcing ring comprises polycarbonate.

3. A respiratory mask assembly according to claim 1, wherein the respiratory mask assembly is a nasal mask assembly.

4. A respiratory mask assembly according to claim 1, further comprising a forehead support provided to an upper portion of the frame.

5. A respiratory mask assembly according to claim 4, further comprising headgear including upper straps removably connected to clip structures provided to the forehead support and lower straps removably connected to clip structures provided to the frame.

6. A respiratory mask assembly according to claim 1, further comprising a swivel elbow assembly provided to a front portion of the frame.

7. A respiratory mask assembly according to claim 1, wherein the membrane is thinner than the rim.

8. A respiratory mask assembly according to claim 1, wherein the gusset portion extends radially outwardly a distance away from the side wall of the face-contacting portion to provide additional footprint area outside a contact line of the cushion.

9. A respiratory mask assembly according to claim 8, wherein the distance is varied in different regions of the gusset portion.

10. A respiratory mask assembly according to claim 9, wherein the distance in a nasal bridge region is different than the distance in cheek regions.

11. A respiratory mask assembly according to claim 9, wherein the additional footprint area is at least partially determinative of a contact force applied to the patient's face through the face-contacting portion, and the distance is varied in different regions of the gusset portion to vary the contact force applied in different regions of the patient's face.

12. A respiratory mask assembly according to claim 1, wherein the gusset portion extends around an entire perimeter of the cushion.

13. A respiratory mask assembly according to claim 1, further comprising a spring structure to provide a component of a contact force on the patient's face.

14. A respiratory mask assembly according to claim 1, wherein the non-face contacting portion, the face-contacting portion, and the gusset portion have a generally triangular shape.

15. A respiratory mask assembly according to claim 1, further comprising a cushion clip detachably engaged with the frame such that a shoulder of the non-face contacting portion is positioned between the clip and the frame to attach the cushion to the frame.

16. A respiratory mask assembly according to claim 1, wherein the non-face contacting portion, the face-contacting portion, and the gusset portion comprise silicone.

17. A respiratory mask assembly according to claim 1, wherein the respiratory mask assembly is a nasal and mouth mask assembly.

18. A respiratory mask assembly according to claim 1, wherein the reinforcing ring is provided to the cushion at a point between the gusset portion and the face-contacting portion, the reinforcing ring constructed and arranged to reduce the tendency of the cushion to expand at the point when under pressure.

19. A respiratory mask assembly according to claim 18, wherein the reinforcing ring extends in a ring around the entire perimeter of the cushion with the point provided at a junction between the gusset portion and the side wall of the face-contacting portion.

20. A respiratory mask assembly according to claim 1, wherein at least a portion of the reinforcing ring extends along an interior surface of the cushion within the cavity.

21. A respiratory mask assembly according to claim 1, wherein the reinforcing ring comprises an overmolded connection to the cushion.

22. A respiratory mask assembly according to claim 21, wherein at least a portion of the reinforcing ring extends along an interior surface of the cushion within a cavity of the cushion.

23. A respiratory mask assembly according to claim 21, wherein the reinforcing ring comprises polycarbonate.

24. A respiratory mask assembly according to claim 21, wherein the reinforcing ring comprises the overmolded connection to the cushion at a point between the gusset portion and the face-contacting portion such that the reinforcing ring extends in a ring around the entire perimeter of the cushion with the point provided at a junction between the gusset portion and the side wall of the face-contacting portion.

25. A respiratory mask assembly according to claim 1, wherein the reinforcing ring comprises a push-fit connection to the cushion.

26. A respiratory mask assembly according to claim 25, wherein at least a portion of the reinforcing ring extends along an interior surface of the cushion within a cavity of the cushion.

27. A respiratory mask assembly according to claim 25, wherein the reinforcing ring comprises polycarbonate.

28. A respiratory mask assembly according to claim 25, wherein the reinforcing ring comprises the push-fit connection to the cushion at a point between the gusset portion and the face-contacting portion such that the reinforcing ring extends in a ring around the entire perimeter of the cushion with the point provided at a junction between the gusset portion and the side wall of the face-contacting portion.

* * * * *